United States Patent
Inchauspe et al.

(10) Patent No.: US 7,695,960 B2
(45) Date of Patent: Apr. 13, 2010

(54) COMPOSITION COMPRISING THE POLYPROTEIN NS3/NS4 AND THE POLYPEPTIDE NS5B OF HCV, EXPRESSION VECTORS INCLUDING THE CORRESPONDING NUCLEIC SEQUENCES AND THEIR THERAPEUTIC USE

(75) Inventors: Geneviève Inchauspe, Lyons (FR); Anne Fournillier, Lyons (FR); Jean-Daniel Abraham, Strasbourg (FR); Maria Dimitrova-Tchomakov, Strasbourg (FR); Marie Parnot, Strasbourg (FR)

(73) Assignees: Transgene S.A., Strasbourg (FR); Institut National de la Sante et de Recherche Medicale, Paris Cedex (FR)

( * ) Notice: Subject to any disclaimer, the term of this patent is extended or adjusted under 35 U.S.C. 154(b) by 0 days.

(21) Appl. No.: 11/723,638

(22) Filed: Mar. 21, 2007

(65) Prior Publication Data

US 2007/0269460 A1 Nov. 22, 2007

Related U.S. Application Data

(63) Continuation-in-part of application No. 10/559,431, filed as application No. PCT/FR2004/050214 on Jun. 4, 2004.

(30) Foreign Application Priority Data

Jun. 5, 2003 (FR) .................................. 03/06772

(51) Int. Cl.
*A61K 48/00* (2006.01)
*C12N 15/63* (2006.01)

(52) U.S. Cl. .................. 435/320.1; 514/44; 424/228.1; 424/93.1; 424/93.3

(58) Field of Classification Search .............. 424/228.1, 424/93.1
See application file for complete search history.

(56) References Cited

U.S. PATENT DOCUMENTS

| 6,312,889 | B1 * | 11/2001 | Houghton et al. | 435/5 |
| 6,562,346 | B1 * | 5/2003 | Paliard et al. | 424/189.1 |
| 6,986,892 | B1 * | 1/2006 | Coit et al. | 424/228.1 |
| 7,052,696 | B2 * | 5/2006 | Fields et al. | 424/184.1 |
| 7,285,539 | B2 * | 10/2007 | Paliard et al. | 514/44 |

FOREIGN PATENT DOCUMENTS

WO    WO01/30812 A2 * 5/2001

OTHER PUBLICATIONS

Clarke B et al. J. Gene Virol. 1997, vol. 78, pp. 2397-2401.*
Pancholi et al. J. Virol. Jan. 2003, vol. 77, No. 1, pp. 382-390.*
Hadziyannis et al. Expert Opinion, Apr. 2003, vol. 4, No. 4, pp. 541-551).*
Cho et al. Vaccine, 1999, vol. 17, No. 9-10, pp. 1136-1144.*
Paul et al. cancer Gene Ther. 2002, vol. 9, pp. 470-477.*
Inchauspe et al. Clinics in Liver Disease, 2003, vol. 7, pp. 243-259.*
Purcell et al. Hepatology, 1997, vol. 26, pp. 11S-114S.*
Hsu et al. Clinics in Liver Disease 1999, vol. 6, pp. 901-915.*
Krieger et al. J. Virol. 2001, vol. 75, No. 10, pp. 4614-4624.*

* cited by examiner

*Primary Examiner*—Gary B. Nickol
*Assistant Examiner*—Bao Qun Li
(74) *Attorney, Agent, or Firm*—Buchanan Ingersoll & Rooney PC

(57) ABSTRACT

The invention relates to a peptidic compound containing a polyprotein NS3/NS4 of a hepatitis C virus and a polypeptide NS5b of hepatitis C virus. Said invention also relates to expression vectors such as adenovirus and poxyvirus in which nucleic sequences coding for the polyprotein NS3/NS4 and the polypeptide NS5b. The inventive compound can be used for a therapeutic application.

32 Claims, 28 Drawing Sheets

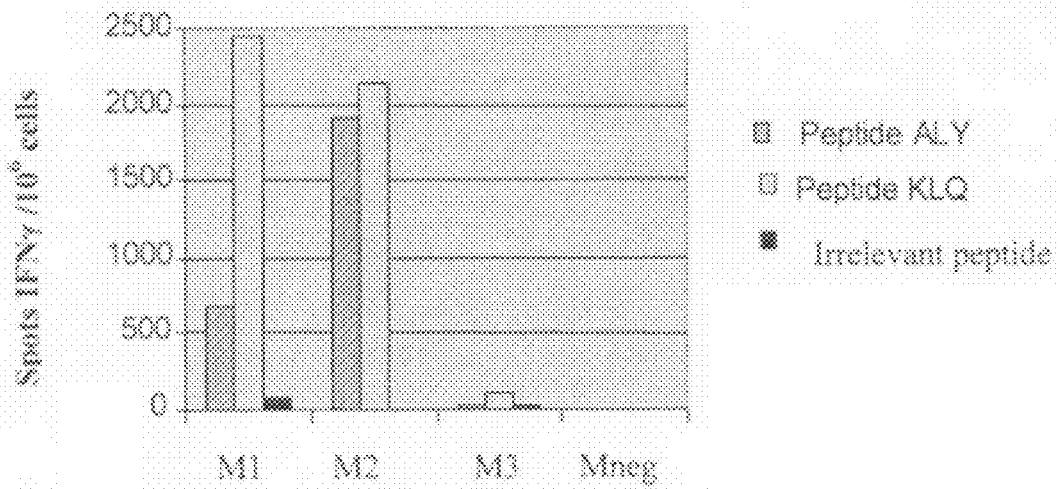
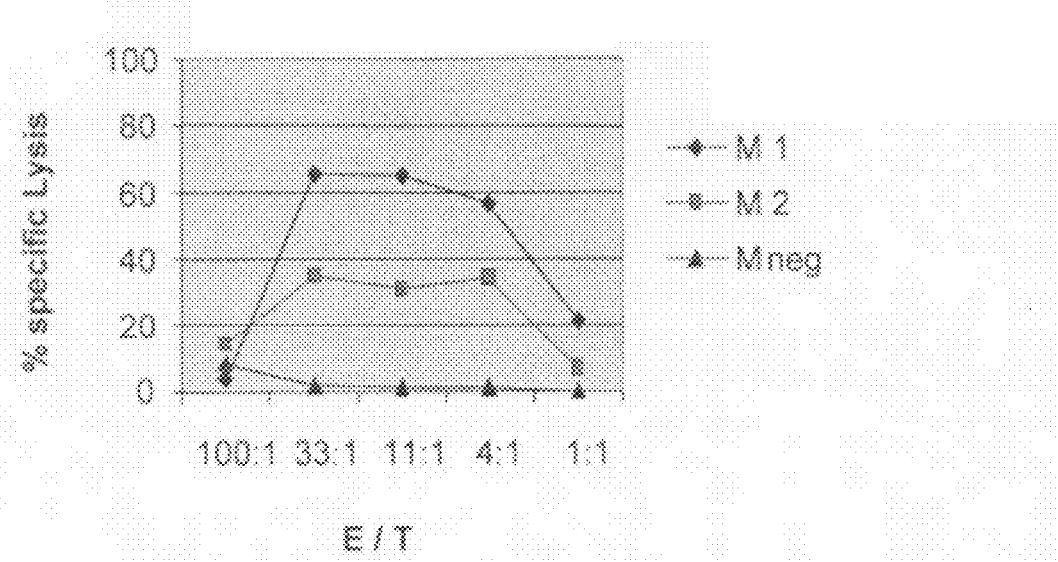

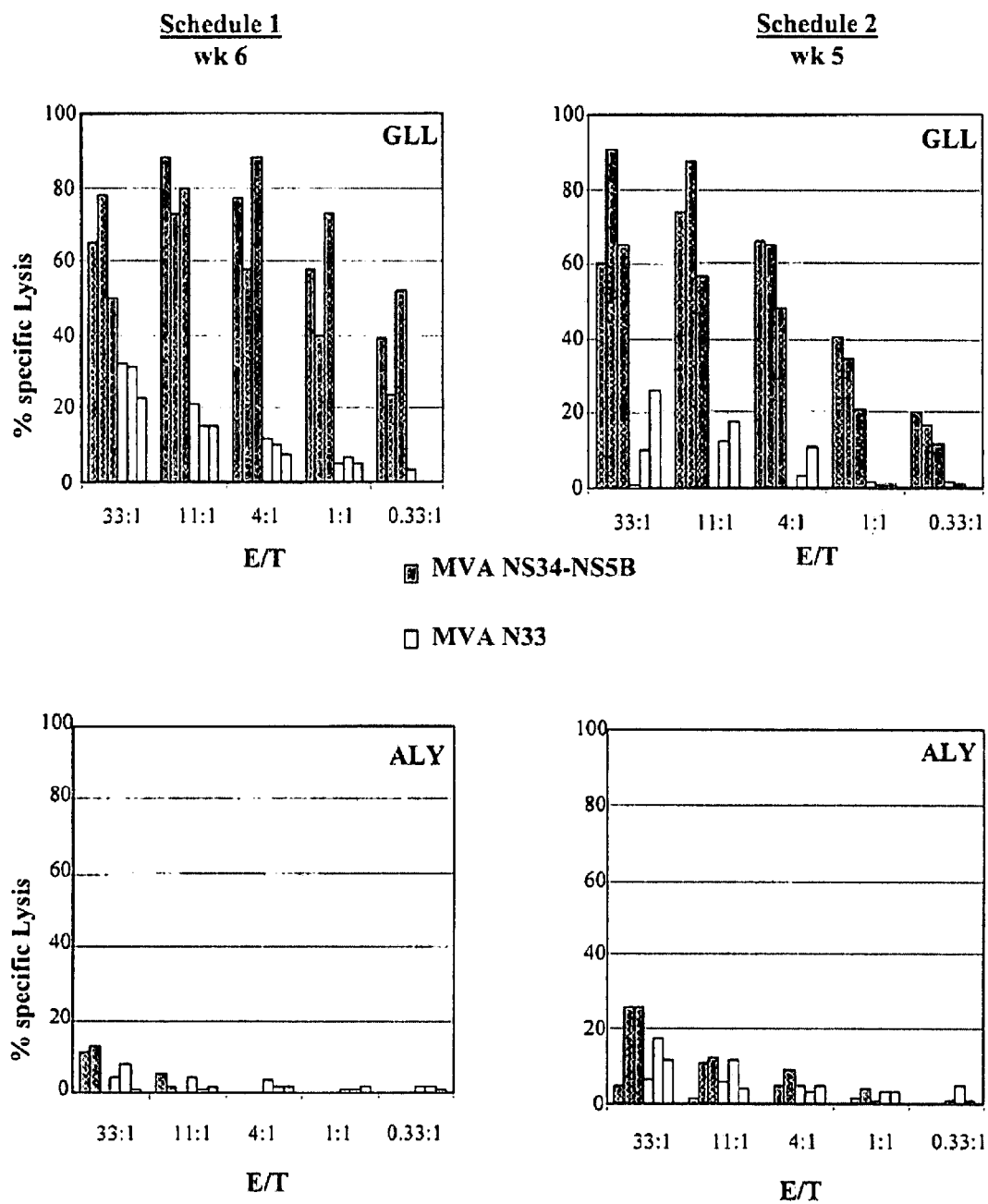

Figure 15:
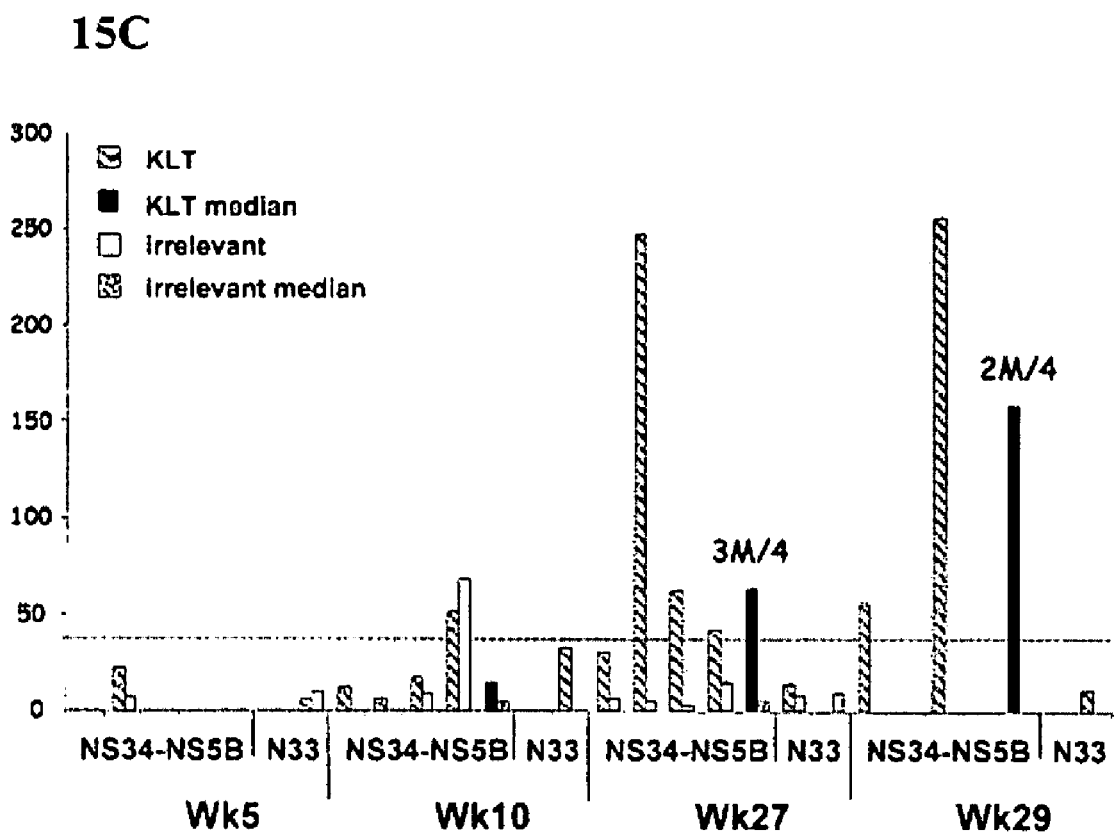

Figure 15
15A
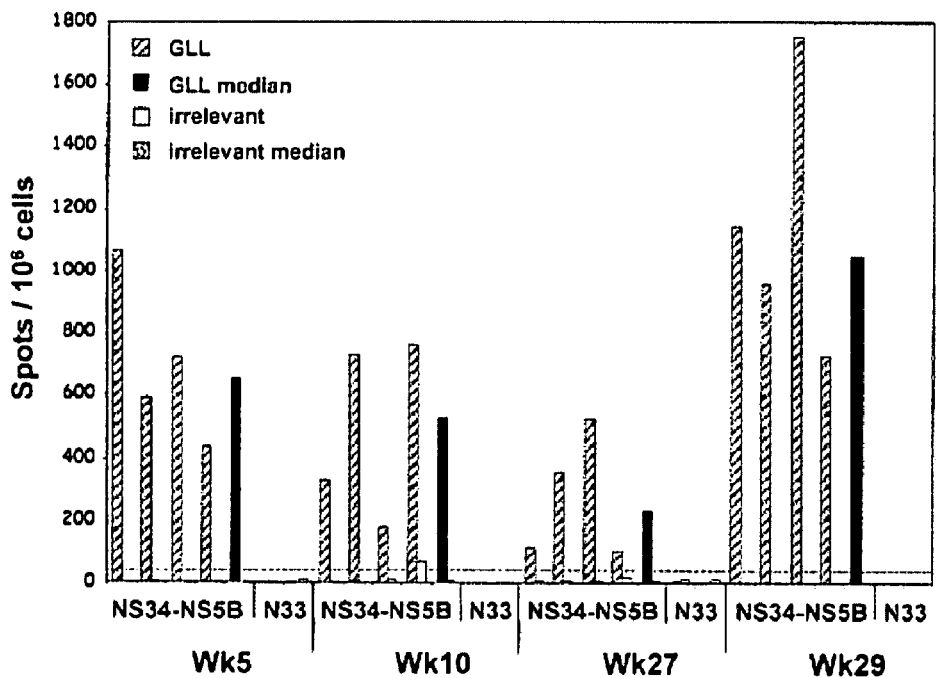
15B
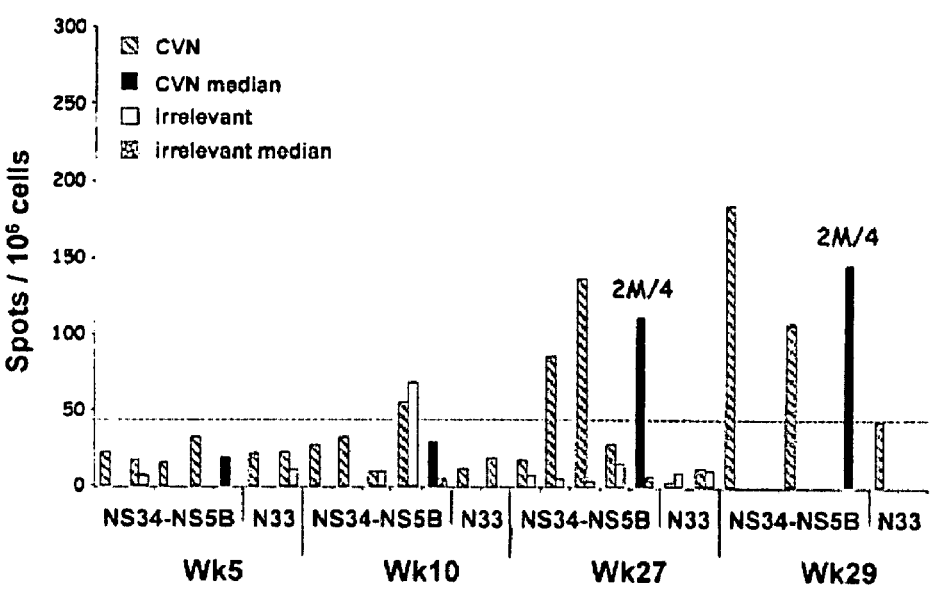

COMPOSITION COMPRISING THE POLYPROTEIN NS3/NS4 AND THE POLYPEPTIDE NS5B OF HCV, EXPRESSION VECTORS INCLUDING THE CORRESPONDING NUCLEIC SEQUENCES AND THEIR THERAPEUTIC USE

The present invention relates to the field of prophylactic and therapeutic vaccination directed against the hepatitis C virus (HCV). It relates in particular to a novel composition containing a polyprotein corresponding to the two colinear proteins NS3 and NS4 (hereafter called polyprotein NS3/NS4) and a polypeptide constituted by NS5b, the vectors, such as adenovirus or poxvirus, capable of expressing this composition and their use as vaccine.

Hepatitis C is the major cause of transfusion-acquired hepatitis. Hepatitis C can also be transmitted by other percutaneous routes, for example by injection of drugs by intravenous route. The risk of contamination of health professionals is moreover not negligible. Sexual transmission has been described.

Hepatitis C differs from other forms of liver diseases associated with viruses, such as hepatitis A, B or D. The infections by the hepatitis C virus (HCV or HCV) are mostly chronic resulting in diseases of the liver, such as hepatitis, cirrhosis and carcinoma in a large number of cases (5 to 20%) and represents 30% of the hepatic transplants in developed countries.

Although the risk of transmission of the virus by transfusion has diminished owing to the introduction of screening tests in the 1990s, the frequency of new HCV infections remains high. By way of example, a recent study indicates that today there are still 10,000 to 15,000 new cases of infection per year in France (S. Deuffic et al., Hepatology 1999; 29: 1596-1601). Currently, approximately 170 million people worldwide are chronically infected by HCV (Hepatitis C: Global prevalence (update), 2000, Weekly Epidemiological Record, Vol 75(3)). The high-risk populations are principally hospital staff and intravenous-drug users, but there are asymptomatic blood donors who do not belong to these high-risk groups and in whom circulating anti-HCV antibodies have been found. For the latter, the infection route has not yet been identified. HCV infections therefore exist (estimated at between 5 and 10%), known as sporadic infections, the etiology of which is unknown and which cannot be controlled.

HCV was the first hepatotropic virus isolated by means of molecular biology techniques. The viral genome sequences were cloned before the viral particle was visualized.

HCV belongs to a new genus of the *Flaviviridae family*, the hepaciviruses. It is a positive single-strand RNA virus, of 9.5 kb, which is replicated by a complementary RNA copy and the translation product of which is a polyprotein precursor of approximately 3,000 amino acids. The 5' end of the HCV genome corresponds to an untranslated region adjacent to the genes that code for the structural proteins, the core protein of the nucleocapsid, the two envelope glycoproteins, E1 and E2, and a small protein called p7. The 5' untranslated region and the gene core are relatively well preserved in the different genotypes. The envelope proteins E1 and E2 are encoded by regions that are more variable from one isolate to another. The protein p7 is an extremely hydrophobic protein, which may constitute an ion channel. The 3' end of the HCV genome contains the genes that code for the non-structural proteins (NS2, NS3, NS4, NS5) and for a 3' non-coding region possessing a well-conserved domain (Major M E, Feinstone S M, Hepatology, June 1997, 25 (6): 1527-1538).

At present, the most effective therapy for the treatment of hepatitis C combines pegylated interferon and ribavin (Manns M P et al., The Lancet, 22 Sep. 2001, Vol. 358, 958-965). Whilst this therapy is particularly effective in the case of patients infected by viral strains belonging to the genotypes 2 and 3, it still has only a limited effect on the genotypes 1a, 1b and 4 (Manns M P, op. cit.). Less than 50% of the treated patients become "long-term responders". Moreover, this therapy is an expensive intervention (10,000 to 15,000 euros/patient/year) and is associated with toxic effects. In fact, 5 to 10% of the patients are obliged to stop treatment before the end.

It is therefore necessary to develop a vaccine composition targeting all the genotypes.

Several studies now show that the control of an infection caused by HCV either naturally (spontaneous resolution), or after treatment (therapeutic resolution) is associated with the induction or potentialization of cell-mediated immune responses involving the T-CD4$^+$ and T-CD8$^+$ lymphocytes (as described for example in LECHNER, F. et al., Eur. J. Immunol., 30: 2479-2487 (2000) and in Thimme R. et al., 2001, J. Exp. Med., 194 (10): 1395-1406).

The molecules of the major histocompatibility complex (MHC, also known as HLA in humans) are referred to as class I or class II. The class I molecules are expressed on virtually all of the nucleated cells and are able to present epitopes or peptides to the CD8$^+$ cytotoxic T lymphocytes (CTL). The class II molecules are able to present epitopes to the CD4$^+$ T cells, but their expression is restricted to antigen-presenting cells.

The vaccines against the hepatitis C virus currently envisaged are based on the use of adjuvant recombinant proteins, peptides, expression vectors among which there can be mentioned vectors of viral or bacterial origin or of naked DNA. In this case, one or more viral proteins or one or more genes coding for these viral proteins are used.

When several viral proteins or one or more genes coding for these viral proteins are selected, the latter are often constituted either by some or all of the structural proteins (Makimura et al., 1996, Vaccine, 14: 28-34; Fournilier A. et al., 1999, J. Virology, 73: 7497-7504), or by individual non-structural proteins or comprising at least two contiguous proteins (Brinster et al., 2001, Hepatology, 34: 1206-1217), or by a mixture of structural and non-structural proteins (Pancholi et al., 2003, J. Virology, 77: 382-390).

The Patent Application WO99/38880 describes the use of three genes coding separately for the three proteins NS3, NS4 and NS5 (a and b) in a vaccine composition comprising three DNA vaccines each expressing these three proteins separately. The authors show the induction of T lymphocytes specific to the three antigens in mice. Only the vaccine expressing NS5a and b has been tested in vivo in a protection test.

The Patent Application WO01/30812 describes the use of a fusion protein constituted by the non-structural proteins NS3, NS4 and NS5a, if necessary in combination with the non-structural protein NS5b. The authors have indicated that this combination made it possible to activate the HCV-specific T cells. This patent application simply describes the ability of vaccine formulations (naked-DNA, recombinant-adenovirus or recombinant-vaccinia-virus type) expressing the fusion protein NS3, NS4, NS5a or the protein NS5a to induce specific immune responses mediated by specific T lymphocytes.

The Applicant has now demonstrated, against all expectation, that the particular combination of the non-structural proteins NS3, NS4 and NS5b, NS3 and NS4 being expressed colinearly had a better immunogenic power and protective power superior to that obtained with a vaccine also including, apart from these non-structural proteins, the protein NS5a and/or other structural proteins of HCV such as core, E1 or E2, and had an effect on the ability of cells originating from patients infected by viral strains to induce specific immune responses.

Thus, an object of the present invention is a peptide composition comprising a polyprotein NS3/NS4 of the hepatitis C virus, as well as a polypeptide NS5b of the hepatitis C virus.

An object of the invention is also the vectors including the nucleotide sequences coding for this peptide composition, such as the adenoviruses and poxviruses, as well as microorganisms or host cells transformed by these vectors.

An object of the invention is also a pharmaceutical composition comprising as active ingredient the peptide composition, vector(s) or antibodies of the invention and a pharmaceutically acceptable vehicle.

An object of the invention is also antibodies directed against the peptide composition of the invention, as well as the use of the peptide composition, vectors, pharmaceutical composition or antibodies for the preparation of a medicament intended for the inhibition or control of an infection caused by the hepatitis C virus, and in a vaccine composition.

Another object of the invention is a method of treatment of one or more pathologies associated with an hepatitis C virus, which comprises at least one administration to a host organism of an effective dose of any of the above-described active ingredient (peptide composition, vector, antibodies and/or pharmaceutical composition) or any combination thereof.

An object of the invention is finally a method of stimulating a cell-mediated immune response against an hepatitis C virus protein which comprises the step of administering in a host organism at least one dose of the peptide composition, vector, pharmaceutical composition or antibodies.

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products, compositions and methods, the term "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps. For example, a polypeptide "consists of" an amino acid sequence when the polypeptide does not contain any amino acids but the recited amino acid sequence. A polypeptide "consists essentially of" an amino acid sequence when such an amino acid sequence is present together with only a few additional amino acid residues, typically from about 1 to about 50 or so additional residues. A polypeptide "comprises" an amino acid sequence when the amino acid sequence is at least part of the final amino acid sequence of the polypeptide. Such a polypeptide can have a few up to several hundred additional amino acids residues. Such additional amino acid residues may play a role in polypeptide trafficking, facilitate polypeptide production or purification; prolong half-life, among other things. The same can be applied for nucleotide sequences.

The present invention therefore proposes a novel peptide composition constituted by a polyprotein NS3/NS4 and a polypeptide NS5b of HCV, which composition has the ability to stimulate a cell-mediated immune response specific to HCV, such that it is useful in the field of prophylactic and therapeutic vaccination directed against the hepatitis C virus.

The polyprotein NS3/NS4 of the peptide composition of the invention is constituted by the protein NS3 and the protein NS4a and b, without interruption in the peptide sequence, as in the native polyprotein. In fact, as indicated previously, the HCV genome contains a single open reading frame that is transcribed into a polyprotein. This HCV polyprotein can be cleaved in order to produce at least ten distinct parts, in the order $NH_2$-Core-E1-E2-p7-NS2-NS3-NS4a-NS4b-NS5a-NS5b-COOH.

For general guidance, the protein NS3 is a protein of 630 amino acids, which appears approximately from amino acid 1027 to amino acid 1657 of the polyprotein. The protein NS4, a protein of 314 amino acids, appears approximately from amino acid 1658 to amino acid 1972 (numbering with respect to HCV-1) (Choo et al., 1991, Proc. Natl. Acad. Sci., vol 88: 2451-2455). The polyprotein NS3/NS4 therefore appears approximately from amino acid 1027 to amino acid 1972.

As regards the polypeptide NS5b also contained in the composition of the invention, it is constituted by 590 amino acids and appears approximately from amino acid 2421 to amino acid 3011 of the polyprotein (Choo et al., 1991, op. cit.).

For sake of clarity, the amino acid stretches referred herein in connection with NS3, NS4 and NS5B proteins are given with respect to their positions in HCV-1 polyprotein precursor (as described by Choo et al., 1991, Proc. Natl. Acad. Sci. USA 88, 2451-2455 or in GenBank under accession number M62321). However, the present invention also encompasses NS3, NS4 and NS5B proteins of other HCV strains and isolates, as well as analogues or muteins thereof.

The protein NS3 comprises two distinct structural domains, namely an N-terminal domain endowed with an active serine protease activity that is involved in the maturation of the viral polyprotein, and a C-terminal domain comprising a helicase activity associated with an NTPase activity that plays a role in the replication of the viral genome.

By "polyprotein NS3/NS4" and "polypeptide NS5b", is of course meant the polyproteins and polypeptides having the native amino acid sequences, originating from any HCV strain and isolate, as well as their analogues, muteins and homologues.

By "analogues" or "muteins" of the polyprotein and of the polypeptide, is meant the biologically active derivatives of the reference molecules that have the desired activity, namely the ability to stimulate a cell-mediated immune response as defined above.

Generally, the term "analogue" refers to compounds having a native polypeptide sequence and structure having one or more additions, substitutions (generally conservative in terms of nature) and/or amino acid deletions, relative to the native molecule, to the extent that the modifications do not destroy the immunogenic activity. By the term "mutein", is meant the peptides having one or more elements imitating the peptide (peptoids), such as those described in the Patent Application PCT WO91/04282. Preferably, the analogue or the mutein have at least the same immunoactivity as the native molecule.

Processes for preparing polypeptide analogues and muteins are known to a person skilled in the art and are described below.

The particularly preferred analogues include substitutions that are conservative in nature, i.e. the substitutions, which take place in a family of amino acids. Specifically, the amino acids are generally divided into 4 families, namely (1) the acid amino acids such as aspartate and glutamate, (2) the basic amino acids such as lysine, arginine and histidine, (3) the non-polar amino acids such as alanine, leucine, isoleucine, proline, phenylalanine, methionine and tryptophane and (4) the polar non-charged amino acids such as glycine, asparagine, glutamine, cysteine, serine, threonine and tyrosine. Phenylalanine, tryptophane and tyrosine are sometimes classified as aromatic amino acids. For example, it can reasonably be predicted that an isolated replacement of leucine by isoleucine or valine, of an aspartate by a glutamate, of a threonine by a serine, or a similar conservative replacement of one amino acid by another amino acid having a structural relationship, will not have a major effect on the biological activity. A person skilled in the art will easily determine the regions of the peptide molecule of interest that can tolerate a change by referring to the Hopp/Woods and Kyte-Doolittle plots, well known in the art.

By "homology", is meant the percentage of identity between two peptide molecules, such as polyproteins and polypeptides. Two amino acid sequences are "more or less homologous" to each other when the sequences have at least 60%, preferably at least 75%, more preferably also at least 80-85%, more preferably also at least 90% and still more preferably at least 95-98% or more of sequence identity over a defined length of the peptide molecules.

Generally, the term "identity" refers to an exact amino acid to amino acid correspondence of two peptide sequences. The percentage of identity can be determined by a direct comparison of the sequence information between two molecules by aligning the sequences, counting the exact number of mismatches between the two aligned sequences, dividing by the length of the shorter sequence and multiplying the result by 100. The percentage of identity can also be determined using computer programs such as ALIGN, Dayhoff, M. O. in Atlas of Protein Sequence and Structure M. O. Dayhoffed., 1981, 5 Suppl., 3: 482-489.

The nucleic acid and amino acid sequences of a certain number of HCV strains and isolates, and in particular of the protein NS3, of the protein NS4 and of the polypeptide NS5b, have already been determined.

For example, the isolate HCV-J1 is described in Okamoto H. et al., 1992, Nucleic Acids Res., 20: 6410-6410. The complete coding sequences of two independent HCV isolates, namely the isolates HCV-J and -BK, have been described in Kato et al., 1990, Proc. Natl. Acad., Sci., 87: 9524-9528 and in Takamizawa et al., 1991, J. Virol., 65: 1105-1113 respectively. As regards the isolate HCV-1, it is described in Choo et al., 1990, Brit. Med. Bull., 46: 423-441 and in Choo et al., 1991, op. cit. The isolate HVC-H has been described in Inchauspe G. et al; 1991, Proc. Natl. Acad. Sci., 88: 10292-10296. The isolate HCV-G9 has been described in Okamoto H., et al., 1994, J. Gen. Virol., 45: 629-635. The isolates HCV-J6 and -J8 have been described in Okamoto H., et al., 1991, J. Gen. Virol., 72: 2697-2704 and Okamoto H., et al., 1992, Virology, 188: 331-341 respectively. The isolate HVC-BEBE1 has been described in Nako H., et al., 1996, J. Gen. Virol., 141: 701-704 and the isolate HCV-NZL1 has been described in Sakamoto M., et al., 1994, J. Gen. Virol., 75: 1761-1768. As regards the isolate HCV-Tr, it has been described in Chayama K., et al., 1994, J. Gen. Virol., 75: 3623-3628. The isolates HCV-ED43 and -EUH1480 have been described in Chamberlain R. W., et al., 1997, J. Gen. Virol., 78: 1341-1347 and Chamberlain R. W., et al., 1997, Biochem. Biophys. Res. Commun., 236: 44-49 respectively. The isolate HCV-EUHK2 has been described in Adams A., et al., 1997, Biochem. Biophys. Res. Commun., 234: 393-396. The isolates HCV-VN235, -VN405 and -VN004 have been described in Tokita H., et al., 1998, J. Gen. Virol., 79: 1847. Finally, as regards the isolates HCV-JK049 and -JK046, they have been described in Tokita H. et al., 1996, J. Gen. Virol., 77: 293-301.

The HCV strains and isolates, as illustrated above, can have different genotypes, namely genotypes 1a (isolates HCV-1, -J1 and -H), 1b (isolates HCV-J and BK), 1c (isolate HCV-G9), 2a (isolate HCV-J6), 2b (isolate HCV-J8), 2c (isolate HCV-BEBE1), 3a (isolate HCV-NZL1), 3b (isolate HCV-Tr), 4a (isolate HCV-ED43), 5a (isolate HCV-EUH1480), 6a (isolate HCV-EUHK2), 7b (isolate HCV-VN235), 8b (isolate HCV-VN405), 9a (isolate HCV-VN004), 10a (isolate HCV-JK049) and 11a (isolate HCV-JK046).

According to one embodiment of the invention, NS3 and/or NS4 and/or NS5b originate from viruses of different genotypes. For example, the NS3/NS4 polyprotein and the NS5b polypeptide can originate from viruses of different genotypes, e.g. NS3/NS4 originating from a genotype 1b and NS5b form a genotype 4 or vice versa.

According to another embodiment, NS3 and/or NS4 and/or NS5b originate from viruses of the same genotype, preferably of genotype 1b. A preferred embodiment of the present invention is directed to a peptide composition comprising a polyprotein NS3/NS4 as well as a polypeptide NS5b originating from the genotype 1b HCV JA strain (Kato et al., 1990, Proc. Natl. Acad., Sci. 87, 9524-9528). More preferably, the polyprotein NS3/NS4 comprises, or alternatively consists essentially or alternatively consists of the amino acid sequence shown in SEQ ID NO: 2 and/or the NS5b polypeptide comprises or alternatively consists essentially or alternatively consists of the amino acid sequence shown in SEQ ID NO: 4.

The polyprotein NS3/NS4 and the polypeptide NS5b contained in the peptide composition of the invention can be either of native origin, or of recombinant origin.

The polyprotein NS3/NS4 and the polypeptide NS5b of native origin are obtained from HCV strains or isolates, by means of the use of synthetic oligonucleotide primers that will serve to amplify the native viral sequences, either from sera of patients infected by the targeted viral genotype or genotypes, or from already purified viral RNA, originating for example from patients' blood or liver, or from complementary DNA that is free or cloned beforehand in an expression vector, or also from viral particles purified from biological samples or in vitro propagation system.

The polyprotein NS3/NS4 and the polypeptide NS5b of the invention of recombinant origin can also be obtained by the genetic engineering technique, which comprises the steps of:
culture of a microorganism or of eukaryotic cell(s) transformed using a nucleotide sequence coding for said polyprotein NS3/NS4 or for said polypeptide NS5b and recovery of the peptide produced by said microorganism or said eukaryotic cells.

This technique is well known to a person skilled in the art. For more details concerning this, reference can be made to the following work: Recombinant DNA Technology I, Editors Ales Prokop, Raskesh K Bajpai; Annals of the New-York Academy of Sciences, Volume 646, 1991.

The nucleotide sequences coding for the polyprotein NS3/NS4 and the polypeptide NS5b can be prepared by chemical synthesis in conjunction with a genetic engineering approach or by genetic engineering alone, using the techniques well known to a person skilled in the art and described for example in Sambrook J. et al., Molecular Cloning: A Laboratory Manual, 1989.

The nucleotide sequences coding for the polyprotein NS3/NS4 and the polypeptide NS5b can be inserted into expression vectors in a suitable expression system, in order to obtain the peptide composition of the invention.

The term "expression vector" as used herein refers to viral as well as non viral vectors, including extrachromosomal vectors (e.g. multicopy plasmids) and integrating vectors designed for being incorporated into the host chromosome(s). Particularly important in the context of the invention are vectors for use in gene therapy which are capable of delivering the NS3/NS4 and NS5b-encoding nucleotide sequences to a host organism as well as expression vectors for use in various expression systems. When referring to a "viral vector", this term encompasses any vector that comprises at least one element of viral origin, including a complete viral genome, a portion thereof or a modified viral genome as described below as well as viral particles generated thereof (e.g. viral vector packaged into a viral capsid to produce infectious viral particles).

Of course, the nucleotide sequences can be inserted into a single expression vector or into two different expression vectors. In the latter case, the sequence coding for the polyprotein NS3/NS4 is inserted into one of the two vectors and the sequence coding for the polypeptide NS5b is inserted into the other vector, these two vectors being either identical or different in nature.

Thus, another object of the invention is the expression vector(s) comprising a nucleotide sequence coding for the polyprotein NS3/NS4 and a nucleotide sequence coding for the polypeptide NS5b, as well as the means necessary to its expression.

By means necessary to the expression of a peptide is meant, the term peptide being used for any peptide molecule, such as protein, polyprotein, polypeptide, etc., any means that make it possible to obtain the peptide, such as in particular a promoter, a transcription terminator, a replication origin and preferably a selection marker.

The means necessary to the expression of a peptide are operationally linked to the nucleotide sequence coding for the peptide of interest. By "operationally linked", is meant a juxtaposition of said elements necessary to the expression and of the gene coding for the peptide of interest, which are in a relationship such that it is possible for them to function in an expected manner. For example, additional bases can exist between the promoter and the nucleotide sequence to the extent that their functional relationship is preserved.

The means necessary to the expression of a peptide can be homologous means, i.e. included in the genome of the vector used, or be heterologous. In the latter case, said means are cloned with the peptide of interest to be expressed.

Examples of heterologous promoters include (i) the viral promoters such as the SV40 promoter (simian virus 40), the promoter of the thymidine-kinase gene of the herpes simplex virus (TK-HSV-1), the LTR of the Rous sarcoma virus (RSV), the immediate first promoter of the cytomegalovirus (CMV), the adenovirus major last promoter (MLP), as well as (ii) any cell promoter that controls the transcription of the genes coding for peptides in upper eukaryotes, such as the constitutive promoter of the diphosphoglycerate-kinase gene (PGK) (Adra et al., 1987, Gene, 60: 65-74), the promoter of the liver-specific alpha-1 antitrypsin and FIX genes and the SM22 promoter specific to the smooth muscle cells (Moessler et al., 1996, Development, 122: 2415-2425).

According to one embodiment of the invention, the nucleotide sequences coding for said polyprotein NS3/NS4 and said polypeptide NS5b originate from different genotypes.

According to another embodiment, the nucleotide sequences coding for said polyprotein and said polypeptide originate from a virus of the same genotype, preferably genotype 1b. In a preferred embodiment, the nucleotide sequence which encodes the polyprotein NS3/NS4 comprises or alternatively consists essentially of, or alternatively consisting of the sequence as shown in SEQ ID NO: 1 and the nucleotide sequence which encodes the polypeptide NS5b comprises or alternatively consists essentially of, or alternatively consists of a sequence as shown in SEQ ID NO: 3.

Here too, by "nucleotide sequence" is meant all the sequences coding for the native polyprotein NS3/NS4 and the native polypeptide NS5b, as well as for their analogues, muteins and homologues, as defined previously.

Said sequences contained in the expression vector can be directly interlinked under the control of a single promoter and/or of a single expression-regulating element, or they can be separate, each being dependent on expression promoters and/or regulators that are independent identical or different.

As expression vectors that are suitable for the purposes of the invention, there can be mentioned for example plasmids, adenovirus-type viral vectors, poxviruses, vaccinia viruses, baculoviruses, *salmonella*-type bacterial vectors, BCG.

Adenoviruses have been detected in numerous animal species, do not integrate and are only slightly pathogenic. They are capable of infecting a variety of cell types, cells in division and cells at rest. They possess a natural tropism for the bronchial epithelia. Moreover, they have been used as live enteric vaccines for many years with an excellent safety profile. Finally, they can easily be made to grow and be purified in large amounts. These characteristics have meant that the adenoviruses are particularly appropriate for use as expression vectors and in particular as gene therapy vectors for therapeutic purposes and for vaccines.

According to a preferred embodiment, the vector of the invention is an adenovirus.

Examples of adenoviruses to be used in the present invention can be derived from any source of human or animal origin, in particular of canine origin (for example CAV-1 or CAV-2; reference Genbank CAV1GENOM and CAV77082 respectively), of avian origin (reference Genbank AAVEDS-DNA), of bovine origin (such as BAV3, Seshidhar Reddy et al., 1998, J. Virol., 72: 1394-1402), of ovine, feline, porcine origin, of simian origin, or from one of their hybrids. Any serotype can be used. However, adenoviruses of human origin are preferred and in particular adenovirus 5 (Ad5), adenovirus-2 (Ad2) and adenovirus-35 (Ad35).

Generally, the mentioned viruses are available from the ATCC collections and have been the subject of numerous publications describing their sequence, their organization and their biology, which allows a person skilled in the art to use them easily. For example, the sequence of the adenovirus type 5 is described in the Genbank database (M73260 and M29978) and is incorporated here by way of reference.

The genome of the adenovirus is constituted by a double-strand linear DNA molecule of approximately 36 kb carrying more than approximately 30 genes necessary for terminating the viral cycle. The first genes are divided into 4 regions dispersed in the genome of the adenovirus (E1 to E4). The E1, E2 and E4 regions are essential for viral replication. The E3 region is considered as a non-essential region on the basis of the observation that mutant viruses appear naturally or the hybrid viruses having lost this E3 region continue to replicate like wild-type viruses in cultured cells (Kelly and Lewis, 1973, J. Virol., 12: 643-652). The late genes (L1 to L5) mostly code for the structural proteins constituting the viral capsid. They overlap at least in part the first transcription units and are transcribed from a single promoter (MLP for Major Late Promoter). Moreover, the adenoviral genome carries at the two ends of the cis-acting regions essential for DNA replication, the 5' and 3' inverted terminal repeats (ITRs) and a packing sequence respectively.

The adenoviruses currently used in gene therapy protocols are stripped of the majority of the E1 region, which renders the viruses deficient at the level of their replication in order to avoid their dissemination in the environment and in the host organism. Moreover, most of the adenoviruses are also stripped of the E3 region in order to increase their cloning capacity. The feasibility of gene transfer using these vectors has been demonstrated in a variety of tissues in vivo (see for example Yei et al., 1994, Hum. Gene Ther., 5: 731-744; Dai et al., 1995, Proc. Natl. Acad. Sci. USA, 92: 1401-1405; U.S. Pat. No. 6,099,831; and U.S. Pat. No. 6,013,638).

Preferably, the promoters used in the adenoviruses as expression vectors are heterologous promoters such as the CMV and SV40 promoters.

Preferably also, the CMV promoter is the promoter of the polyprotein NS3/NS4 and the expression vector comprises as nucleotide sequence coding for said polyprotein the expression cassette CMV-NS3-NS4.

By "expression cassette", is meant a DNA sequence containing a promoter and an open reading frame for the expression of the peptide of interest, to be inserted into a vector.

Preferably also, the SV40 promoter is the promoter of the polypeptide NS5b and the expression vector comprises as nucleotide sequence coding for said polypeptide the expression cassette SV40-NS5b.

According to one embodiment of the invention, the genome of the adenovirus is modified so as to replace the E1 region by the expression cassette CMV-NS3-NS4 and to replace the E3 region by the expression cassette SV40-NS5b.

The methods of suppression and of insertion of DNA sequences into expression vectors are widely known to a person skilled in the art and consist in particular of steps of enzymatic digestion and ligation or homologous recombination (Chartier et al., 1996, J. Virol. 70, 4805-4810).

Another expression vector particularly appropriate for the purposes of the invention is a poxvirus, which constitutes another embodiment of the invention.

The poxviruses constitute a group of enveloped complex viruses, differing principally in their unusual morphology, their large DNA genome and their cytoplasmic replication site. The genome of several elements of the *poxviridae*, comprising the Copenhagen strain of the vaccinia virus (VV) (Goebel et al., 1990, Virol. 179: 247-266 and 517-563) and the modified vaccinia virus Ankara (MVA) strain (Antoine et al., 1998, Virol., 244: 635-396), has been mapped and sequenced. The VV strain possesses a double-strand DNA genome of approximately 192 kb coding for approximately 200 proteins approximately 100 of which are involved in the assembly of the virus. The MVA strain is a highly attenuated strain of vaccinia virus, generated by more than 500 passages in series of the vaccinia virus Ankara strain (CVA) over chicken embryo fibroblasts (Mayr et al., 1975, Infection, 3: 6-16). The MVA virus has been deposited in the Collection Nationale de Cultures de Microorganismes (CNCM) under Number I-721. The determination of the complete sequence of the MVA genome and comparison with that of the W allows precise identification of the alterations that have appeared in the viral genome and the definition of seven deletions (I to VII) and of numerous mutations leading to fragmented open reading frames (Antoine et al., 1998, Virology, 244: 365-396).

Other examples of poxviruses that are appropriate for the purposes of the invention include duck pox, fowl pox, cow pox, entomopox, monkey pox, swine pox and penguin pox.

The poxvirus is found in two morphologically distinct forms, called intracellular mature virus (IMV) and enveloped extracellular virus (EEV).

The poxvirus used as an expression vector of the invention has at least one of the following characteristics, taken alone or in combination:
   (i) the poxvirus is an MVA virus,
   (ii) the poxvirus is in the IMV morphological form, and
   (iii) the genome of the poxvirus is modified so as to insert the expression cassette NS3/NS4 and to insert the expression cassette NS5b.

Preferably, the promoters used in poxvirus vectors as expression vectors are homologous promoters (e.g. from poxvirus origin). Representative examples include without limitation the vaccinia promoters 7.5K, H5R, TK, p28, p11 and K1L, chimeric promoters between early and late poxyiral promoters as well as synthetic promoters such as those described in Chakrabarti et al. (1997, Biotechniques 23, 1094-1097), Hammond et al. (1997, J. Virological Methods 66, 135-138) and Kumar and Boyle (1990, Virology 179, 151-158). When the genome of the poxvirus is modified so as to insert the two cassettes of interest, the means necessary to their expression are both homologous. Thus, in the case where the MVA virus is used, the expression of NS3/NS4 can be for example under the control of the promoter ph5r so that the corresponding expression cassette is ph5r-NS3-NS4, and the expression of NS5b can be for example under the control of the promoter p7.5 so that the corresponding expression cassette is p7.5-NS5b, and vice versa. The expression cassettes can be inserted at the same or at different location in the poxvirus genome. In a preferred embodiment, the expression cassettes are both inserted in deletion II or in deletion III of a MVA genome, with a special preference for deletion III.

According to a particular embodiment, when the genome of the poxvirus is modified so as to insert the two cassettes of interest, the two said expression cassettes are oriented in the same direction.

According to another particular embodiment, they are oriented in the opposite direction.

Here too, the expression cassettes are inserted into the genome of the poxvirus in a manner known to a person skilled in the art, as indicated previously.

The vectors of the invention can also comprise sequences necessary for targeting peptides towards particular cell compartments. An example of targeting can be the targeting towards the endoplasmic reticulum obtained using address sequences of the leader sequence type originating from the protein E3 of the adenovirus (Ciernik I. F., et al., The Journal of Immunology, 1999, 162, 3915-3925).

They can also comprise sequences necessary for targeting towards the dendritic cells and for targeting at the membrane of the cells.

An object of the invention is also the microorganisms and the eukaryotic cells transformed by an expression vector of the invention.

By way of examples of microorganism that are suitable for the purposes of the invention, there can be mentioned the yeasts, such as those of the following families: *Saccharomyces, Schizosaccharomyces, Kluveromyces, Pichia, Hanseluna, Yarrowia, Schwantomyces, Zygosaccharomyces, Sac-* charomyces cerevisiae, Saccharomyces pombe Saccharomyces carlsbergensis, Pichia pastoris and Kluveromyces lactis being preferred; and the bacteria, such as *E. coli* and those of the following families: *Lactobacillus, Lactococcus, Salmonella, Streptococcus, Bacillus* and *Streptomyces*.

By way of examples of eukaryotic cells, there can be mentioned cells originating from animals such as mammals, reptiles, insects and equivalent. They can be of a unique type of cells or a group of different types of cells and encompass cultured cell lines, primary cells and proliferative cells. The preferred eukaryotic cells are cells originating from the Chinese hamster (CHO cells), monkey (COS and Vero cells), baby hamster kidney (BHK cells), pig kidney (PK 15 cells) and rabbit kidney (RK13 cells), human osteosarcoma cell lines (143 B), HeLa human cell lines and the human hepatoma cell lines (Hep G2-type cells), as well as insect cell lines (for example of *Spodoptera frugiperda*).

The host cells can be provided in cultures in suspension or in flasks, in tissue cultures, organ cultures and equivalent. The host cells can also be transgenic animals.

Advantageously, the NS3/NS4 and/or the NS5b-encoding nucleotide sequence(s) can independently be optimized for providing high level expression in a particular host cell, e.g. mammalian, yeast or bacterial host cells. It has been indeed observed that, when more than one codon is available to code for a given amino acid, the codon usage patterns of organisms are highly non-random (see for example Wada et al., 1992, Nucleic Acids Res. 20, 2111-2118) and may be markedly different between different hosts (see for example Nakamura et al., 1996, Nucleic Acids Res. 24, 214-215). Thus, nucleotide sequences of viral origin (HCV) may have an inappropriate codon usage pattern for efficient expression in host cells, especially bacterial or yeast cells. Typically, codon optimisation is performed by replacing one or more "native" (e.g. HCV) codon corresponding to a codon infrequently used in this particular host cell by one or more codon encoding the same amino acid which is more frequently used. This can be achieved by conventional mutagenesis or by chemical synthetic techniques (e.g. resulting in a synthetic nucleic acid molecule). It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleotide sequence.

Further to optimization of the codon usage, expression in the host cell can further be improved through additional modifications. For example, the NS3/NS4 and/or NS5b-encoding nucleotide sequence can be modified so as to prevent clustering of rare, non-optimal codons being present in concentrated areas and/or to suppress or modify at least partially negative sequence elements which are expected to negatively influence expression levels (e.g. AT-rich or GC-rich sequence stretches; unstable direct or inverted repeat sequences; RNA secondary structures; and/or internal cryptic regulatory elements such as internal TATA-boxes, chi-sites, ribosome entry sites, and/or splicing donor/acceptor sites).

The invention also relates to antibodies directed against one of the peptide compositions of the invention as defined previously or against one of the expression vectors of the invention as defined previously.

The antibodies according to the invention are either polyclonal or monoclonal antibodies.

The abovementioned polyclonal antibodies can be obtained by immunization of an animal with the peptide composition of the invention or with the vector of the invention as "antigen of interest", followed by the recovery of the antibodies sought in purified form, by sampling the serum of said animal, and separation of said antibodies from the other constituents of the serum, in particular by affinity chromatography on a column to which is fixed an antigen specifically recognized by the antibodies, in particular a viral antigen of interest.

The monoclonal antibodies can be obtained by the hybridomas technique the general principle of which is recalled hereafter.

In a first step, an animal, generally a mouse, (or cells in culture within the framework of in vitro immunizations) is immunized with the peptide composition of the invention or with the vector of the invention as "antigen of interest", the B lymphocytes of which are then capable of producing antibodies against said antigen. These antibody-producing lymphocytes are then fused with "immortal" myelomatous cells (murine in the example) in order to produce hybridomas. From the thus-obtained heterogeneous mixture of cells, a selection is then made of cells capable of producing a particular antibody and multiplying indefinitely. Each hybridoma is multiplied in clone form, each leading to the production of a monoclonal antibody the recognition properties of which vis-à-vis the antigen of interest can be tested for example by ELISA, by immunotransfer in one or two dimensions, by immunofluorescence, or using a biocaptor. The monoclonal antibodies thus selected are subsequently purified in particular according to the affinity chromatography technique described above.

The peptide compositions, the expression vectors, the nucleotide sequences coding for said polyprotein NS3/NS4 and said polypeptide NS5b, as well as the antibodies of the invention are particularly effective for the inhibition, prevention and control of the infection of patients carrying the HCV virus, so that their use for the preparation of a medicament constitutes another object of the invention.

The present invention also relates to a pharmaceutical composition, in particular a vaccine, containing as active ingredient the peptide composition of the invention, or an expression vector of the invention, or an expression vector comprising a nucleotide sequence coding for the polyprotein NS3/NS4 with an expression vector comprising a nucleotide sequence coding for the polypeptide NS5b, or the nucleotide sequences coding for said polyprotein NS3/NS4 and said polypeptide NS5b, said nucleotide sequences corresponding to the sequences contained in the expression vectors of the invention, placed under the control of elements necessary to an expression constitutive of and/or inducible from said peptides, or at least one of the antibodies of the invention.

By elements necessary to an expression constitutive of the peptides, is meant a promoter that is ubiquitous or specific to the eukaryotic cells.

As elements necessary to an expression inducible from the peptides, there can be mentioned the elements of regulation of the operon of *E. coli* for tetracycline resistance (Gossen M. et al., Proc Natl Acad Sci USA, 89: 5547-5551 (1992).

According to a particular embodiment of the invention, the pharmaceutical composition also contains a pharmaceutically appropriate vehicle. Of course, a person skilled in the art will easily determine the nature of the pharmaceutically appropriate vehicle and the quantity of active ingredient to be used as a function of the constituents of the pharmaceutical composition.

The quantity and nature of the pharmaceutically appropriate vehicle can be easily determined by a person skilled in the art. They are chosen according to the desired pharmaceutical form and method of administration.

In addition, the pharmaceutical composition of the invention may comprise one or more adjuvant(s) suitable for systemic or mucosal application in humans. Preferably, the adjuvant is capable of stimulating immunity against an HCV protein or one epitope, especially a T cell-mediated immunity. Representative examples of suitable adjuvants, especially for use in combination with the peptide composition of the invention, include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p 407-419), saponins such as QS21 (Sumino et al., 1998, J. Virol. 72, 4931-4939; WO 98/56415), imidazo-quinoline compounds such as Imiquimod (Suader, 2000, J. Am Acad Dermatol. 43, S6-S11) and related compound S-27609 (Smorlesi, 2005, Gene Ther. 12, 1324-1332), cytosine phosphate guanosine oligodeoxynucleotides such as CpG (Chu et al., 1997, J. Exp. Med. 186: 1623; Tritel et al., 2003, J. Immunol. 171: 2358-2547) and cationic peptides such as IC-31 (Kritsch et al., 2005, J. Chromatogr Anal. Technol Biomed Life Sci 822, 263-270).

The pharmaceutical compositions of the invention are appropriate for oral, sublingual, sub-cutaneous, intramuscular, intravenous, topical, local, intratracheal, intranasal, transdermal, rectal, intraocular, intra-auricular administration, said active ingredient being able to be administrated in a unitary dosage form of administration.

The unitary dosage forms of administration can be for example tablets, gelatin capsules, granules, powders, solutions or injectable, oral suspensions, transdermal patches, forms of sublingual, buccal, intratracheal, intraocular, intranasal, intra-auricular or by inhalation administration, forms of topical, transdermal, sub-cutaneous, intramuscular or intravenous administration, forms of rectal administration, or implants. For topical administration, creams, gels, ointments, lotions or collyriums can be envisaged.

These galenic forms are prepared according to the usual methods of the fields considered.

Said unitary dosage forms are dosed in order to allow daily administration of 0.001 to 10 mg of active ingredient per kg of body weight, according to the galenic form.

There may be particular cases where higher or weaker dosages are appropriate; the scope of the invention is not exceeded by such dosages. According to usual practice, the dosage appropriate to each patient is determined by the doctor as a function of various parameters, in particular the method of administration, the age, weight and the response of the patient; the active ingredient employed; the nature and extent of symptoms; kind of concurrent treatment; the frequency of treatment; and/or the need for prevention or therapy. For general guidance, suitable dosage for adenovirus-comprising composition varies from approximately $10^5$ to approximately $10^{13}$ iu (infectious units), desirably from approximately $10^7$ to approximately $10^{12}$ iu and preferably from approximately $10^8$ to approximately $10^{11}$ iu. Suitable dosage for poxvirus-comprising composition varies from approximately $10^4$ to approximately $10^{10}$ pfu (plaque forming units), desirably from approximately $10^5$ to approximately $10^9$ and preferably from approximately $10^6$ to approximately $10^8$ pfu. A composition based on vector plasmids may be administered in doses of between 10 µg and 20 mg, advantageously from approximately 100 µg to approximately 2 mg. A peptide composition may be administered in one or more doses of between 10 ng and 20 mg, with a special preference for a dosage from approximately 0.1 µg to approximately 2 mg of the active ingredient per kg body weight. The administration may take place in a single dose or a dose repeated one or several times after a certain time interval.

The pharmaceutical compositions of the invention preferably contain as active ingredient one of the vectors of the invention or an expression vector comprising a nucleotide sequence coding for the polyprotein NS3/NS4 with an expression vector comprising a nucleotide sequence coding for the polypeptide NS5b, so that they are useful in prophylactic and therapeutic vaccination.

Prophylactic and therapeutic vaccination can be implemented by injection of a vaccine based on one or more expression vectors of the invention, to the extent that the expression vector or vectors finally code for the polyprotein NS3/NS4 and for the polypeptide NS5b as active ingredient, said injection being or being not followed by boosters. It can also be implemented by injecting one or more doses of two different types of expression vectors of the invention, firstly an adenovirus to prime the host's immune response, then a poxvirus to boost the primed immune response, simultaneously or at different times, and vice versa (e.g. a poxvirus vector as a primer and an adenovirus vector as a booster).

These vectors can be contained in a pharmaceutical kit.

Also, another object of the invention is pharmaceutical kits, in particular vaccinal, comprising at least one expression vector comprising a nucleotide sequence coding for the polyprotein NS3/NS4 and at least one expression vector comprising a nucleotide sequence coding for the polypeptide NS5b.

Another object of the invention is pharmaceutical kits, in particular vaccinal, comprising at least one expression vector of adenovirus type as defined previously and/or at least one expression vector of poxvirus type as defined previously.

Prophylactic and therapeutic vaccination can also be implemented by injection of a vaccine based on at least one expression vector of the invention, or an expression vector comprising a nucleotide sequence coding for the polyprotein NS3/NS4 with an expression vector comprising a nucleotide sequence coding for the polypeptide NS5b, and at least one pharmaceutical composition of the invention constituted by the peptide composition of the invention or the antibodies of the invention. It can also be implemented by injection of a vaccine based on at least one expression vector of the invention, or an expression vector comprising a nucleotide sequence coding for the polyprotein NS3/NS4 with an expression vector comprising a nucleotide sequence coding for the polypeptide NS5b, and at least one nucleotide sequence coding for the polyprotein NS3/NS4 and for the polypeptide NS5b.

Also, another object of the invention is pharmaceutical kits, in particular vaccinal, comprising at least one expression vector of the invention, or an expression vector comprising a nucleotide sequence coding for the polyprotein NS3/NS4 with an expression vector comprising a nucleotide sequence coding for the polypeptide NS5b, and at least one pharmaceutical composition of the invention or at least one nucleotide sequence coding for the polyprotein NS3/NS4 and for the polypeptide NS5b.

Another object of the present invention relates to a method of treatment of one or more pathologies associated with an hepatitis C virus, which comprises at least one administration to a host organism of an effective dose of any of the above-described active ingredient (peptide composition, vector, antibodies and/or pharmaceutical composition of the invention) or any combination thereof. The present invention also provides the use of at least one of the above-described active ingredient or any combination thereof for the preparation of a medicament for treating one or more pathologies associated with a hepatitis C virus. The term "treatment" or "treating" as used herein encompasses prophylactic and therapeutic vaccination of a host organism infected with a hepatitis C virus. The term "host organism" is intended to encompass any mammal, such as any murine, rat, bovine, porcine, canine, feline, equine, monkey or human subject, for example a human infected with HCV.

The method or use of the present invention is especially useful for treating HCV persistent infection and liver cancer in HCV-infected patients. The term "cancer" encompasses any cancerous conditions including diffuse or localized tumors, metastasis, cancerous polyps as well as preneoplastic lesions (e.g. cirrhosis). Desirably, the effective dose of the peptide composition, vector, pharmaceutical composition and/or antibodies of the invention is such that it provides a therapeutic benefit to the host organism into which it is administrated. The therapeutic benefit can be evidenced by a number of ways, for instance a decrease of HCV viremia detected in blood, plasma or sera of the treated organism as compared to before treatment, and/or by the detection of an anti-HCV immune response (e.g. production of anti-HCV antibodies and/or T cell-mediated immunity) or by the delay of the symptoms associated with an HCV infection (e.g. delay in the development of liver cirrhosis or cancer), or by a decrease or slow down of liver inflammation/steatosis/fibrosis conditions typically associated with HCV infection or by an improved response of the individual to conventional therapies.

Preferably, the NS3/NS4 polyprotein and eventually the NS5b polypeptide comprised or encoded by the peptide composition, vector, and/or pharmaceutical composition of the invention originates from genotype 1b and is used according to the modality described herein for treating the pathologies associated with a genotype 1b hepatitis C virus. Alternatively, it originates from genotype 1b and is used according to the modality described herein for treating the pathologies associated with a genotype other than 1b, such as a genotype 1a, 3 or 4 hepatitis C virus with a special preference for genotype 1a.

If desired, the method or use according to the invention can be carried out in conjunction with one or more conventional therapeutic modalities (e.g. radiation, chemotherapy and/or surgery). In one embodiment, the method or use of the invention is associated to chemotherapy with one or more drugs which are conventionally used for treating or preventing HCV infections, HCV-associated pathologies. Representative examples of HCV drugs include without limitation antivirals, protease inhibitors (e.g. serine protease inhibitors such as VX950 of Vertex), polymerase inhibitors, helicase inhibitors, antifibrotics, nucleoside analogs, TLR agonists, N-glycosylation inhibitors, siRNA, antisense oligonucleotides, immune modulators, therapeutic vaccines and antitumor agents usually used in the treatment of HCV-associated hepatocarcinomas (e.g. adriamycin or a mixture of adriamycin lipiodol and spongel usually administered by chimioembolisation in the hepatic artery). Such HCV drugs can be provided in a single dose or, alternatively, in multiple doses according to standard protocols, dosages and regimens over several hours, days and/or weeks. Their administration may precede, be concomitant, or subsequent to the administration of the peptide composition, vector, pharmaceutical composition and/or antibody of the invention. A preferred combination includes treatment of the host organism with pegylated IFN-α2a or IFN-α2b (e.g. at a dose of 10 µg/week) eventually in combination with ribavirin (e.g. at 800 to 1200 mg/day) for 24 to 48 weeks, before, in parallel or subsequently to the method or use of the invention. The peptide composition, vector, pharmaceutical composition and/or antibody of the invention can also be administered in combination with other treatments designed to enhance immune responses, e.g. by co-administration with adjuvants or cytokines (or vectors encoding cytokines) as is well known in the art.

In another embodiment, the method or use of the invention is carried out according to an accelerated immunization schedule which comprises at least three (e.g. from 3 to 10) sequential administrations of the peptide composition, vector, pharmaceutical or composition of the invention. Preferably, the at least three sequential administrations, are independently separated by a period of time varying from 3 days to 10 days but no more than 15 days. The method or use of the invention preferably comprises three sequential administrations of the vector or pharmaceutical composition of the invention, each at approximately one week interval. Even more preferably the method or use of the invention comprises three sequential administrations by intramuscular route at approximately one week interval of a poxvirus expression vector (e.g. a NS3/NS4 and NS5B-encoding MVA) as defined above or the pharmaceutical composition comprising such a vector.

In still another embodiment, the method or use of the invention can further include at least one "recall" administration at the end of the at least three sequential administrations. The number of recall administration(s) can vary from one to 10 and the time interval between the latest of the first series of sequential administrations and the first recall administration is a matter of at least approximately 4 weeks. Advantageously, the method or use comprises three sequential administrations at approximately one week interval and one recall administration which takes place either approximately 4 weeks or 6 months after the latest of the at least three sequential administrations. Alternatively, the method or use of the invention comprises two recall administrations, the first being approximately 4 weeks and the second approximately 6 months after the latest of the first series of sequential administrations. The recall administration(s) may use the same as or a different active ingredient than the first series of sequential administrations and may use the same route or a different route of administration. According to one aspect, the recall administration(s) is/are made using the same active ingredient and by the same route as the first series of sequential administrations. A preferred method or use according to this aspect comprises three sequential administrations at approximately one week interval and one or two recall administration(s) approximately 4 weeks and/or approximately 6 months after the third sequential administration, all by intramuscular route and with a poxvirus expression vector (e.g. a NS3/NS4 and NS5B-encoding MVA) as defined above or the pharmaceutical composition comprising such a vector.

According to another aspect, the sequential administrations and the recall administration(s) can use different active ingredients and/or different routes of administration. For example, the at least three sequential administrations may be made by intramuscular route with a poxvirus expression vector (e.g. a NS3/NS4 and NS5B-encoding MVA) or the pharmaceutical composition comprising such a vector as defined above and the recall administration(s) by subcutaneous or intramuscular route with any prior art polypeptide comprising NS3, NS4 and/or NS5b such as the polypeptide described in European patent application No EP 06 36 0014.2.

Another object of the invention provides a method of stimulating a T cell-mediated immune response against an hepatitis C virus target protein which comprises the step of administering in a host organism at least one dose of the peptide composition, vector, pharmaceutical or composition of the invention so as to stimulate a host's T cell-mediated immune response.

The stimulated immune response is preferably a CD8+ T cell response, a CD4+ T cell response or both a CD8+ and a CD4+ T cell responses. Desirably, the T cell-mediated immune response stimulated by the method or use of the present invention permits to target at least one epitope located in a NS3, and/or a NS4 and/or a NS5B protein present in the infecting hepatitis C virus. Preferably, the T cell-mediated immune response provided by the method or use of the invention is specific for at least one HLA-B-restricted epitope and in particular at least one HLA-B7 epitopes located in the NS3 polypeptide of the infecting hepatitis virus. Alternatively or in combination, the stimulated T cell-mediated immune response is specific for at least one HLA-A2-restricted epitope and in particular at least one HLA-A2 epitope located in the NS3 and/or NS5b protein of the infecting hepatitis virus.

In a preferred embodiment, the method or use according to the invention is provided to the host organism according to the accelerated immunization schedule described above and comprises at least three sequential administrations of the peptide composition, vector, pharmaceutical or composition of the invention and optionally one or two recall administration(s).

Desirably, the stimulated T cell immune response is long-lasting and can be detected in the treated host organism for at least one month following the last administration of the peptide composition, vector, pharmaceutical or composition of the invention. Preferably, the stimulated immune response can be detected for at least 2 months, desirably for at least 3 months, and preferably for at least 6 months.

The ability of the method or use of the invention to stimulate an anti-HCV T cell-mediated immune response can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The method of the invention can also be further validated in animal models challenged with an appropriate infectious agent (e.g. a bacteria or a vaccinia virus expressing HCV genes) to determine neutralization of the infectious agent and eventually partial resistance to the associated symptoms, reflecting an induction or an enhancement of an anti-HCV cell immune response. Testing and validation of the vector compositions of the invention are also illustrated in the appended Example section.

Figure 1A:
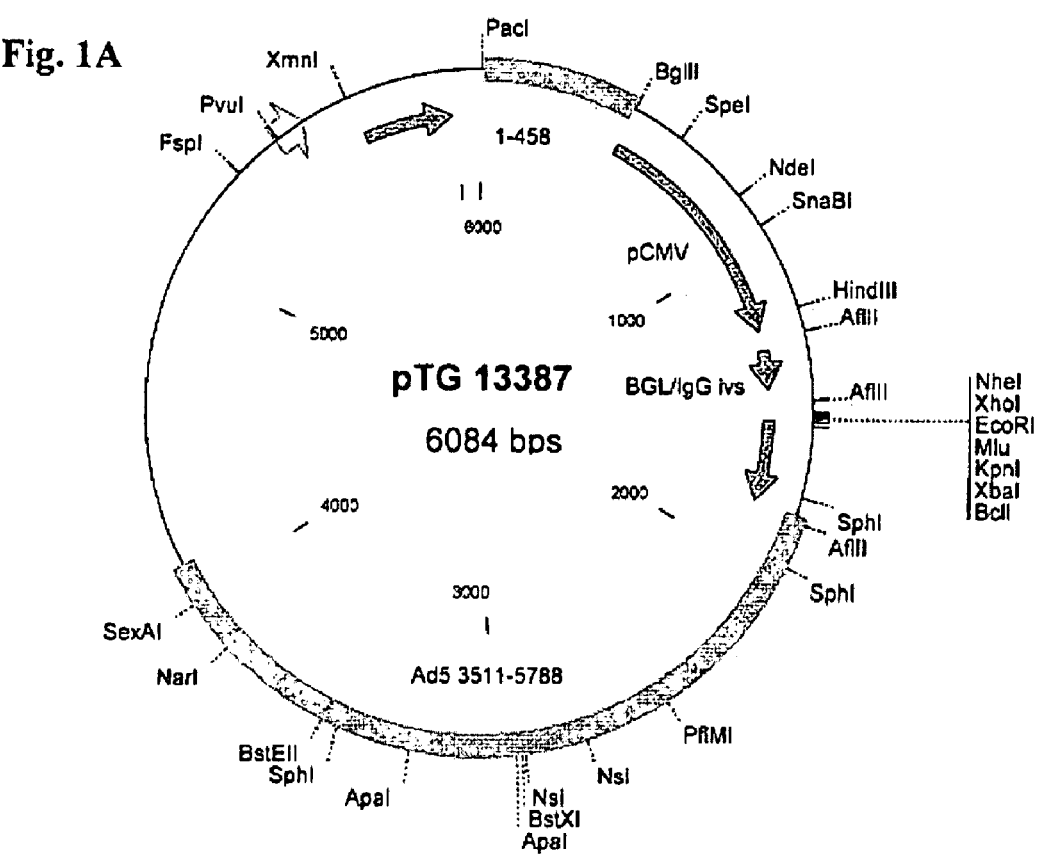
Figure 1B:
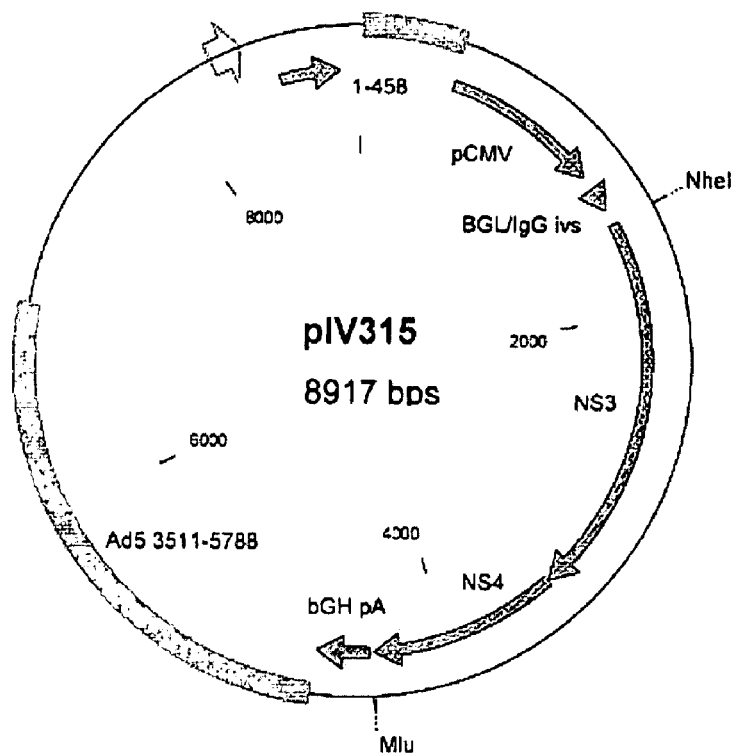
Figure 1C:
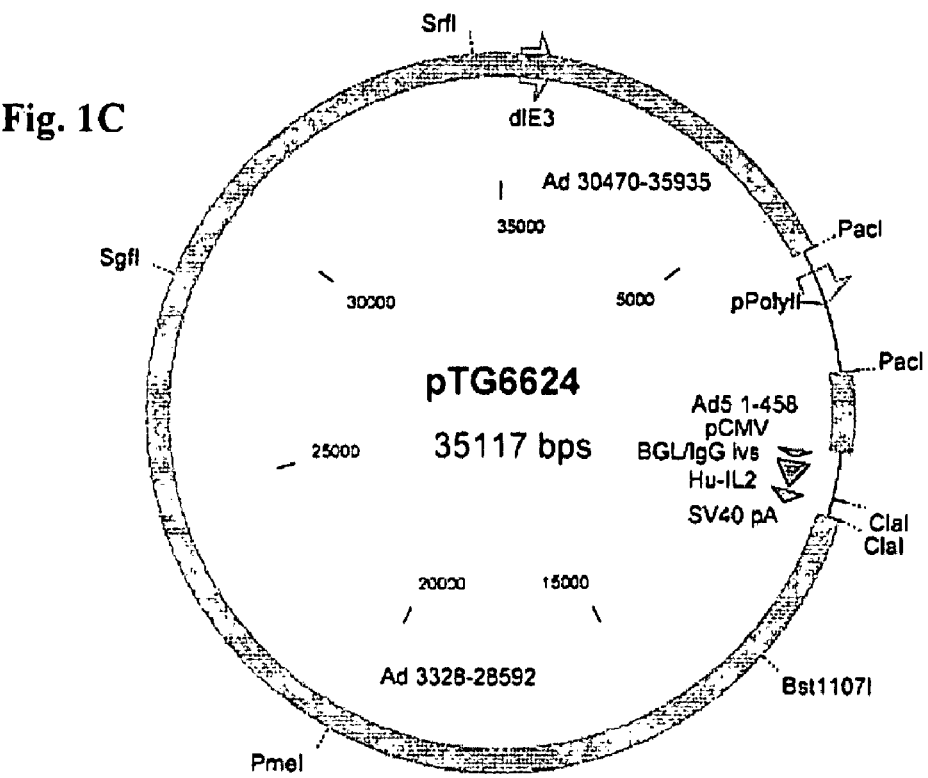
Figure 1D:
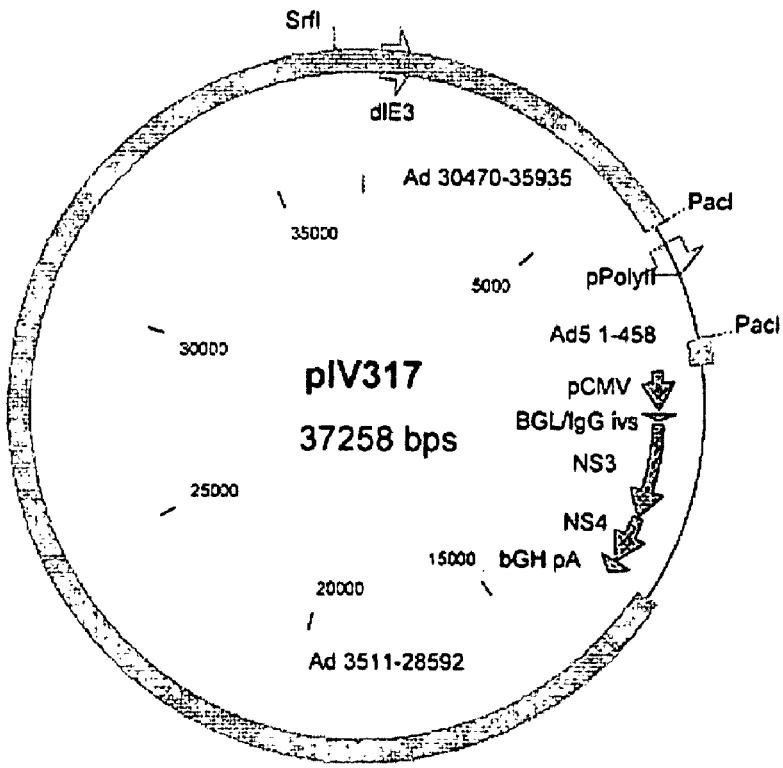
Figure 1E:
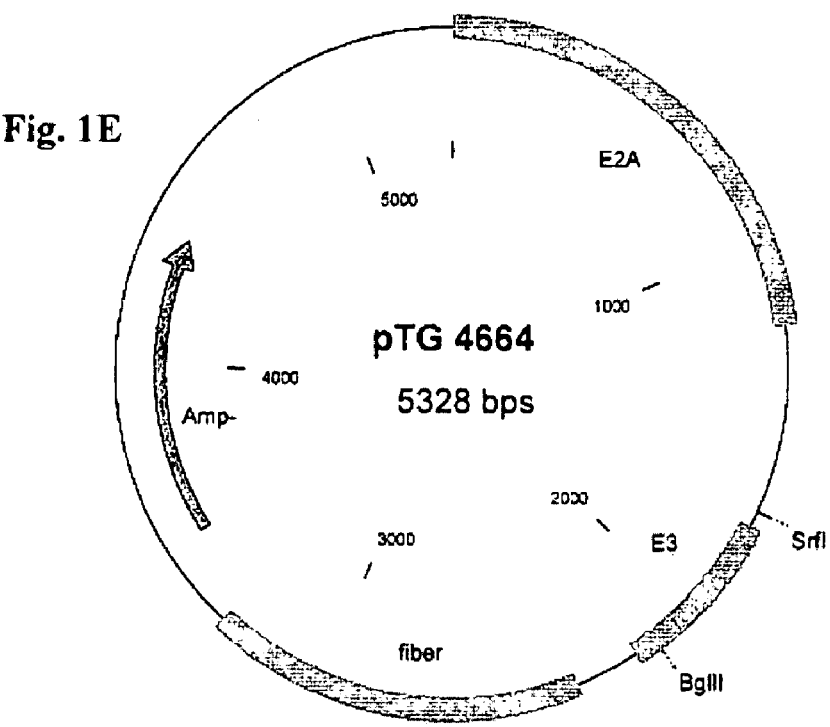
Figure 1F:
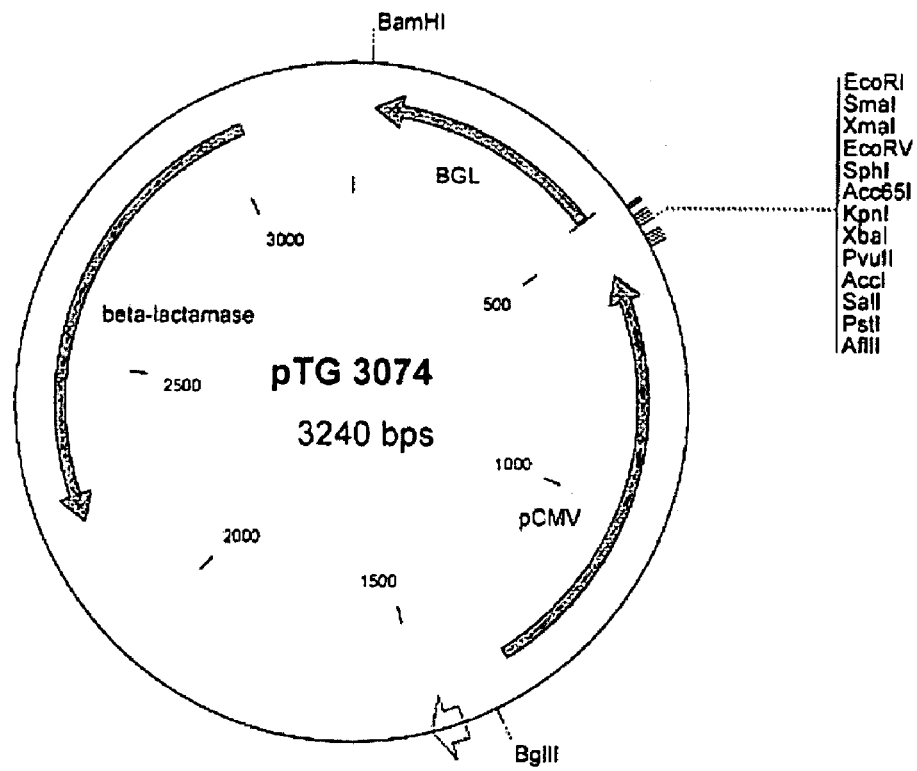
Figure 1G:
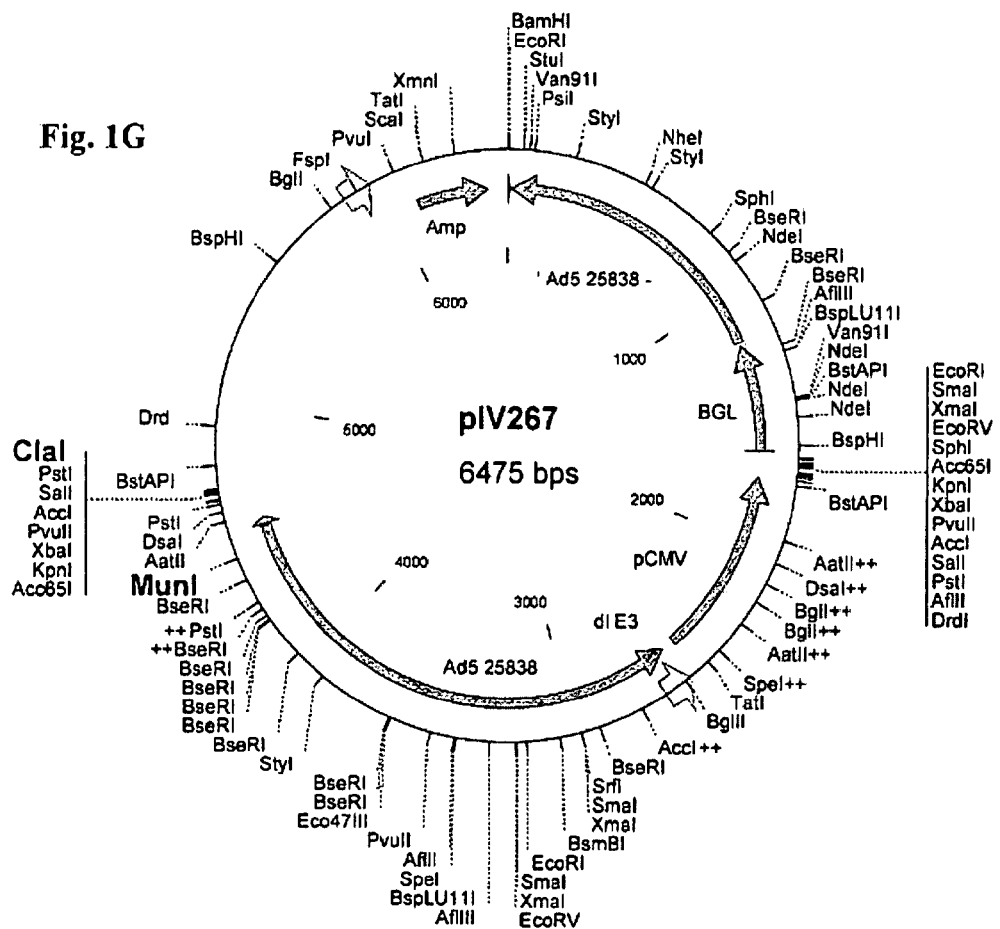
Figure 1H:
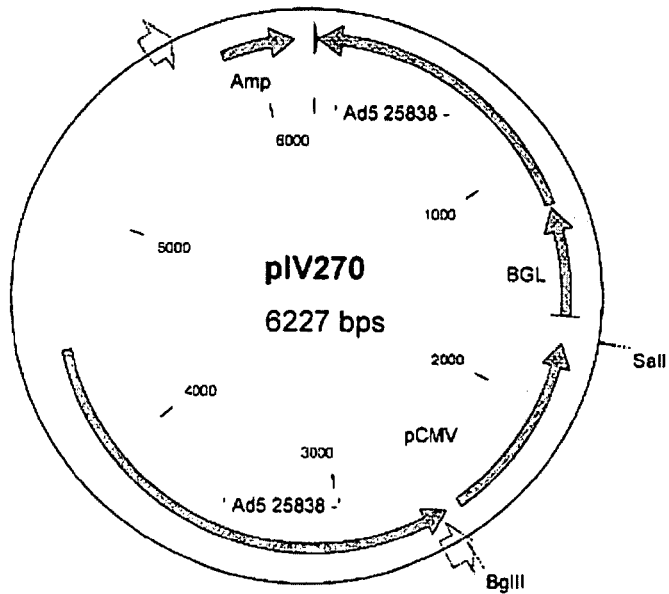
Figure 1:
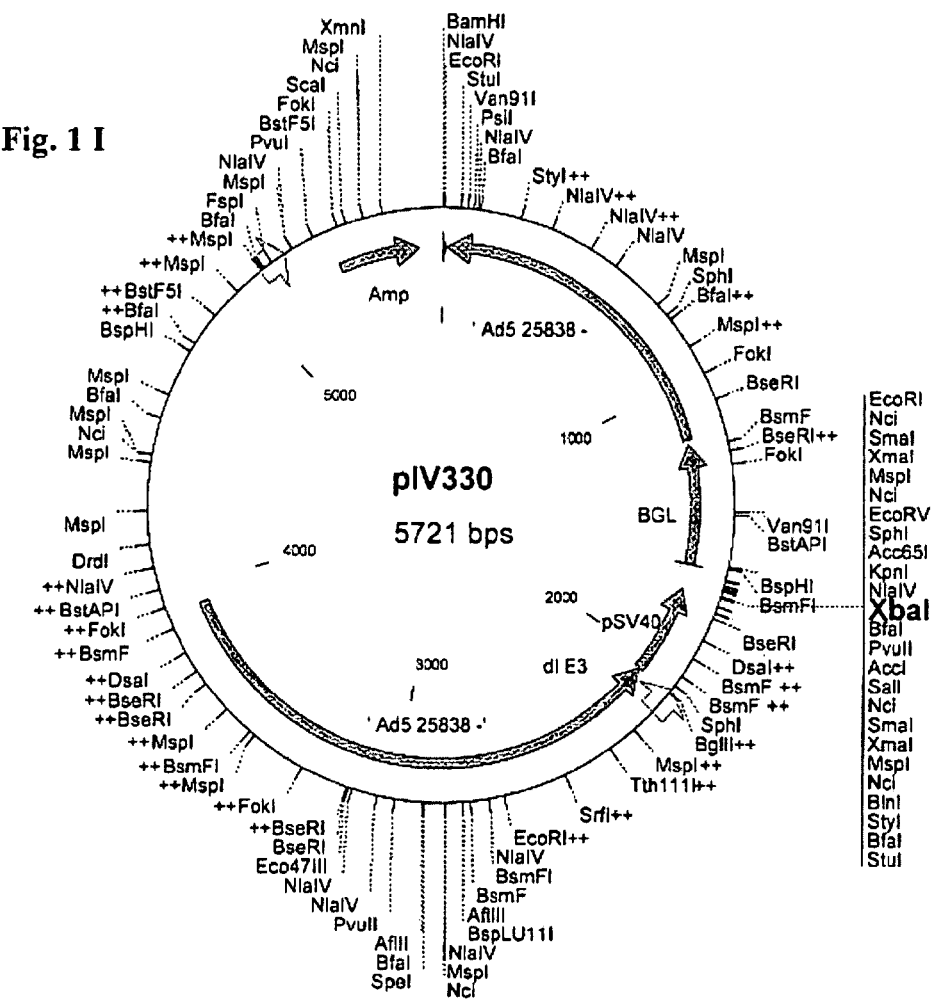
Figure 1:
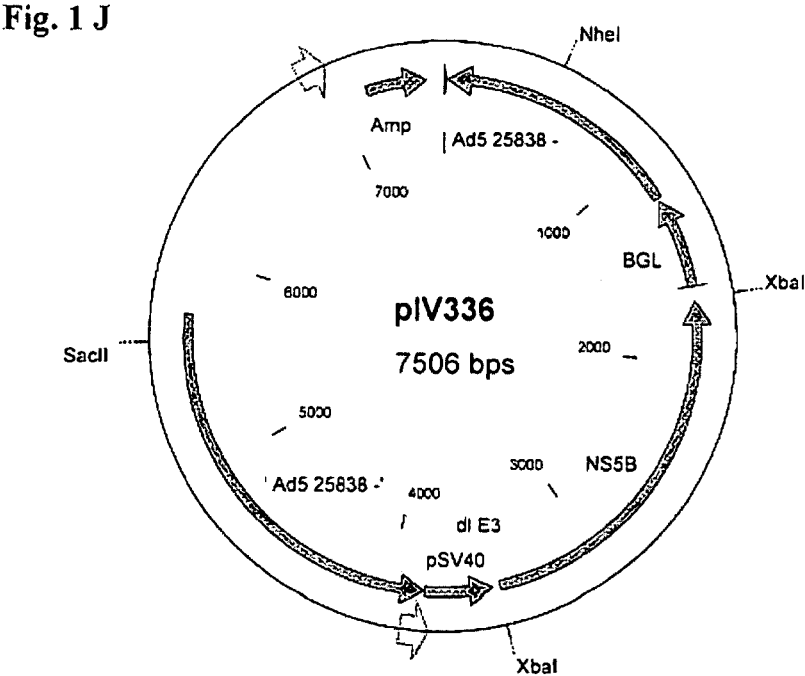
Figure 1K:
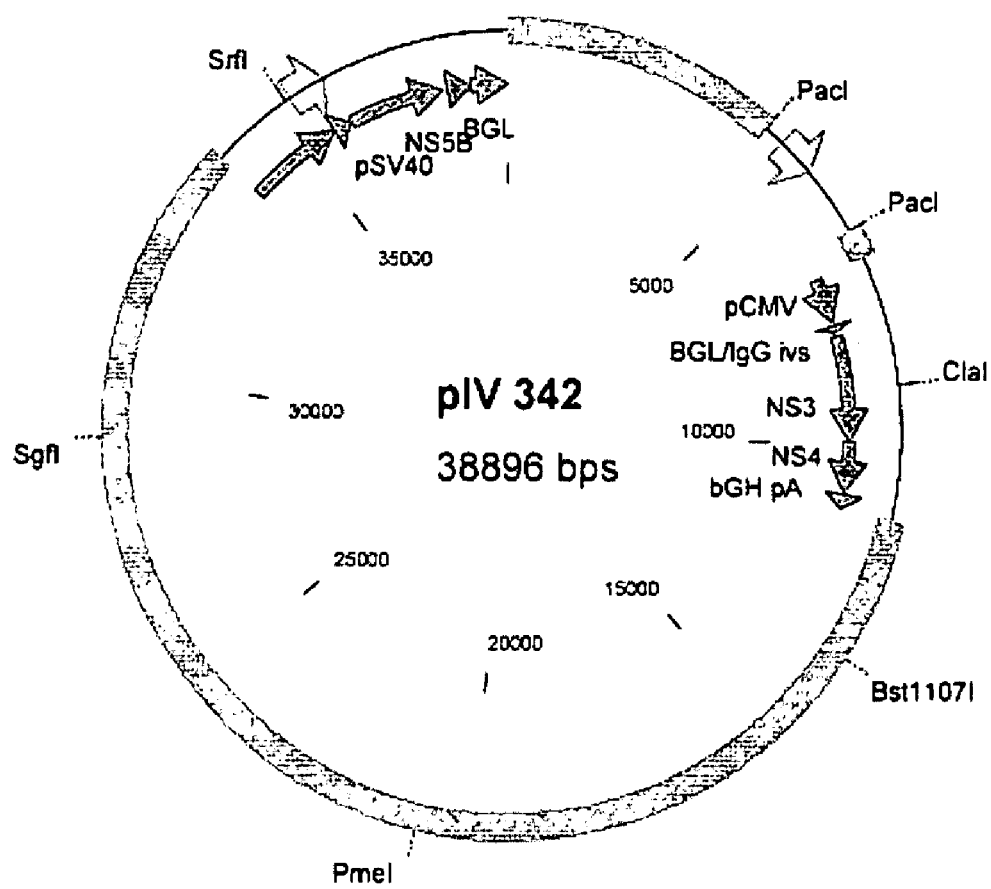
Figure 2A:
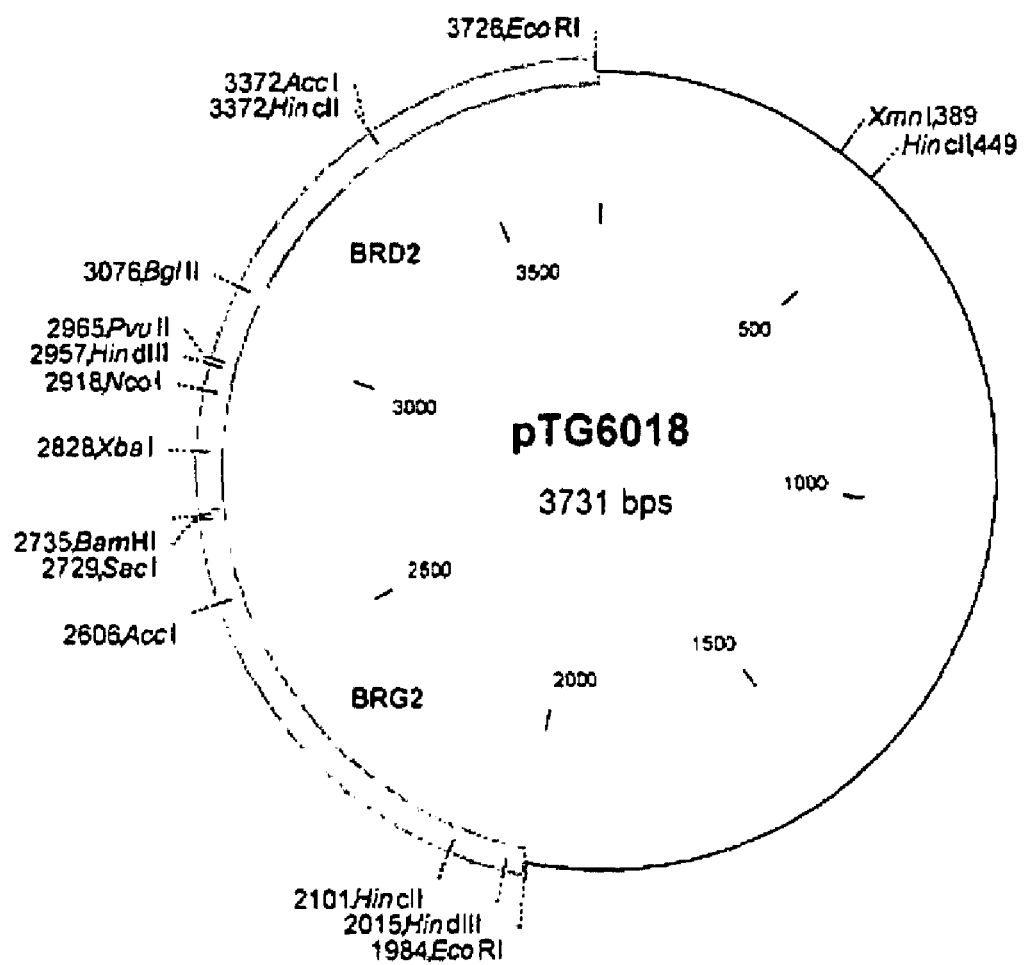
Figure 2B:
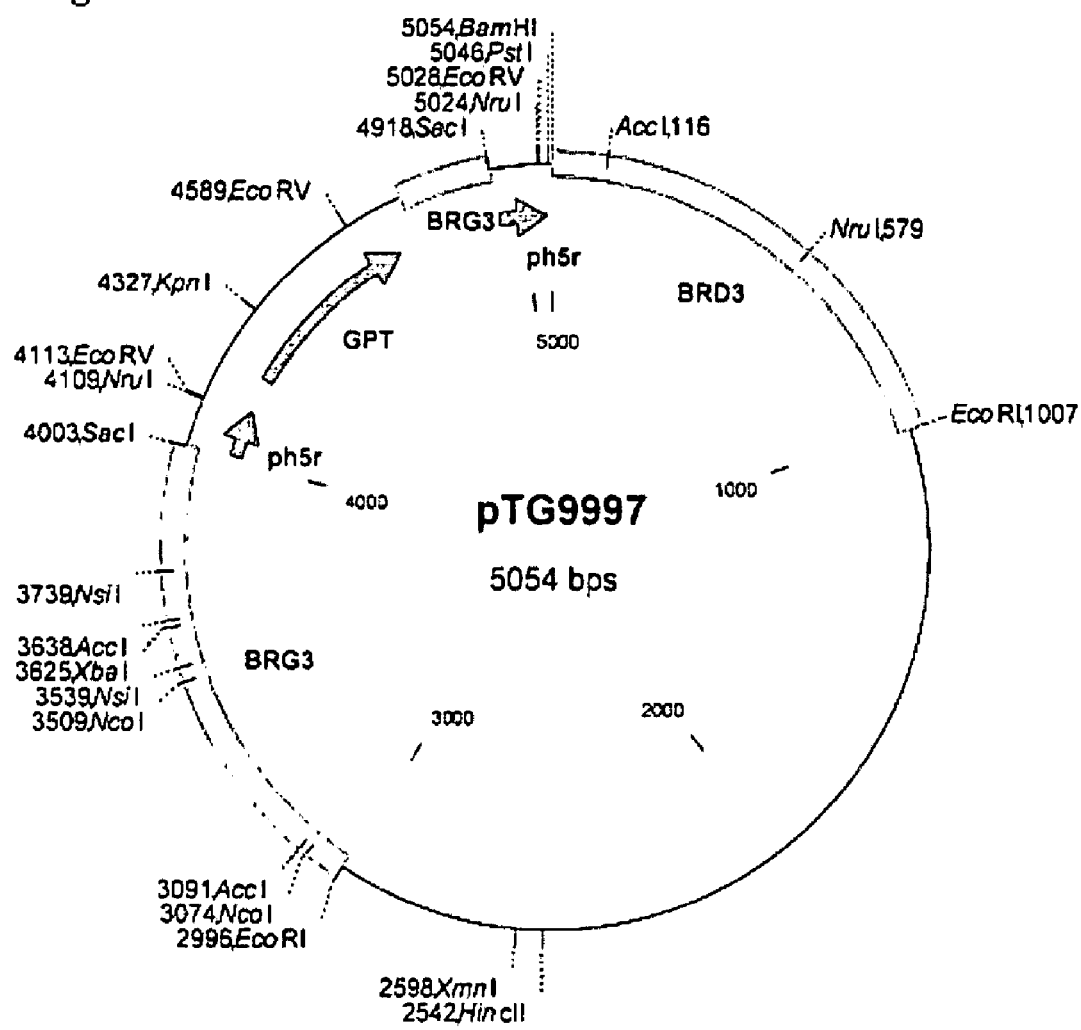
Figure 2C:
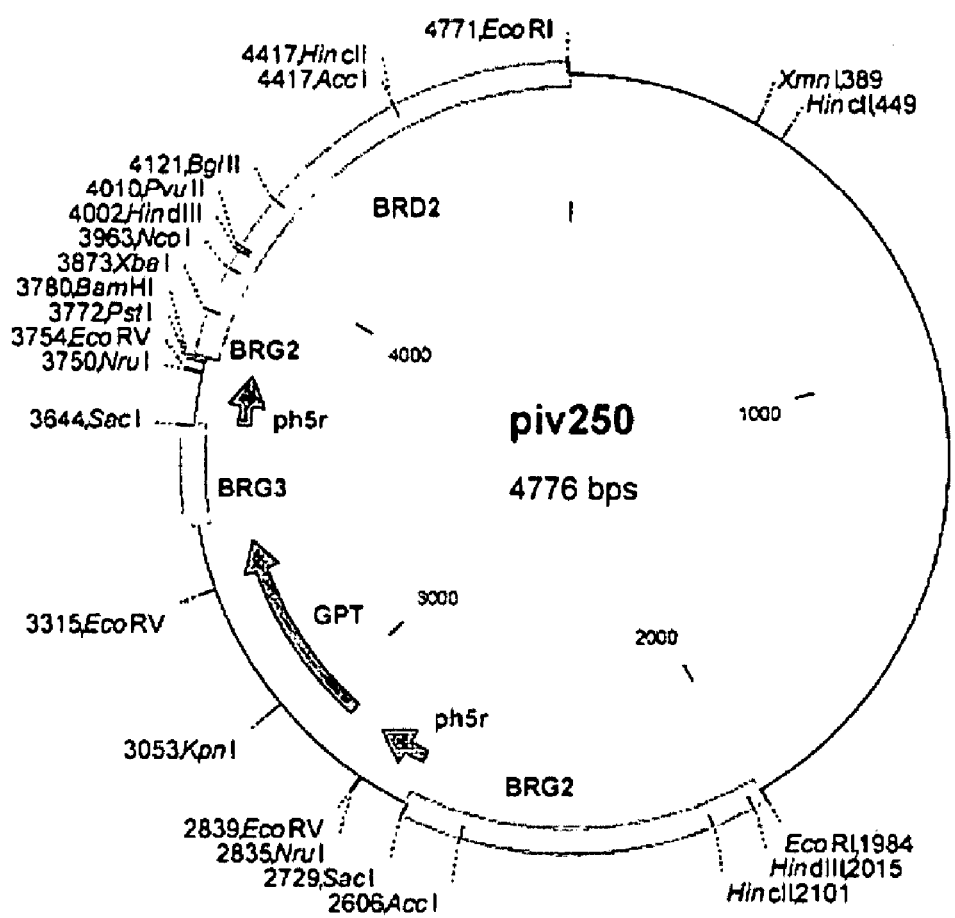
Figure 2D:
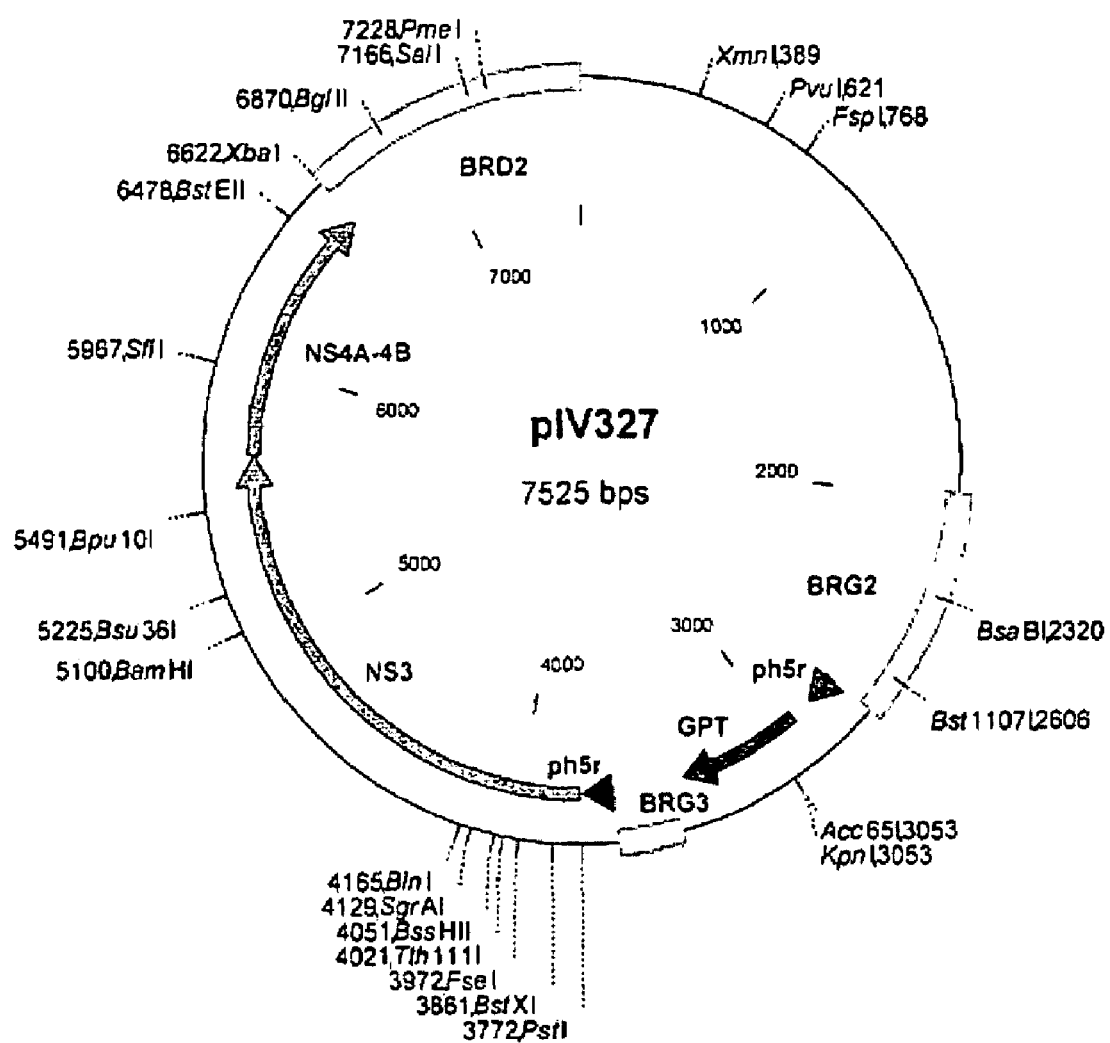
Figure 2E:
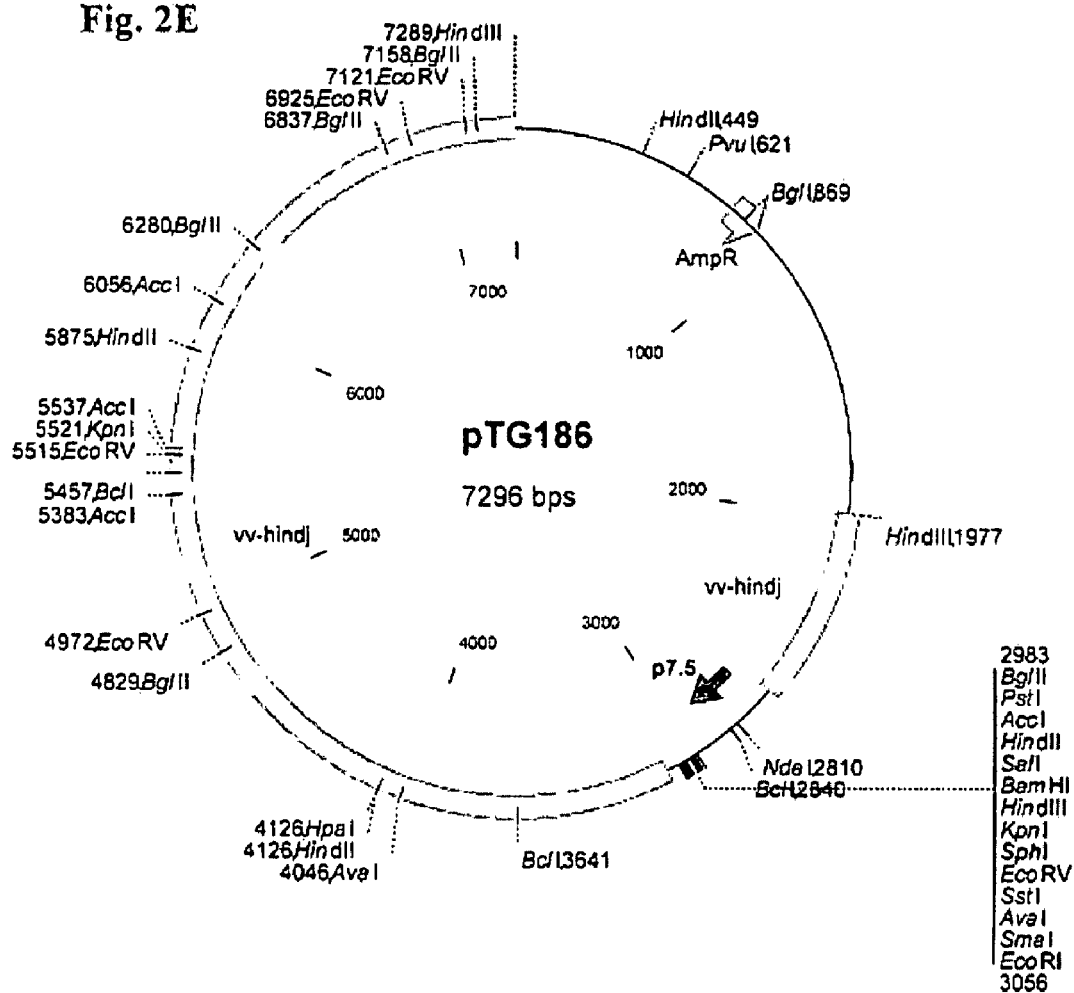
Figure 2F:
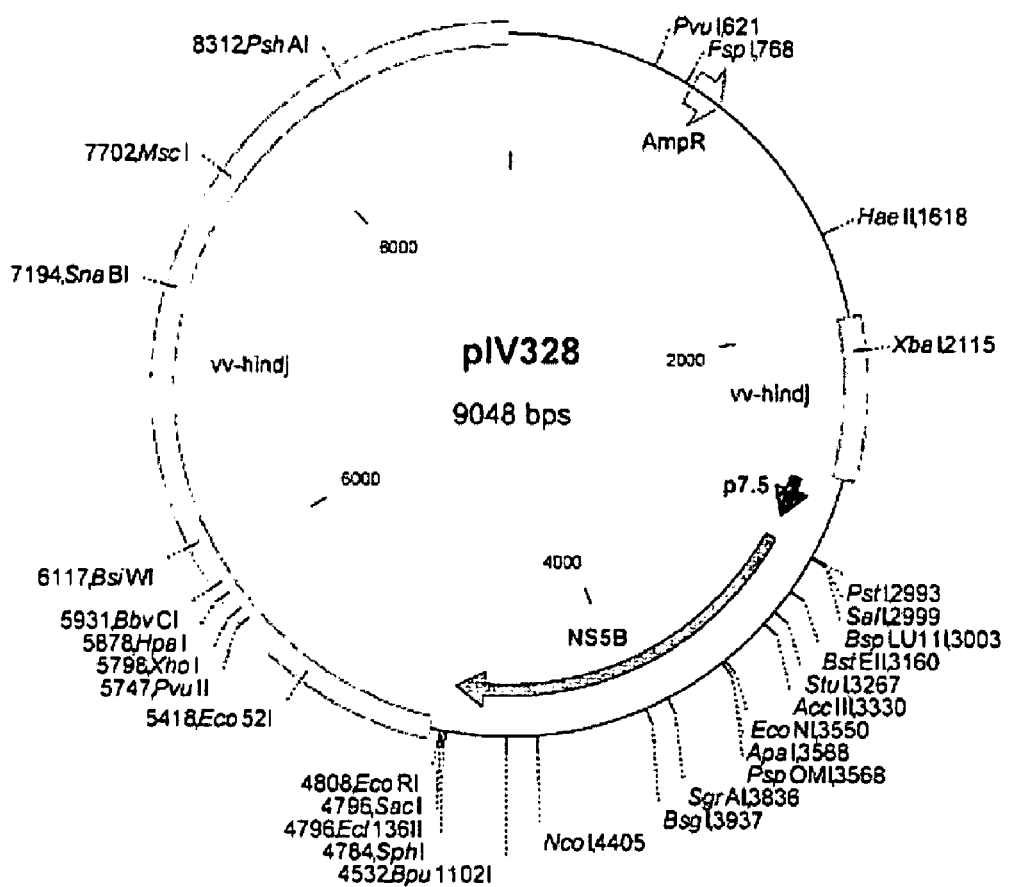
Figure 2G:
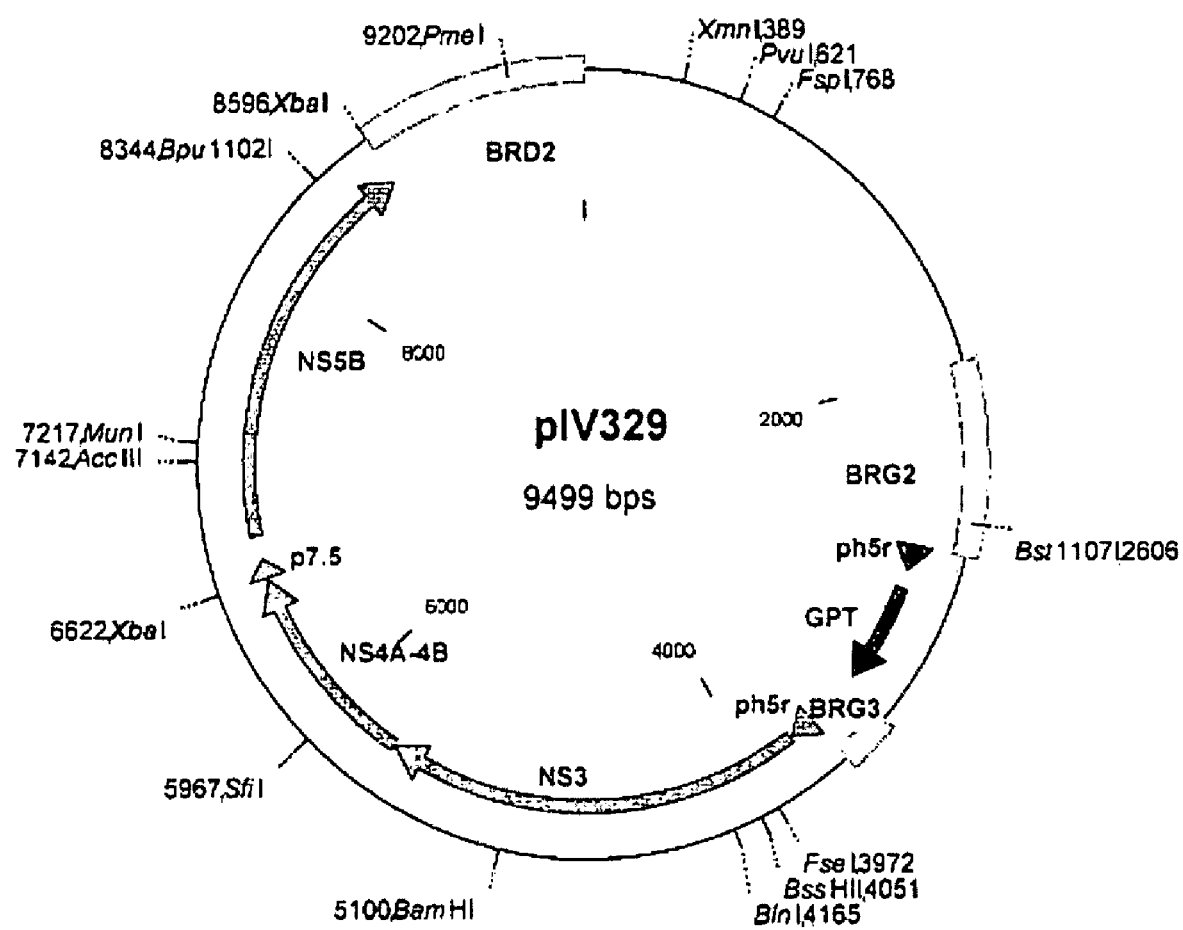
Figure 2H:
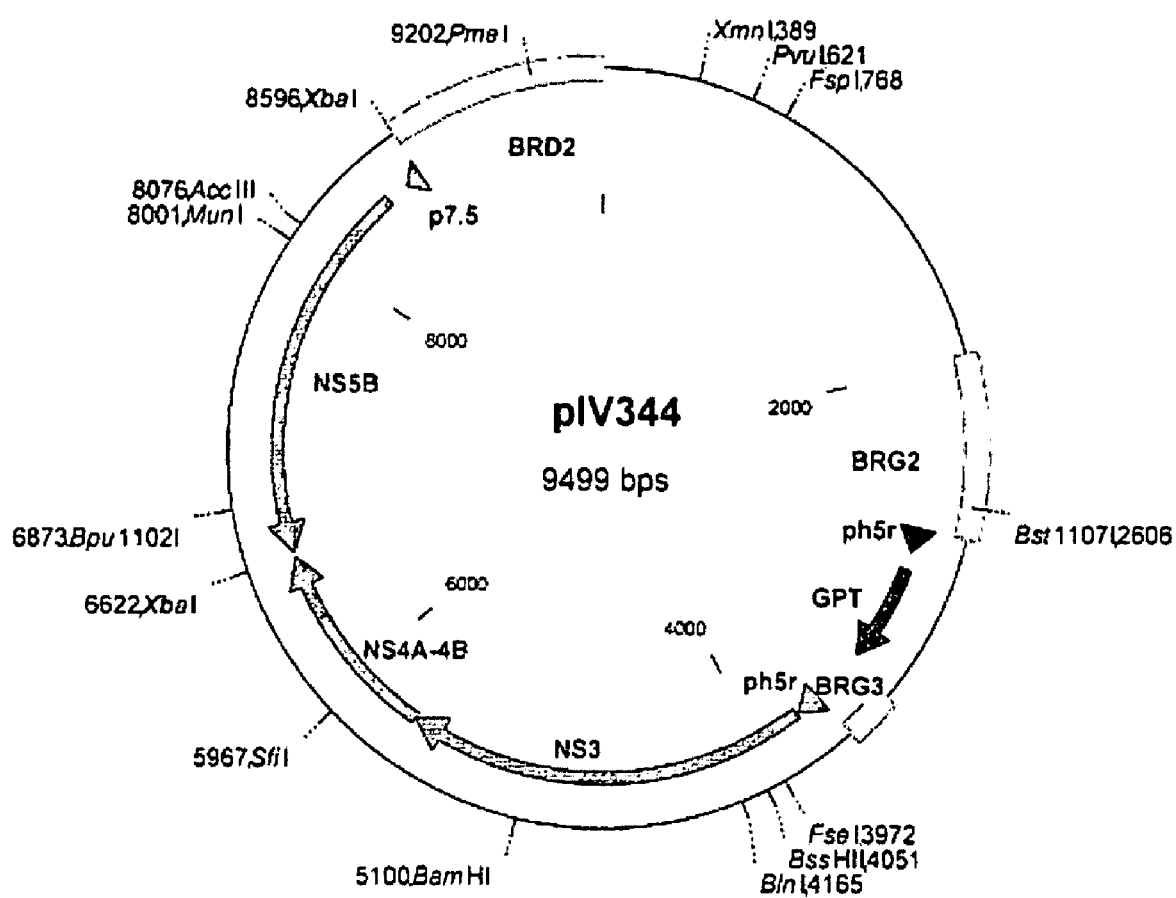
Figure 3A:
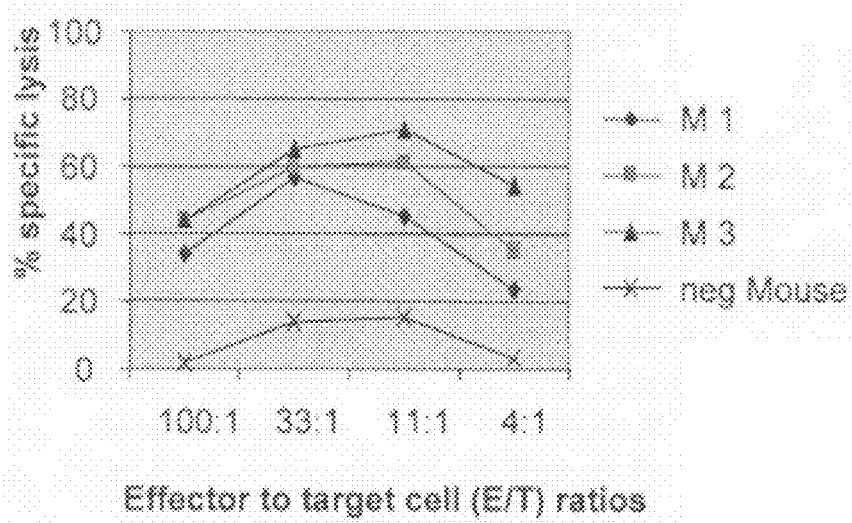
Figure 3B:
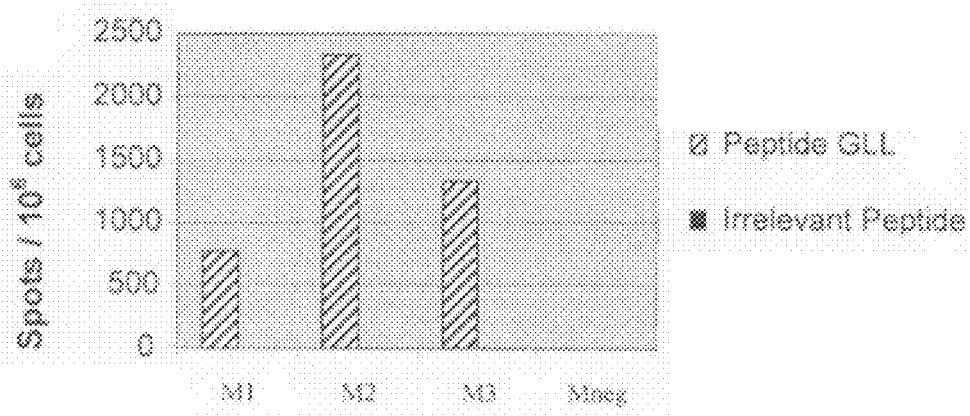

The present invention will be better understood using the following examples that are given only by way of illustration, and are non-limitative, as well as using the attached FIGS. 1 to 16 in which:

FIG. 1A to 1K represents the maps of the different plasmids used for obtaining an adenovirus AdNS3NS4NS5b according to the invention, on which are indicated the sites of the different restriction enzymes and the location of the sequence fragments coding for NS3/NS4 and for NS5b, FIG. 2A to 2H represents the maps of the different plasmids used for obtaining a poxvirus MVA NS3NS4NS5b according to the invention, on which are indicated the sites of the different restriction enzymes and the location of the sequence fragments coding for NS3/NS4 and pour NS5b, FIG. 3 gives the cell response induced by the adenovirus AdNS3NS4, either according to the CTL test (FIG. 3A) where the epitope GLL was used for stimulating the splenocytes in culture and for loading the CTL targets and the result of which is expressed as a specific lysis percentage as a function of the effector/target ratio, or according to the ELISPOT test (FIG. 3B), specific to the epitope GLL, where the result is given in numbers of spots/$10^6$ cells, FIG. 4 gives the cell response induced by the adenovirus AdNS5b according to the test ELISPOT, specific to the epitopes ALY and KLQ, FIG. 5 gives the cell response induced by the adenovirus AdCEIE2 according to the CTL test where the epitope DLM was used for stimulating the splenocytes in culture and for loading the targets of the CTL and the result of which is expressed as a specific lysis percentage as a function of the effector/target ratio.

Figure 6:
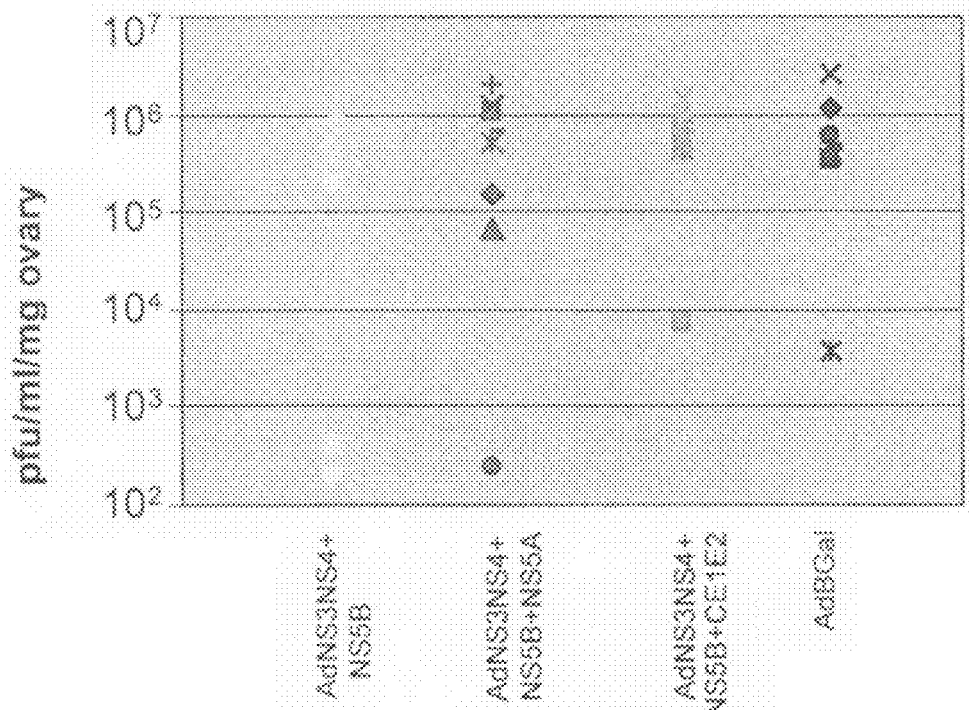
Figure 7:
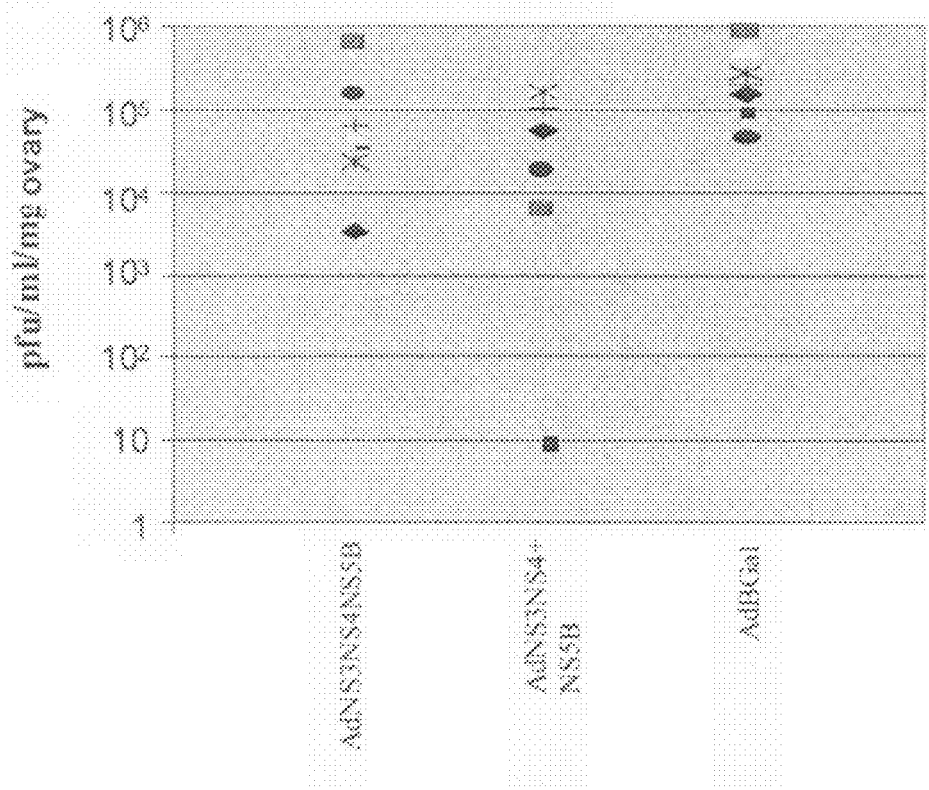

FIG. 6 gives the titre of the recombinant vaccinia virus, resulting from the trial test, in pfu/ml/mg ovary, for the 4 groups of 8 mice immunized by the different combinations of adenovirus: AdNS3NS4+AdNS5b (1st group), the adenoviruses AdNS3NS4+AdNS5b+AdNS5a (2nd group), the adenoviruses AdNS3NS4+AdNS5b+AdCEIE2 (3rd group) and the adenovirus AdβGal (4th group) and FIG. 7 gives the titre of the recombinant vaccinia virus, resulting from the trial test, in pfu/ml/mg ovary, for the 3 groups of 8 mice immunized by the following different combinations of adenovirus: AdNS3NS4NS5b (1st group), AdNS3NS4+AdNS5b (2nd group) and AdβGal (3rd group).

Figure 8:
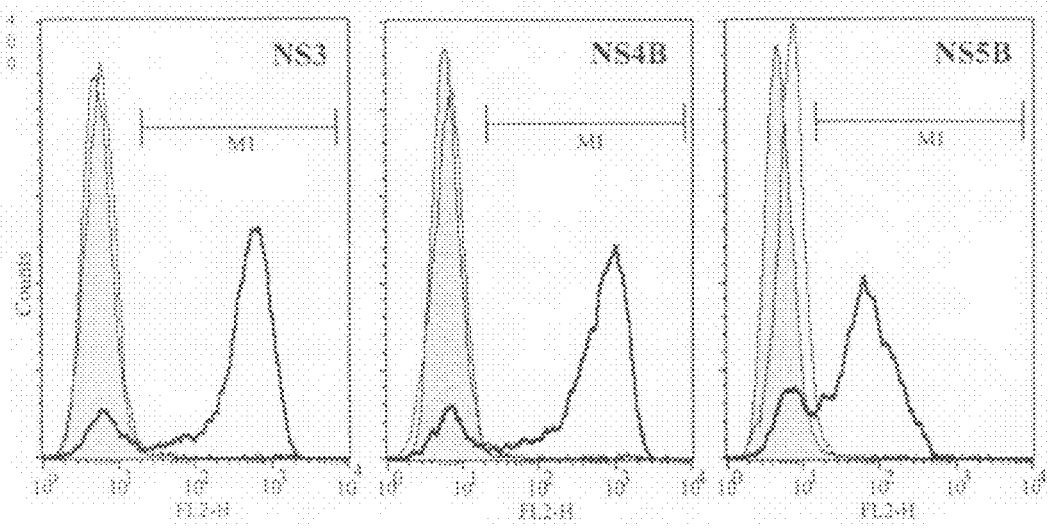

FIG. 8 illustrates In vitro analysis of NS3, NS4 and NS5B expression by flow cytometry following Huh-7 infection by MVA NS3/4-NS5B. MVA NS3/4-NS5B infected Huh-7 cells were harvested 24 h after infection with a MOI of 1 and stained using mouse monoclonal anti-NS3 (8D8E1), anti-NS4B (1B12A3) and anti-NS5B (5B12B7) antibodies. Results are expressed as percentage of positive cells compared with MVA N33 (MVA wild type) infected cells. Bold lines: cells infected with MVA NS34-NS5B, thin lines: cells infected with MVA N33, shadowed histogram: non infected cells. MFI: mean fluorescence intensity.

FIG. 9 provides a comparison of IFNγ-producing CD8+ T cell frequencies specific of NS3 HLA-A2 restricted epitopes induced in HLA-A 2 transgenic mice following two different immunization schedules with the MVA NS34-NS5B. Schedule 1: 3 sub-cutaneous (sc) injections performed at wk 1, 4, 7. Schedule 2: 4 sc injections performed at wk 1, 2, 3 and 6. (A) IFNγ ELISPOT assays performed at wk 6 (schedule 1) or wk 5 (schedule 2). (B) IFNγ ELISPOT assays performed at wk 9 (schedule 1) or wk 8 (schedule 2). IFNγ ELISPOT assays were performed as described in Materials and Methods. M1, M2 and M3 represent 3 mice immunized with the MVA NS34-NS5B. N33 is a representative MVA N33 injected control mouse. NS3 HLA-A2 restricted epitopes GLL and KLT or irrelevant peptide were used for restimulation. Each bar represents the response of a single immunized mouse. The dashed horizontal line represents the cut-off above which IFNγ producing T cell frequency is considered positive.

FIG. 10 illustrates cytotoxic CD8+ T cell responses specific of NS3 or NS5B HLA-A2 restricted epitopes induced in HLA-A2 transgenic mice following administration of MVA NS3/4-NS5B according to two different immunization schedules. Schedule 1: 3 sc injections performed at wk 1, 4, 7.

Schedule 2: 4 sc injections performed at wk 1, 2, 3 and 6. (A) CTL assays performed at wk 6 (schedule 1) or wk 5 (schedule 2). (B) CTL assays performed at wk 9 (schedule 1) or wk 8 (schedule 2). CTL assays were performed as described in Materials and Methods. Data represented the % of specific lysis obtained at different effector to target cell (E/T) ratios. HLA-A2 restricted peptides used to pulse target cells are indicated on top of each graph: GLL for NS3, ALY for NS5B. Each bar represents the response of a single immunized mouse.

FIG. 11 illustrates CD8+ T cell responses characterized by ICS and CTL assays following administration in HLA-A2 transgenic mice of MVA NS3/4-NS5B according to the accelerated immunization schedule. (A) ICS assay. The left part of the Figure represents IFNγ+CD8+ cell dot plots representative of MVA NS34-NS5B and MVA N33 immunized animals and following gating on CD3+ CD4+ cells performed as described in Materials and Methods. GLL peptide or TT (irrelevant stimuli) was used for restimulation. Histogram on the right represents percentage of IFNγ+CD8+ cells detected for 4 MVA NS34-NS5B and 2 MVA N33 immunized mice following GLL restimulation. Empty bars: response of a single immunized mouse, black bars: median values. (B) In vivo CTL assay. GLL-pulsed CFSE high and unpulsed CFSE low target cells were injected into recipient mice as described in Materials and Methods. Twenty hours later, the percentage of target cells killed was evaluated in the spleen. The percentages of specific lysis are indicated for each MVA NS34-NS5B mouse (M1 to M4).

Figure 12:
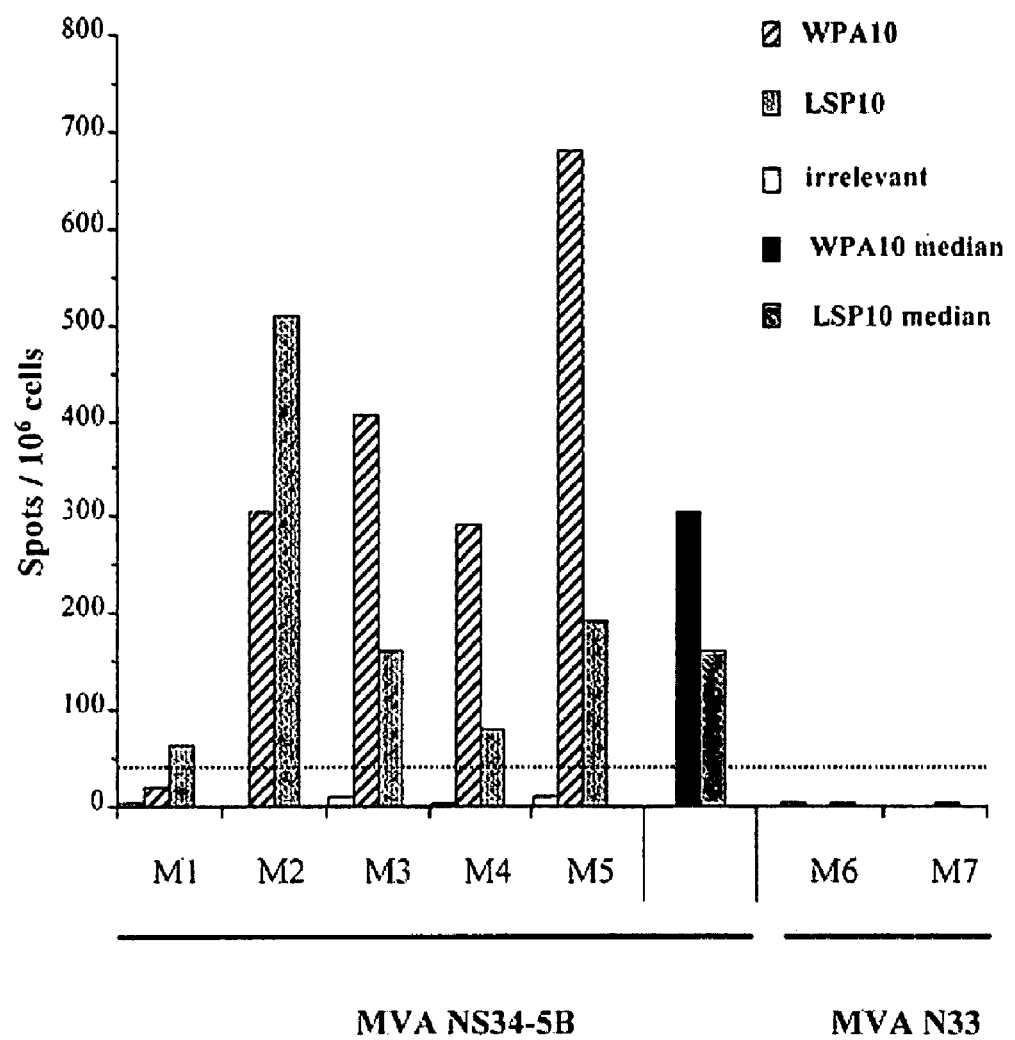

FIG. 12 illustrates IFNγ-producing T cell responses following administration of MVA NS3/4-NS5B in HLA-B7 transgenic mice according to the accelerated immunization schedule. IFNγ ELISPOT assays were performed as described in Materials and Methods. M1-5 represents 5 mice immunized with the MVA NS34-NS5B and M6-7, 2 mice immunized with the MVA N33. Hatched, dot and empty bars represent values obtained for individual mouse and specific of HLA-B7-restricted WPA10, LSP10 or irrelevant peptide epitopes, respectively. Median values are presented for MVA NS34-NS5B injected mice with black (WPA10 peptide) and grey (LSP10 peptide) bars. The dashed horizontal line represents the cut-off above which IFNγ producing T cell frequency is considered positive.

Figure 13:
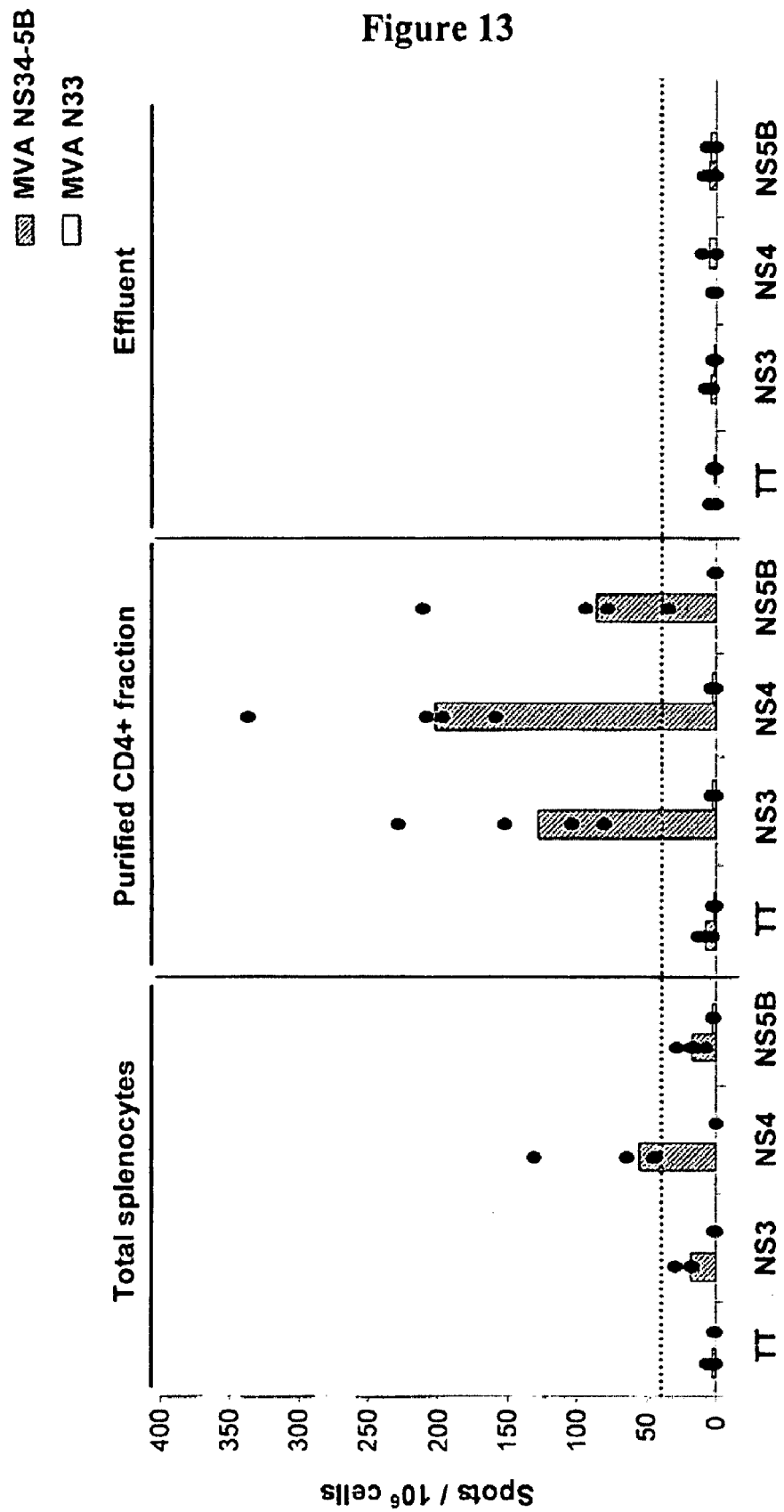

FIG. 13 illustrates IFNγ+CD4+ T cell responses specific of NS3, NS4 and NS5B antigens following administration of MVA NS3/4-NS5B in Balb/C mice according to the accelerated immunization schedule. CD4+ T cells were positively selected from splenocytes of individual MVA NS34-NS5B or MVA N33 immunized mouse. Total splenocytes, CD4+ fraction and effluent fraction were generated and IFNγ ELISPOT assays performed on each fraction for individual mice as described in Materials and Methods. HCV NS3, NS4, NS5B recombinant antigens or TT (irrelevant stimulus) were used for restimulation. Results are shown as bars representing the median spots value detected for $10^6$ splenocytes, obtained for groups of 4 MVA NS34-NS5B (hatched bars) or 2 MVA N33 (empty bars) immunized mice. Within bars, results obtained for each mouse are represented as black dots. The dashed horizontal line represents the cut-off above which IFNγ producing T cell frequency is considered positive.

Figure 14:
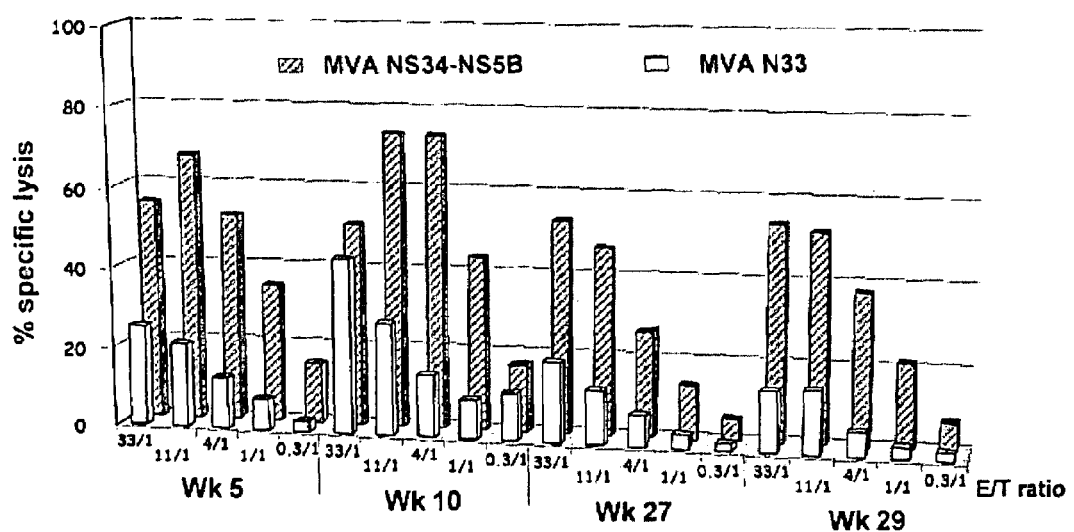

FIG. 14 illustrates the longevity of CTL responses following administration of MVA NS3/4-NS5B in HLA-A2 transgenic mice according to the accelerated immunization schedule. Mice received 4 MVA NS34-NS5B injections at week 1, 2, 3 and 27 and CTL assays were performed as described in Materials and Methods at week 5, 10, 27 and 29. Four MVA NS34-NS5B and 2 MVA N33 injected mice were sacrificed for each time point analyzed. Hatched bars: median % of lysis values for MVA NS34-NS5B injected mice, white bars: median % of lysis values for MVA N33 injected mice, at different effector to target (E/T) ratios.

FIG. 15 illustrates the longevity of IFNγ ELISPOT responses in HLA-A2 transgenic mice following administration of MVA NS34-NS5B according to the accelerated immunization schedule. Mice received 4 MVA NS34-NS5B injections at week 1, 2, 3 and 27 and Elispot assays were performed as described in Materials and Methods at week 5, 10, 27 and 29. Four MVA NS34-NS5B and 2 MVA N33 injected mice were sacrificed for each time point analyzed. NS3 HLA-A2 restricted peptides GLL (A), CVN (B) or KLT (C) or an irrelevant peptide were used for restimulation. Hatched and white bars represent values obtained for individual mice for specific and an irrelevant peptide, respectively. Median values are represented for MVA NS34-NS5B injected mice with black (specific peptide) and doted bars (irrelevant peptide). The dashed horizontal line represents the cut-off above which IFNγ production is considered positive.

Figure 16:
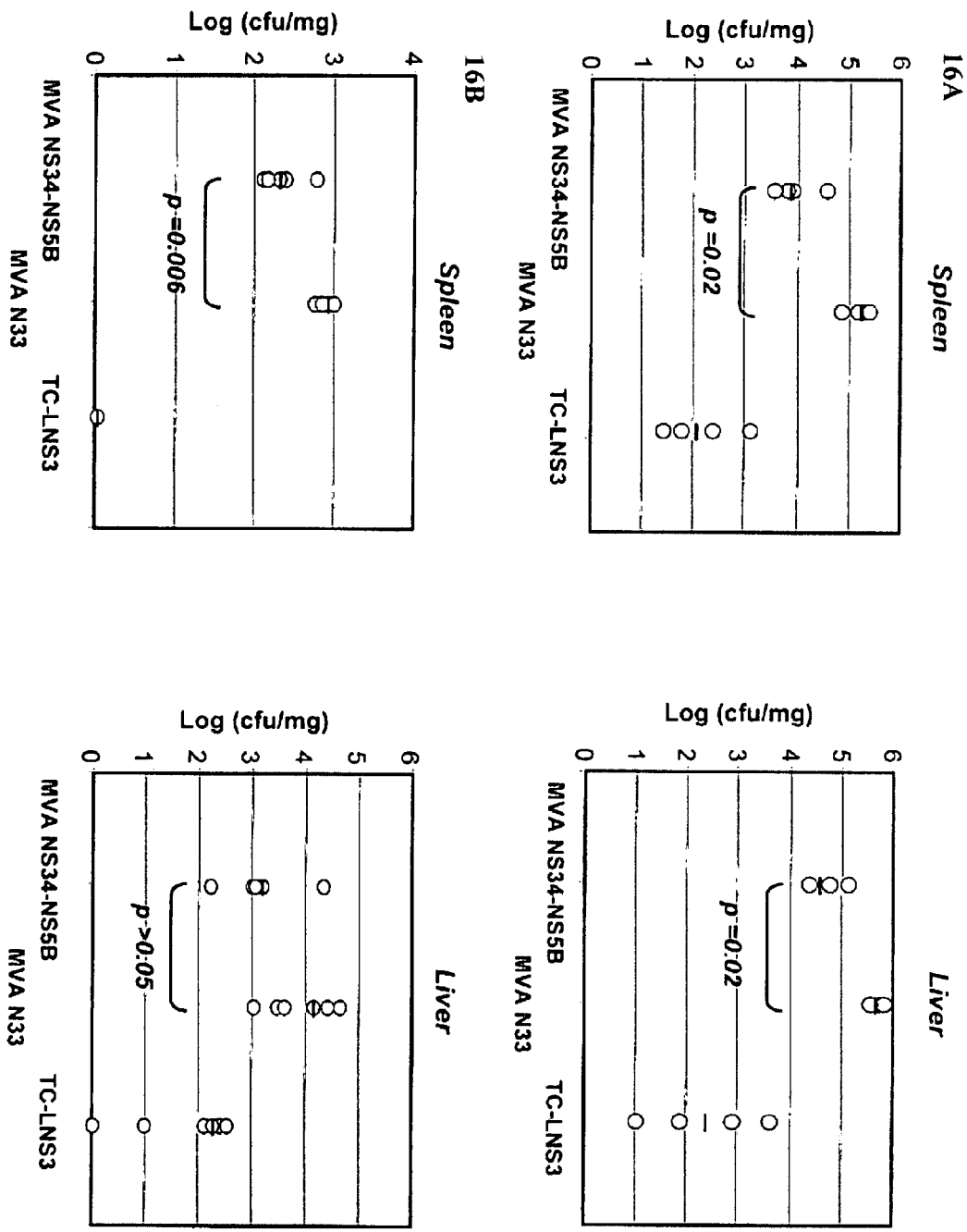

FIG. 16 illustrates the residual bacterial titers in spleen and liver of MVA NS34-NS5B immunized mice challenged with TC-LNS3 bacteria. (A) Bacterial titers in vaccinated HLA-A2 transgenic mice. Four mice were immunized either with the MVA NS34-NS5B or the MVA N33 (negative control) according to the "accelerated" schedule of vaccination or with TC-LNS3 two times at 2 weeks-interval using a low immunization dose (0.05 to 0.1 $LD_{50}$) (positive control), 15 days prior challenge. Challenge was performed with a dose of 1 LD50 of TC-LNS3 bacteria and mice were sacrificed 2 days later. Residual bacterial titers were evaluated by titrations of livers and spleens serial dilutions. Individual mice in each group are represented by circular symbols and the median value obtained for each group is represented by the black and thick line. P values are calculated according to the non parametric test of Mann Whitney and values are considered as statistically different when p<0.05. (B) Bacterial titers in vaccinated Balb/c mice. Challenge was carried out as described in (A) except that 6 mice were included in each animal group.

EXAMPLE 1

Preparation of an Adenovirus Allowing the Expression of the Proteins NS3/NS4 and NS5b According to the Invention 1. Adenovirus The recombinant adenoviruses are generated by transfection (CaPO3) of the complementation line 293 (Graham, Smiley, et al. 1977) after linearization of the genomes by PacI. The recombinant viruses propagate and are amplified on this same line, and their purification is carried out from the infected cells. The cells are recovered by centrifugation (1500 rpm, 10 minutes) and lysed by 3 freeze/thaw cycles. The cell lysate is clarified by two centrifugations (2000 rpm, 10 minutes; 8000 rpm, 15 minutes), then purified by two successive ultracentrifugations. The first is carried out on a Caesium Chloride gradient (densities 1.4 and 1.25) at 30,000 rpm for 1 hour. The second is carried out on a Caesium Chloride cushion (density 1.34) at 35,000 rpm for 18 hours. The phases containing the virions are removed and diluted by half in a 60% saccharose buffer. The viral suspensions are then dialysed against formulation buffer (for 10 litres: 3423 g of saccharose; 12.11 g of Tris; 2.033 g of $MgCl_2$; 87.7 g of NaCl), then aliquoted. Their titration is carried out by indirect immunofluorescence on 293 cells infected by different viral dilutions and marked by an antibody specific to the adenoviral DNA-Binding Protein (α72K B6-8) (Reich, Sarnow, et al. 1983).

2. Preparation of the Adenovirus AdNS3NS4

This adenovirus allows the expression of the gene coding for the polyprotein NS3/NS4 (SEQ ID NOs: 1 and 2) under the control of the CMV promoter.

2.1 PCR Amplification of the Nucleotide Sequence Coding for the Polyprotein NS3/NS4

In order to do this, the following oligonucleotides were used:

oIV166:
(SEQ ID NO: 9)
5'-GGG GGG GCT ATG GCG CCT ATC ACG GCC TA-3' oIV171:
(SEQ ID NO: 10)
5'-GGG GGG ACG CGT TTA GCA TGG CGT GGA GCA GT-3' as well as the following reagents:

Taq DNA Polymerase, PCR buffer, MgCl, 1.5 mM and dNTP 10 mM (Invitrogen).

The PCR conditions were the following:
5 minutes at 94° C., then
30 cycles of the series: 45 seconds at 94° C., 45 seconds at 62° C. and 1 minute at 72° C., then
10 minutes at 72° C.

2.2 Insertion of the PCR Fragment NS3/NS4 into the Transfer Plasmid pTG13387

The following stages were carried out:
Enzymatic digestion of the plasmid pTG13387 (FIG. 1A, Transgene) by NheI/MluI (NheI, Invitrogen in React 4 Buffer and MluI, Invitrogen in React 3 Buffer)
Enzymatic digestion of the fragment NS3/NS4 by NheI/MluI
Ligation (T4 DNA Ligase (Invitrogen) in Reaction Buffer (Invitrogen)),
Bacterial transformation (strain 5K, (Transgene)
Selection of bacterial clones on LB medium (Difco)+ampicillin (100 µg/ml, Duchefa)
Plasmid maxi-preparation (Qiagen, according to manufacturer's protocol) of a positive clone after restriction analysis
Restriction analysis: digestion by SmaI (Invitrogen in React 4 Buffer) and obtaining of fragments of: 5450, 2164, 909, 214 and 180 pb
Obtaining of the plasmid pIV315 deleted from its E1 region and containing the sequence NS3/NS4 under the control of the CMV promoter (FIG. 1B).

2.3 Homologous Recombination with the Complete Adenoviral Genome Deleted from its E3 Region Contained in the Plasmid pTG6624

The following stages were carried out:
Enzymatic digestion of the plasmid pIV315 obtained above by PacI/PvuI (PacI in NEB1 buffer, Biolabs and PvuI in React 7 Buffer, Invitrogen); isolation on agarose gel of the fragment containing the cassette pCMV-NS3-NS4
Enzymatic digestion of the plasmid pTG6624 (FIG. 1C) by ClaI (in React 1 Buffer, Invitrogen)
Bacterial transformation (strain BJ, (Transgene) in order to carry out the homologous recombination between the two plasmid fragments
Selection of bacterial clones on LB medium+ampicillin (100 µg/ml)
Plasmid maxi-preparation (Qiagen) of a positive clone after restriction analysis
Restriction analysis: digestion by SmaI and obtaining of fragments of: 2263, 621, 3814, 214, 2164, 909, 180, 2463, 6480, 1398, 4456, 1455, 3540, 3386, 230 and 3685 pb
Obtaining of the complete adenoviral genome Adenovirus AdNS3NS4, deleted from its E3 and E1 regions, the latter having been replaced by the expression cassette pCMV-NS3-NS4 (pIV317, FIG. 1D).

3. Preparation of the Adenovirus AdNS3NS4NS5b

This adenovirus allows the expression of the gene coding for the polyprotein NS3/NS4 under the control of the CMV promoter and the expression of the gene coding for the polypeptide NS5b under the control of the SV40 promoter.

3.1 Construction of the Transfer Plasmid Allowing the Cloning in the E3 Region of the Adenovirus of a Coding Sequence Under the Control of the CMV Promoter The following stages were implemented:
Enzymatic digestion of the plasmid pTG4664 (FIG. 1E, Transgene) by BglII (in React 3 Buffer, Invitrogen)
Enzymatic digestion of the plasmid pTG3074 (FIG. 1F, Transgene) by BamHI/BglII (in React 3 Buffer, Invitrogen)
Ligation (T4 DNA ligase), bacterial transformation (strain 5K)
Selection of bacterial clones on LB medium+ampicillin (100 µg/ml)
Plasmid maxi-preparation (Qiagen) of a positive clone after restriction analysis
Restriction analysis: digestion by SmaI and obtaining of fragments of: 4940, 1305 and 230 pb
Obtaining of the plasmid pIV267 (FIG. 1G)
Digestion of the plasmid pIV267 thus obtained by ClaI/MunI (in React 1 Buffer, Invitrogen)
Treatment by DNA Polymerase I, Large (Klenow) Fragment (in React 2 Buffer, Invitrogen)
Ligation (T4 DNA Ligase)
Bacterial transformation (strain 5K)
Selection of bacterial clones on LB medium+ampicillin (100 µg/ml)
Plasmid maxi-preparation (Qiagen)
Restriction analysis: digestion by SmaI and obtaining of fragments of: 4692, 1305 and 230 pb
Obtaining of the plasmid pIV270, transfer plasmid allowing the cloning in the E3 region of the adenovirus of a coding sequence under the control of the CMV promoter (FIG. 1H).

3.2 Replacement of the CMV Promoter by the SV40 Promoter in pIV270

The following stages were carried out:
PCR amplification of the nucleotide fragment corresponding to the SV40 promoter, from the commercial plasmid pcDNAHygro (Clonetech) using the following oligonucleotides:

oIV232:
(SEQ ID NO: 11)
5'-GGG GGG AGA TCT CCA GCA GGC AGA AGT ATG-3' oIV233:
(SEQ ID NO: 12)
5'-GGG GGG GTC GAC CGA AAA TGG ATA TAC AAG CTC-3' and according to the procedure described in point 2.1 above, except that a temperature of 58° C. instead of 62° C. was used Enzymatic digestion of pIV270 by BglII/SalI (in React 10 Buffer, Invitrogen)

Enzymatic digestion of the PCR fragment by BglII/SalI

Ligation (T4 DNA ligase), bacterial transformation (strain 5K)

Selection of the bacterial clones on LB medium+ampicillin (100 μg/ml)

Plasmid maxi-preparation (Qiagen) of a positive clone after restriction analysis Restriction analysis: digestion by SmaI and obtaining of fragments of: 4692, 719, 80 and 230 pb Obtaining of the plasmid pIV330, transfer plasmid allowing the cloning in the E3 region of the adenovirus of a coding sequence under the control of the SV40 promoter (FIG. 11).

3.3 Insertion of the PCR Fragment NS5b into the Transfer Plasmid pIV330

The following stages were carried out:

PCR amplification of the nucleotide sequence coding for the protein NS5b (SEQ ID NOs: 3 and 4) using the following nucleotides:

oIV212:
(SEQ ID NO: 13)
5'-GGG GGG TCT AGA ATG TCA ATG TCC TAC ACA TGG AC-3' oIV218:
(SEQ ID NO: 14)
5'-GGG GGG TCT AGA TTA CCG GTT GGG GAG CAG GT-3' and according to the procedure described in point 2.1 above, except that a temperature of 60° C. instead of 62° C. was used Enzymatic digestion of the plasmid pIV330 obtained above by XbaI (in React 2 Buffer, Invitrogen)

Enzymatic digestion of the PCR fragment by XbaI

Ligation (T4 DNA Ligase), bacterial transformation (strain 5K)

Selection of the bacterial clones on medium LB+ampicillin (100 μg/ml)

Plasmid maxi-preparation (Qiagen) of a positive clone after restriction analysis Restriction analysis: digestion by SmaI and obtaining of fragments of: 4692, 1505, 760, 719 and 230 pb Obtaining of the plasmid pIV336, transfer plasmid in the E3 deletion containing the sequence NS5b under the control of the SV40 promoter (FIG. 1J)

3.4 Homologous Recombination with the Recombinant Adenoviral Genome pIV317 in Order to Obtain the Adenovirus of the Title The following stages were implemented:

Digestion of the plasmid pIV317 obtained in point 2.3 above by SrfI (in Universal Buffer, Stratagene)

Digestion of the plasmid pIV336 obtained in point 3.3 by NheI/SacII (in Buffer T, Amersham Pharmacia Biotech) and isolation on agarose gel of the fragment containing the cassette pSV40-NS5b Bacterial transformation (strain BJ) for carrying out the homologous recombination between the two plasmid fragments Selection of the bacterial clones on medium LB+ampicillin (100 μg/ml)

Plasmid maxi-preparation (Qiagen) of a positive clone after restriction analysis Restriction analysis: digestion by SmaI and obtaining of fragments of: 6480, 4456, 3814, 3540, 3386, 2739, 2463, 2263, 2164, 1455, 1398, 1105, 909, 760, 719, 621, 230, 214 and 180 pb Obtaining of the desired complete adenoviral genome, deleted from the E1 region, the latter having been replaced by the expression cassette pCMV-NS3-NS4, and deleted from the E3 region, the latter having been replaced by the expression cassette pSV40-NS5B (plasmid pIV342, FIG. 1K).

4 Confirmation of the Expression of the Antigens Inserted into the Different Adenoviruses The expression of the HCV antigens encoded by the adenoviruses AdNS3NS4, AdNS5b and AdNS3NS4NS5b was verified by Western blot after infection of Huh7 cells.

As expected, all the antigens were expressed.

EXAMPLE 2

Preparation of a Poxvirus Allowing the Expression of the Proteins NS3/NS4 and NS5b According to the Invention 1. MVA Poxvirus The strain Modified Virus Ankara MVATG N33 was supplied by TRANSGENE S. A. (Strasbourg, France).

2. Preparation of the Transfer Plasmid Allowing the Expression of the Gene NS3/NS4 Under the Control of the ph5r Promoter 2.1 Construction of the pIV250 Vector Containing the Recombination Arms BRG2 and BRD2 of the MVA, as well as the Selection Gene GPT Under the Control of the Promoter ph5r (MVA), Followed by a Second Promoter ph5r in Order to Allow the Expression of the Gene of Interest At this point, the insertion of the fragment ph5r-GPT-BRG3-ph5r (originating from the plasmid pTG9997, Transgene) into the plasmid pTG6018 (Transgene) containing the recombination arms BRG2 and BRD2 is desired.

In order to do this, the following stages were carried out:

Enzymatic digestion by BamHI/SacI (in React 2 Buffer, Invitrogen) of the vector pTG6018 (FIG. 2A)

Enzymatic digestion by BamHI, then partial digestion by SacI of the plasmid pTG9997 (FIG. 2B)

Purification according to the QIAGEN protocol of the restriction fragment of 1047 pb that contains the sequence coding for ph5r-GPT-BRG3-ph5r Ligation (T4 DNA Ligase), bacterial transformation (strain TG1, Statagene)

Selection of the bacterial clones on ampicillin (100 μg/ml)

Plasmid maxi-preparation (Qiagen) of a positive clone after restriction analysis (EcoRV+HindIII (in React 2 Buffer, Invitrogen): fragments of 246, 439, 476, 826 and 2789 pb; SacI: fragments of 915 and 3861 pb)

Obtaining of the plasmid aimed at (pIV250, FIG. 2C).

2.2 PCR Amplification of the Nucleotide Sequence Coding for the Polyprotein NS3/NS4

The following oligonucleotides were used:

```
oIV225:
                                    (SEQ ID NO: 15)
5'-GGG GGG CTG CAG ATG GCG CCT ATC ACG GCC TA-3' oIV226:
                                    (SEQ ID NO: 16)
5'-GGG GGG TCT AGA TTA GCA TGG CGT GGA GCA GT-3'
``` and according to the procedure described in Example 1, point 2.1 above, except that a temperature of 52° C. instead of 62° C. was used.

2.3 Insertion of the Fragment of PCR NS3-NS4 in the Plasmid pIV250

In order to do this, the following stages were carried out:

Enzymatic digestion of the plasmid pIV250 obtained in point 2.1 above by PstI (in React 2 Buffer, Invitrogen)/XbaI Enzymatic digestion of the PCR fragment NS3/NS4 by PstI/XbaI Ligation (T4 DNA Ligase), bacterial transformation (strain TG1)

Selection of the bacterial clones on ampicillin (100 µg/ml)

Plasmid maxi-preparation (Qiagen) of a positive clone after restriction analysis: (HindIII (in React 2 Buffer, Invitrogen): fragments of 4763 and 2789 pb; SphI (in React 6 Buffer, Invitrogen): 1534 and 5991 pb; NcoI (in React 3 Buffer, Invitrogen): 2764 and 4761 pb)

Obtaining of the transfer plasmid containing the sequence coding for the polyprotein NS3/NS4 under the control of the promoter ph5r (pIV327, FIG. 2D).

3. Preparation of the Plasmid pIV328 Allowing the Expression of the Protein NS5b Under the Control of the p7.5 Promoter 3.1 PCR Amplification of the Nucleotide Sequence Coding for the Protein NS5b The following nucleotides were used:

oIV227:
(SEQ ID NO: 17)
5'-GGG GGG GTC GAC ATG TCA ATG TCC TAC ACA TGG AC-3' oIV228:
(SEQ ID NO: 18)
5'-GGG GGG GCA TGC TTA CCG GTT GGG GAG CAG GT-3' and according to the procedure described in Example 1, point 2.1 above, except that a temperature of 52° C. instead of 62° C. was used.

3.2 Obtaining of the Plasmid

The following stages were carried out:

Enzymatic digestion of the PCR fragment coding for NS5b by SalI/SphI

Enzymatic digestion of pTG186 (FIG. 2E, Transgene) by SalI/SphI

Dephosphorylation of the vector pTG186 (ROCHE alkaline phosphatase)

Ligation (T4 DNA Ligase), bacterial transformation (strain TG1)

Selection of the bacterial clones on ampicillin (100 µg/ml)

Plasmid maxi-preparation (Qiagen) of a positive clone after restriction analysis: (HindIII: fragments of 1984, 2627 and 4437 pb; BglII: fragments of 321, 557, 1361, 1451, 2237 and 3121 pb; KpnI (in React 4 Buffer, Invitrogen): fragments of: 2787 and 6261 pb)

Obtaining of the transfer plasmid containing the sequence coding for the polypeptide NS5b under the control of the p7.5 promoter (pIV328, FIG. 2F).

4. Preparation of the Transfer Plasmids pIV329 and pIV344 Allowing the Expression of the Gene Coding for the Polyprotein NS3/NS4 Under the Control of the ph5r Promoter and of the Gene Coding for the Polyprotein NS3/NS4 Under the Control of the p7.5 Promoter In order to do this the following stages were implemented:

PCR amplification of the nucleotide sequence coding for the protein NS5b from the plasmid pIV328 obtained in point 3.2 above using the following oligonucleotides:

oIV229:
(SEQ ID NO: 19)
5'-GGG GGG TCT AGA CCG GTA GTT CGC ATA TAC ATA-3' oIV218:
(SEQ ID NO: 14)
5'-GGG GGG TCT AGA TTA CCG GTT GGG GAG CAG GT-3' and according to the procedure described in Example 1, point 2.1 above, except that a temperature of 52° C. instead of 62° C. was used.

Enzymatic digestion of the fragment of PCR by XbaI

Enzymatic digestion of the plasmid pIV327 obtained in point 2.3 above by XbaI

Ligation (T4 DNA Ligase), bacterial transformation (strain TG1)

Selection of the bacterial clones on ampicillin (100 µg/ml)

Plasmid maxi-preparation (Qiagen) of 2 positive clones after restriction analysis: (PstI: pIV329: fragments of 3033 and 6466 pb, pIV344: 4641 and 4858 pb; ApaI (in React 4 Buffer, Invitrogen): pIV329: 454, 960 and 8085 pb, pIV344: 454, 1418 and 7627 pb; NcoI: pIV329: 4269, 469 and 4761 pb, pIV344: 3053, 1685 and 4761 pb; SmaI: pIV329: 214, 2164, 1444 and 5677 pb, pIV344: 214, 2164, 928 and 6193 pb)

Obtaining either of the transfer plasmid allowing the expression of the polyprotein NS3/NS4 under the control of the ph5r promoter and of the protein NS5b under the control of the p7.5 promoter, the 2 expression cassettes being oriented in the same direction (pIV329, FIG. 2G), or of the transfer plasmid allowing the expression of the polyprotein NS3/NS4 under the control of the ph5r promoter and of the protein NS5b under the control of the p7.5 promoter, the 2 expression cassettes being oriented in opposite directions (pIV344, FIG. 2H).

5. Confirmation of the Expression of the Antigens Inserted into the Different Poxviruses It was verified by Western blot, after infection of Huh7 cells with the poxviruses concerned, that the poxviruses pIV329 and pIV344, containing the sequences coding for the polyprotein NS3/NS4 and the polypeptide NS5b, expressed said HCV antigens.

EXAMPLE 3

Demonstration of the Immunogenicity of the Combination of NS3/NS4 and NS5b

1. Immunization of Mice

HLA-A2.1 transgenic mice were immunized, once, by intramuscular injection of at least one adenovirus chosen from the following adenoviruses:

AdNS3NS4 prepared in Example 1 above (point 2.3),

AdNS5 prepared in Example 1 above (point 3.3),

AdNS5a prepare according to the procedure of Example 1, point 2, except that the following nucleotide primers were used in order to amplify the nucleotide sequence coding for the polypeptide NS5a (SEQ ID NOs: 5 and 6):

oIV172:
(SEQ ID NO: 20)
5'-GGG GGG GGT ACC ATG TCC GGC TCG TGG CTA AGG-3',

-continued oIV173:
(SEQ ID NO: 21)
5'-GGG GGG TCT AGA TTA GCA GCA GAC GAT GTC GTC-3', in the PCR the temperature of 62° C. was replaced by 56° C., the enzymatic digestion of pTG 13387 and of the fragment NS5a were implemented by KpnI/XbaI, restriction analysis by digestion by SmaI of pTG13387 producing fragments of 180 and 7251 pb and of pTG6624 producing fragments of 2263, 621, 5615, 180, 2463, 6480, 1398, 4456, 1455, 3540, 3386, 230 and 3685 pb.

AdCE1E2 according to the procedure of Example 1, point 2, except that the following nucleotide primers were used in order to amplify the nucleotide sequence coding for the core-E1-E2 polyprotein (also called CE1CE2) (SEQ ID NOs: 7 and 8):

oIV62:
(SEQ ID NO: 22)
5'-GGG GGG GCT AGC ATG AGC ACA AAT CCT AAA CCT-3', oIV68:
(SEQ ID NO: 23)
5'-GGG GGG TCT AGA TCA GGC CTC AGC CTG GGC TAT-3', in the PCR the temperature of 62° C. was replaced by 56° C., the enzymatic digestion of pTG13387 and of the fragment CE1CE2 were implemented by NheI/XbaI, restriction analysis by digestion by SmaI of pTG13387 producing fragments of 163, 435, 2270, 180 and 5254 pb and of pTG6624 producing fragments of 2263, 621, 3618, 163, 435, 2270, 180, 2463, 6480, 1398, 4456, 1455, 3540, 3386, 230 and 3685 pb, AdNS3NS4NS5b prepared in Example 1 above (point 3) and AdβGal (Transgene), according to the following protocol:
- $10^9$ pfu of AdNS3NS4 or
- $10^9$ pfu of AdNS5b or
- $10^9$ pfu of AdCEIE2 or
- $10^9$ pfu of AdNS3NS4 and $10^9$ pfu of AdNS5b or
- $10^9$ pfu of AdNS3NS4, $10^9$ pfu of AdNS5b and $10^9$ pfu of AdNS5a
- $10^9$ pfu of AdNS3NS4, $10^9$ pfu of AdNS5b and $10^9$ pfu of AdCEIE2
- $10^9$ pfu of AdNS3NS4 NS5b or
- $10^9$ pfu of Adβ-Gal as control.

Before immunization, the expression of the HCV and β-Gal antigens by the different adenoviruses used for the immunization was verified by Western blot.

2. CTL and ELISPOT Tests

Fifteen days after injection, the cell response was analyzed by isolating the spleen cells (splenocytes) of the mice and a CTL test and an ELISPOT test were carried out as follows:

For the CTL test, these splenocytes were cultured on 24-well plates in the presence of:
- 5 µM of the epitope GLL (GLLGCIITSL, SEQ ID NO: 24) in the case of the splenocytes originating from mice having received AdNS3NS4, 5 µM of the epitope ALY (ALYDVVSTL, SEQ ID NO: 25) or 5 µM of the epitope KLQ (KLQDCTMLV, SEQ ID NO: 26) in the case of the splenocytes originating from mice having received AdNS5b or 5 µM of the epitope DLM (DLMGYIPLV, SEQ ID NO: 27) in the case of the splenocytes originating from mice having received AdCE1 E2, said epitopes being in synthetic peptide form (Eurogentex) and,
- 10 U of murine recombinant interleukin 2 (Brinster et al., Hepatology 2001) per ml in alpha minimum essential medium (αMEM) for 5 days. On the 5th day, the restimulation stage was carried out, which consists of adding naive mice splenocytes to the splenocytes in culture in the presence of said epitopes over 2 days. On the 7th day, the CTL test was carried out, which consists of bringing into contact the splenocytes from the immunized mice after 7 days of culture (effector cells) and EL4 S3-Rob HDD cells loaded with 10 µM of said epitopes and labelled with $Cr^{51}$ (target cells). The specific cytotoxic activity of the effector cells was determined by measuring, after 4 hours of incubation with the target cells, $Cr^{51}$ released following lysis of the target cells using a γ-Cobra II counting apparatus (Packard, Rungis, France) The maximum spontaneous release from wells containing either medium alone, or lysis buffer (HCl IN) was determined. The specific percentage of cytotoxicity was calculated by the formula: (release in the test—spontaneous release)/(maximum release—spontaneous release)×100. The epitope-specific lysis was determined by the difference between the percentage of specific lysis obtained in the presence or in the absence of said epitopes.

The ELISPOT test was carried out by culturing the splenocytes for 48 hours in Multiscreen 96-well plates (Millipore) previously coated with anti-interferon gamma antibodies (IFNγ) (I0 µg/ml final). The splenocytes were cultured in the presence of 10 µM of the appropriate epitopes, as indicated above, and of 10 U of murine recombinant interleukin 2 per ml in αMEM. For the positive control, the splenocytes were cultured in the presence of concanavalin A (5 µg/ml). For the negative control, the splenocytes were cultured either in the presence of a non-specific peptide belonging to the capsid protein of HCV, of sequence DLMGYIPLV (also called irrelevant peptide), or in medium alone without epitope. The wells were washed three times, with 0.05% PBS-Tween then PBS respectively, an operation followed by incubation for 2 hours with anti-IFNγ antibodies from biotinylated mice. After washing, the wells were incubated for 1 hour with a streptavidine-horseradish peroxidase conjugate and the enzymatic activity was developed by degradation of the AEC (aminoethylcarbazole) substrate. The spots obtained were counted using a Zeiss ELISpot reader (Zeiss microscope in conjunction with the KS-ELISpot software).

The results are indicated in FIGS. 3 to 5 in which M corresponds to mouse and Mneg corresponds to the control mouse.

These results demonstrate that

AdNS3NS4 clearly induces a cell-mediated response specific of the expressed antigens, as illustrated in FIGS. 3A and 3B by the detection of T lymphocytes specific to the epitope GLL contained in NS3.

AdNS5b clearly induces a cell-mediated response specific of the expressed antigens, as illustrated in FIG. 4 by the detection of T lymphocytes specific to the epitope ALY and KLQ contained in NS5b.

AdCEIE2 clearly induces a cell-mediated response specific of the expressed antigens, as illustrated in FIG. 5 by the detection of T lymphocytes specific to the epitope DLM contained in the Core protein.

3. In Vivo Trial Test Using a Recombinant Vaccinia Virus

In order to evaluate whether the specific immune responses induced by the different adenoviruses were capable of inducing protection against a infectious disease trial ("in vivo protection"), we subjected the vaccinated mice to such a trial.

The mice not being directly infectable by HCV, in order to link the induction of a specific immune response and resistance to an infection, we used a recombinant vaccinia virus (strain WR) coding for the non-structural proteins of HCV (NS2 to NS5b) in order to carry out this trial. This recombinant vaccinia virus, after intra-peritoneal injection of $10^7$ pfu in the mouse, will be replicated in the animal. The replication of this virus induces an immune response both specific to the vaccinia antigens and specific to the HCV antigens, as it also expresses the NS proteins of HCV. This specific response to the HCV antigens will be all the more effective and vigorous as the mice will have already received a vaccine expressing the HCV antigens. In other words, the more the effective vaccination (in the present case carried out with the recombinant adenoviruses) has been (i.e. the immune system of the mice have been effectively "primed" by the vaccine), the stronger will be the anti-HCV response generated after trial by the recombinant vaccinia virus and, consequently, the more the mice are "protected" against this trial. In practice, the lower the residual vaccinia virus count in the mice, the more effective the protection or the neutralization due to the vaccination has been.

The neutralization of the vaccinia virus reflects both the cell response induced by the HCV proteins and by the vaccinia proteins. The neutralization is evaluated by titration of the residual vaccinia virus from the ovaries of the animals as follows: the ovaries are removed 4 days post-trial, sonicated, freeze-thawed 3 times then after centrifugation, successive dilutions of supernatant are titrated according to the lysis plaque technique (Murata et al., PNAS, vol. 100, p. 6753-6758) on Hutk- cells. The viral titres are determined in pfu/ml/mg of ovary.

4. Demonstration of Superior Protection of a Vaccination Combining the Polyprotein NS3/NS4 and the Polypeptide NS5b.

The recombinant virus titre of the vaccine was determined for 4 groups of 8 mice immunized by the following combinations of adenoviruses: AdNS3NS4+AdNS5b (1st group), AdNS3NS4+AdNS5b+AdNS5a (2nd group), AdNS3NS4+AdNS5b+AdCEIE2 (3rd group) and AdβGal (4th group).

The results, given in FIG. 6, are treated statistically on the basis of the Wilcoxon Mann-Whitney non-parametric test (Méthodes Statistiques à l'usage des médecins et des biologistes, Collection Statistique en Biologie et en Médecine, Flammarion Medecine Sciences, (D. Schwarz), 1977), which is based on a comparison of the averages, and allows the comparison of the values of two independent samples x and y.

This test is implemented as follows: all of the values of the two groups x and y to be compared are classified in increasing fashion. A rank is then allocated to each value, and the sum of the ranks is calculated. Wx and Wy are then obtained. A reference value called $(Wx)_t$ (theoretical value in the null hypothesis where Wx is not different from Wy) is then calculated and linked by the ratio: n (N+1)/2, with n=number of mice tested in group x and N=number of mice tested in groups x and y.

If $W_x$ is less than $(Wx)_t$ (low residual level of vaccinia virus in the mice), then it can be concluded that the neutralization resulting from the vaccination is significantly effective.

If we take the example of the group AdNS3NS4S5b denoted x compared with the group AdβGal denoted y, we obtain the following values:

$Wx=1+2+4+6+8+11+13+14=59$ (8 mice tested)

$Wy=3+5+7+9+10+12+15+16=77$ (8 mice tested)

Under the null hypothesis, Wx is not different from Wy, the expected value is: $(Wx)_t=(\frac{1}{2})*8*17=68$ Wx<$(Wx)_t$, which signifies that the values obtained in the group AdNS3NS4NS5b are smaller than those obtained in the group AdβGal and that the neutralization resulting from the vaccination is significantly effective.

The statistical values for the other groups of mice are indicated in Table 1 below:

TABLE 1

| Group/AdβGal | Wx | $(Wx)_t$ |
|---|---|---|
| AdNS3NS4 + NS5b | 52 | 68 |
| AdNS3NS4 + NS5b + NS5a | 68 | 68 |
| AdNS3NS4 + NS5b + CE1E2 | 74 | 68 |

The values in Table 1 above show that only a vaccination of the mice by a combination of the Adenoviruses NS3NS4 and adenovirus NS5b is capable of inducing a significant neutralization of the replication of the vaccinia virus used in the trial with respect to the group of control mice vaccinated by AdβGal. The vaccinations carried out using the combinations comprising (AdNS3NS4+AdNS5b+AdNS5a) or (AdNS3NS4+AdNS5b+AdCE1E2), do not result in a significant difference compared with the group of control mice immunized by AdβGal.

These results therefore make it possible to demonstrate, unexpectedly, the superior protection of a vaccination combining the polyprotein NS3NS4 and the polypeptide NS5b.

5. Confirmation of the Protection of a Vaccination Combining the Polyprotein NS3NS4 and the Polypeptide NS5b Expressed Jointly by the Same Vector The recombinant vaccinia virus titre was determined for 3 groups of 8 mice immunized by the following combinations of adenoviruses: AdNS3NS4AdNS5b (1st group), AdNS3NS4+AdNS5b (2nd group), and AdβGal (3rd group).

The results, given in FIG. 7, are treated statistically on the basis of the Wilcoxon Mann-Whitney non-parametric test as described in the previous experiment.

The statistical values for groups 1 and 2 compared to the control group AdβGal are indicated in Table 2 below:

TABLE 2

| Group/AdβGal | Wx | $(Wx)_t$ |
|---|---|---|
| AdNS3NS4NS5b | 49 | 68 |
| AdNS3NS4 + NS5b | 53 | 68 |

The values in Table 2 above show that the vaccination of the mice by an adenovirus coding both for the three antigens NS3, NS4 et NS5b, like the combination of the Adenovirus NS3NS4 and Adenovirus NS5b, is capable of inducing a significant neutralization of the replication of the vaccinia virus used in the trial with respect to the group of control mice vaccinated by the AdenoβGal. This result confirms the protection of a vaccination combining the polyprotein NS3/NS4 and the polypeptide NS5b expressed jointly by the same vector.

EXAMPLE 4

Accelerated Immunization Schedule Induces Potent, Long-Lasting and Cross-Protective T Cell Response The MVA vectored vaccine candidate expressing three viral antigens described in Example 2 was evaluated in HLA-class I transgenic mouse models for its ability to stimulate CD8+ and CD4+ mediated responses. An accelerated (3 weekly-based) vaccination induced specific CD8+ T cells harboring two effector functions (cytolytic activity—both in vitro and in vivo- and production of IFN-γ) and well as specific CD4+ T cells recognizing all three viral antigens. Responses were long lasting (6 months), boostable by a 4th MVA vaccination and cross-protective as demonstrated in a surrogate *Listeria*-based challenge assay.

1. Introduction

Approximately 3% of the world's population is infected with hepatitis C virus (HCV) (Shepard et al., 2005, Lancet 5558-5567) and about 80% of infected people develop a chronic infection leading to liver failure in 4% cases. Standard treatment combining interferon α (IFNα) and ribavirine is effective in about half of the treated patients, however associated with significant toxicity and cost, and remains counter-indicated in a non-neglectable number of cases. Novel therapies are in development, mainly targeting the viral protease or polymerase (Dev et al., 2004, Current Gastroenterology Reports 677-686). However, preliminary clinical data indicate that these new antivirals display low efficiency when used as stand-alone therapy, and it is becoming clear that the HCV therapeutic field is moving towards a complex association of multiple, costly drugs. The need for alternative therapeutic strategies, relying on complementary mechanisms than those currently exploited by antiviral molecules candidate, is well recognized.

Studies in humans and chimpanzees have indicated that failure to generate broad and long-lasting HCV specific CD4+ and CD8+ T lymphocytes-mediated immune responses during the acute phase of infection correlates with development of chronicity (Shoukry et al., 2004, Annual Review of Microbiology, 58391-58424). Conversely, patients displaying a functional and maintained Th1 CD4+ T lymphocyte-mediated response, associated with the mounting of matured and multifunctional effector CD8+ T lymphocytes, exert a more efficient control of viremia and are prone to evolve towards recovery (Lauer et al., 2004, Gastroenterology 127(3), 924-936); Urbani et al., 2001, Hepatology 33, 1533-1543; Lechner et al., 2000, J. Exp. Med. 191, 499-512; Thimme et al., 2001, J. Exp. Med. 194, 1395-406; Bowen et al., 2005, Nature 436, 946-52; Cox et al., 2005, Hepatology 42, 104-112). Multiple studies have established that non structural antigens, and in particular NS3, are the preferential targets of responses associated with natural or therapeutic viral clearance (Vertuani et al., 2002, Eur. J. Immunol. 32, 144-54; Diepolder et al., 1997, J. Virol. 71, 6011-9; Smyk-Pearson et al., 2006, J. infect. Dis. 194, 454-63). In contrast, although the field is moving quickly due to novel assays recently developed, the contribution of anti-HCV antibodies in infection outcome remains controversial as these antibodies are typically present in face of ongoing chronicity (Bartosch et al., 2003, Proc. Natl. Acad. Sci. USA, 100, 14199-204; Logvinoff et al., 2004, Proc. Natl. Acad. Sci. USA 101, 10149-54; Maunier et al., 2005, Proc. Natl. Acad. Sci. USA 102, 4560-5).

Over the last ten years, a wide variety of HCV vaccine efforts have been pursued. Various formulations, ranging from classical adjuvanted-recombinant proteins to dendritic cell-based vaccines, have been tested in mice, macaques and for a few, in chimpanzees (Martin et al., 2006, Drug Discovery Today 3206-9). It is striking to observe that only a few vector-based vaccines have been evaluated so far such as recombinant DNA (Forns et al., 1999, Vaccines 17, 1992-2002; Rollier et al., 2004 J. Virol. 78, 187-96), recombinant bacteria (Wedemeyer et al., 2001, Gastroenterology 121, 1158-66) or adenoviruses (Arribillaga et al., 2002, Vaccine 21, 202-210; Folgori et al., 2006, Nature Medicine 12, 190-7). Most surprisingly, one of the safest known vaccine vector used to-date in the clinic, namely the modified non-replicative vaccinia virus Ankara strain (MVA), has seldom been evaluated towards the development of HCV vaccines. This highly attenuated strain of vaccinia virus, that has been used in the campaign for eradication of smallpox, has demonstrated a safety profile in more than 100,000 people (Mayr et al., 1978, Zentralbl. Bakteriol. 167, 375-90; Mahnel et al., 1994, Bert. Muench. Tieraerztl. Wochenschr. 107, 253-6). In the case of HCV, only two pre-clinical studies based on MVA vaccines have so far been reported: one describing MVA candidates expressing HCV envelop glycoproteins E1 and E2, either as wild-type or membrane targeted immunogens (Abraham et al., 2004, Vaccine 22, 3917-28), the other reporting on a vaccine combining two MVA expressing the three structural proteins (Core, E1 and E2) as well as the non structural protein 3 (Rollier et al., 2004, J. Virol 78, 187-96). However, encouraging results with MVA-based vaccines have been observed for example, in the field of HIV or malaria vaccine development, where numerous studies involve MVA vaccine candidates either used alone or in prime-boost combinations (Hanke et al., 1998, J. Gen. Virol; 79, 83-90; Gilbert et al., 2002, Vaccine 20, 1039-45; Prieur et al., 2004, Proc. Natl. Acad. Sci. USA 101, 290-5). These studies have run from evaluations performed in HLA-A2 transgenic murin models to small non-human primates and to clinical trials (Hanke et al., 2007, J. Gen. Virol. 88, 1-12; Webster et al., 2005, Proc. Natl. Acad. Sci. USA 102, 4836-41). Another poxvirus that has been tested in the HCV vaccine field is a HCV recombinant canarypox virus reported to induce potent T cell immune responses although this candidate has been only tested in a DNA prime-canarypox virus boost regimen (Pancholi et al., 2000, J. Infect. Dis. 182, 18-27). The superior safety profile of MVA combined with its powerful immunogenic potential, argue unambiguously in favour of developing a potent HCV MVA-based vaccine, both for prophylactic and therapeutic application.

With the aim to develop a safe, poly-antigenic, T cell-based HCV vaccine, we have engineered and pre-clinically evaluated a recombinant MVA vaccine candidate encoding for HCV non structural (NS) proteins NS3, NS4 and NS5B. We report here that an accelerated schedule of vaccination using this vaccine is able to induce CD4+ and CD8+ T lymphocytes-mediated responses targeted at all three vaccine immunogens and recognizing class I T cell epitopes recognized during the natural infection. Potent and specific CD8+ T cell-mediated responses are long lasting (detectable up to 6 months) and can be efficiently recalled when boosted at a later time with the original MVA NS34-NS5B. Using a challenge model based on HCV recombinant *Listeria monocytogenes* that can infect liver, we show that the accelerated schedule of vaccination with the MVA NS34-NS5B results in in vivo, cross-protective responses.

2. Materials and Methods 2.1. Synthetic Peptides and Recombinant Proteins

All synthetic peptides and recombinant proteins used were derived from a genotype 1b sequence (HCV-JA) (Kato et al., 1990, Proc. Natl. Acad. Sci. USA 87, 9524-8). Peptides (Eurogentec) were derived from NS3: CVNGVCWTV (referred as CVN, corresponding to aa 1073 to 1081 on the HCV polyprotein; SEQ ID NO: 28), GLLGCIITSL (GLL, aa 1038 to 1047; SEQ ID NO: 24), KLTGLGLNAV (KLT, aa 1406 to 1415; SEQ ID NO: 29), WPAPPGARSM (WPA10, aa 1111 to 1121: SEQ ID NO: 30), LSPRPVSYLK (LSP10, aa 1152 to 1162; SEQ ID NO: 31) or NS5B: ALYDVVSTL (ALY, aa 2594 to 2602; SEQ ID NO: 25) antigens. A peptide derived from the HCV Core: DLMGYIPLV (DLM, aa 132 to 140; SEQ ID NO: 27) was used as irrelevant peptide. Peptides were dissolved in 100% DMSO at a concentration of 10 mM and stored at −20° C. until use. Recombinant NS3 helicase (aa 1192 to 1457) and NS5B (aa 2420 to 2989) proteins were expressed in-house in E. Coli and produced endotoxin-free with a purety >95%. Recombinant NS4 protein was obtained from Mikrogen. Tetanus toxoid (TT, Sanofi Pasteur) was used as irrelevant protein.

2.2. Construction of Recombinant MVA NS34-NS5B

Plasmid used for homologous recombination in the so-called deletion III corresponding site of the MVA genome was based on plasmid pTG1E (Braun et al., 2000, Gene Ther. 7, 1447-57). Flanking sequences (BRG3 and BRD3) surrounding the deletion III were amplified by PCR from MVA N33 DNA (Sutter and Moss, 1992, Proc. Natl. Acad. Sci. USA 89, 10847-51). The transfer plasmid also contained a fusion between the Aequorea victoria enhanced Green Fluorescent protein (eGFP gene, isolated from pEGP-C1, Clontech) and the E. coli xanthine-guanine phosphoribosyltransferase gene (gpt gene) under the control of the early/late vaccinia virus synthetic promoter p11K7.5 (kindly provided by R. Wittek, University of Lausanne). Synthesis of xanthine-guanine phosphoribosyltransferase enabled GPT$^+$ recombinant MVA to form plaques in a selective medium containing mycophenolic acid, xanthine, and hypoxanthine. eGFP enables the visualisation of recombinant MVA plaques. When the clonal selection was achieved, the selection marker eGFP-GPT, placed between two homologous sequences in the same orientation, was eliminated by several passages without selection. Gene sequences coding for NS3NS4 and NS5B from HCV genotype 1b HCV-JA strain were amplified by PCR. NS3NS4 gene was inserted in the transfer plasmid downstream the pH5R promoter (Rosel et al., 1986, J. Virol. 60 436-49) giving rise to pTG16639. NS5B gene was inserted downstream the p7.5K promoter (Cochran et al., 1985, J. Virol. 54, 30-7) in the same orientation as NS3NS4 gene in pTG16639, giving rise to the final transfer plasmid pTG16643. Generation of MVA NS34-NS5B (MVATG16643) was performed by homologous recombination in primary chicken embryo fibroblasts (CEF). pTG16643 was transfected according to the standard calcium phosphate DNA precipitation on to CEF previously infected with MVA N33 at a MOI of 0.1 pfu/cell. Viral selection was performed by three rounds of plaque purification in the presence of a selective medium containing mycophenolic acid, xanthine and hypoxanthine on CEF, then the selection marker was eliminated by passage in non-selective medium. Absence of contamination by parental MVA was verified by PCR.

2.3. In Vitro Expression Studies

Expression of NS3, NS4 and NS5B antigens was examined by immunofluorescence and flow cytometry following MVA NS34-NS5B infection of human Huh-7 hepatoma cells. For immunofluorescence analysis, glass coverslips were placed into 6-well plates treated with 0.2% Gelatin for 10 min prior to plating Huh-7 cells ($10^6$ per well) into wells. Cell monolayers were infected with MVA vectors (MVA NS34-NS5B or MVA N33 as negative control) at a MOI of 0.33. Twenty four hours later, coverslips were washed in PBS, fixed with 4% PFA and permeabilized with 0.1% Triton X-100 in PBS. Primary antibodies were applied for 1 h at room temperature (rabbit polyclonal anti-NS4B serum and murine monoclonal anti-NS5B antibody 5B12b7 kindly provided by R. Bartenschlager and D. Moradpour respectively). Alexa-Fluor 488 chicken anti-mouse IgG (Molecular Probes) and Cy3-conjugated anti-rabbit IgG sheep (Fab)2 (Sigma) were then added for 30 min. Coverslips were mounted in 80% glycerol in presence of 10 µg/ml Hoechst and strips were observed with Carl Zeiss Axioplan microscope. Images were taken with AxioCam Color digital camera. For flow cytometry analysis, $10^6$ Huh-7 cells per well, plated into 6-well plate, were infected with MVA vectors at a MOI of 1. Twenty four hours later, cells were harvested, fixed with Cytofix/Cytoperm reagent (Becton Dickinson) for 10 min and washed with PermWash reagent (Becton Dickinson). Staining was performed using monoclonal anti-NS3 antibody 8D8E1 (bioMerieux), anti-NS4B antibody 1B12A3 (bioMerieux) and anti-NS5B antibody 5B12b7 (provided by D. Moradpour) added to $2.10^5$ cells for 30 min at room temperature. RPE-conjugated rabbit anti-mouse IgG (Dako) was then added for 30 min at room temperature. Cells were resuspended in 1% FCS-PBS and analyzed by flow cytometry using a FacsCalibur cytometer (Becton Dickinson).

2.4. Mice

Commercial Balb/c (Charles River) and H-2 class I knock-out HLA-A2.1 and HLA-B7.2 transgenic mice were used. HLA-A2.1 mice expressed a transgenic monochain histocompatibility class I molecule in which the C-terminus of the human β2m is covalently linked to the N-terminus of a chimeric heavy chain (HLA-A2.1 α1-α2, H-2D$^b$ α3 transmembrane and intracytoplasmic domains) (Pascolo et al., 1997, J. Exp. Med. 185, 2043-51). HLA-B7.2 mice expressed a chimeric HLA-B*0702 heavy chain composed of human HLA-B*0702 α1-(2 domains with a murine H-2 Db (3 domain (Rohrlich et al., 2003, International Immunol. 15, 765-72). Mice were hosted at the PBES (Plateau de Biologie Experimentale de la Souris, Lyon) in appropriate animal care facilities and handled in accordance with international guidelines required for experiments with animals 2.5. Immunization Protocols Six to 8 weeks-old mice (2 to 6 per group) were used in each experiment. First, two MVA immunization schedules were compared. Mice received sub-cutaneous (sc) injections at the tail base with 107 pfu of MVA NS34-NS5B or MVA N33, either 3 injections at 3 weeks-interval (schedule 1) or 4 injections, 3 at 1 week-interval and the 4th one 3 weeks later (schedule 2). A schedule including 3 injections at 1 week-interval was then selected for additional experiments. For analysis of recall memory responses, mice received a 4th MVA injection at 6 months (week 27) after the first immunization.

2.6. ELISPOT Assays

Splenocytes ($2 \times 10^5$ cells per well), treated with red blood cell lysis buffer (Sigma), were cultured in triplicate wells for 40 h in multiscreen nitrocellulose-backed plates (Millipore) coated with anti-mouse IFNγ monoclonal antibody (Pharmingen) in complete αMEM culture medium (GIBCO BRL) supplemented with murine recombinant IL-2 at 10 U/mL (Pedro-Tech EC LTD) alone as negative control or with 10 µM of peptide or 2 µg/ml of protein or 5 µg/ml of Concavalin A as positive control. IFNγ-producing cells were quantified by IFNγ-specific enzyme linked immunospot assay (ELISPOT) as previously described (Martin et al., 2004, J. Med. Virol. 74, 397-405). Positive selection of CD4+ T cells was performed by magnetic cell sorting using CD4(L3T4) microbeads (Myltenyi Biotech) according to the manufacturer's instructions and positive selection efficiency was assessed by flow cytometry and percentage of CD4+ T cells always found superior to 88% with less than 2.1% of CD8+ T cells. Total, CD4+ and effluent fractions were analyzed separately. The number of spots, corresponding to the IFNγ-producing T cells, detected in negative control wells was subtracted from the number of spots detected in experimental wells. Results are shown as the mean value obtained for triplicate wells. A response was considered positive if the number of spots was higher than 40 spots per $10^6$ cells.

2.7. Intracellular Cytokine Staining (ICS)

ICS was performed on splenocytes from individual animals. Briefly, following red blood cells lysis, $2 \times 10^6$ cells per well of flat-bottom 96-well plate were incubated in complete αMEM culture medium supplemented with murine recombinant IL-2 at 10 U/ml alone as negative control or with 10 μM of peptide or 2 μg/ml of protein. After overnight incubation, GolgiStop (Becton Dickinson) was added at a 0.67 μl/ml final concentration for 6 h. Cells were then harvested in V-bottom 96-well plates and washed with 1% FCS-PBS. Staining was realized using monoclonal antibodies (MAb) against CD3 (hamster MAb anti-CD3e-PE) and CD8 (rat MAb anti CD8a-APC) (all from Becton Dickinson) in 1% FCS-PBS for 15 min at room temperature. After washing, cells were fixed and permeabilized with Cytofix/Cytoperm (Becton Dickinson) and washed twice with Perm/Wash solution. Anti-mouse IFNγ-Alexa488 antibodies (Becton Dickinson) were added for 15 min at room temperature and after washing, cells were resuspended in PBS and analyzed by flow cytometry. $CD3e^+$, $CD8a^+$ cells were gated and represented on IFNγ-Side Scatter-dot-plot and percentages of IFNγ+CD8+ T cell population were determined.

2.8. In Vitro and In Vivo Cytotoxic T Cell (CTL) Assays

Conditions for in vitro CTL assays have been described previously (Brinster et al., 2001, Hepatology 34, 1206-17). Briefly, after restimulation on day 5, CTL assays were performed on day 7 using stimulated cells as effectors. As target cells, $^{51}$Cr-stained EL4S3-Rob HHD cells were used either loaded with 10 μM of the selected peptide or unloaded (negative control). Spontaneous and total lysis were determined from wells containing target cells, loaded with peptide or not, either in medium alone or in lysis buffer (1N HCl), respectively. Specific cytotoxicity was calculated using the formula: (release in assay–spontaneous release)/(total lysis–spontaneous release)×100. For each effector/target ratio, data are expressed as the mean of duplicate results. A response was considered positive if the percentage of specific lysis was greater than 20% and at least 10% superior to that obtained for MVA N33 immunized mice.

In vivo CTL assays were performed as described (Beloeil et al., 2003, J. Immunol. 171, 2995-02), with minor modifications. Briefly, splenocytes suspensions were obtained from syngenic mice and adjusted to $20 \times 10^6$ cells/ml after lysis of red blood cells. One half of the cells were incubated with GLL peptide at 10 μM final concentration for 1 h at 37° C., whereas the second fraction was left unpulsed. 5(6)-carboxyfluorescein diacetate succinimidyl ester (CFSE) (Molecular Probes) was then added at 1 μM ($CFSE^{low}$) to unpulsed cells and at 10 μM ($CFSE^{high}$) to peptide pulsed cells for 10 min. After washing, both populations were mixed and $20 \times 10^6$ total cells were transferred to mice by retro-orbital intravenous injection. Thus, $CFSE^{high}$ population represented specific targets supposed to be lyzed by CTL and $CFSE^{low}$ population was an internal reference allowing assay normalisation. Splenocytes from recipient mice were analyzed 24 h later by flow cytometry to detect the CFSE-labeled target cells. The ratio between peptide-pulsed targets and unpulsed targets injected in a given mouse (ratio R=number of $CFSE_{high}$ cells/number of $CFSE_{low}$ cells) was calculated. The percentage of specific lysis, that normalized cytolytic activity between MVA NS34-NS5B and MVA N33 immunized mice (control), was determined by the following formula: % of specific lysis=[1−(R immunized/R control)]×100% where R control is the highest ratio R obtained for 2 MVA N33 injected mice.

2.9. Protective Immunity in Surrogate Challenge Model

Protection was assessed using a surrogate challenge model based on a recombinant *Listeria monocytogenes* strain producing an HCV NS3 protein derived from a genotype 1a sequence (HCV-1 isolate): TC-LNS3 (Simon et al., 2003, Infection and Immunity 71, 6372-80). MVA NS34-NS5B immunized mice received an i.v. injection with 1 $LD_{50}$ ($9.10^7$ colony-forming units (CFU) for mice with a C57BL6 background like HLA-A2 mice, $3.10^7$ CFU for Balb/c mice) of TC-LNS3 in 100 μl of PBS 2 weeks following the last MVA immunization. As negative control group, MVA N33 immunized mice were used and as positive control group, we used mice that were immunized 1 or 2 times at 2 weeks-interval with 0.05 to 0.1 $LD_{50}$ of TC-LNS3 (immunization dose). Two days after bacterial challenge, spleens and livers were removed from individual mice, weighted, homogenized and serially diluted in PBS/0.1% Triton. These dilutions were plated out on brain heart infusion agar. Following 2 to 3 days at room temperature, the number of CFU was calculated and results given in Log CFU/mg of tissue values from individual mouse.

2.10. Statistical Analyses

Analyses of CTL responses, IFNγ ELISPOT responses and protective effect were conducted by using a Mann-Whitney test.

3. Results 3.1. Design and In Vitro Expression of a Single Recombinant MVA Encoding for HCV NS3, NS4 and NS5B Proteins Two recombinant MVA vectors, encoding each HCV NS3NS4 proteins under the ph5r promoter and NS5B protein under the p7.5 promoter, were designed. Both expression cassettes were cloned in the deletion III of the MVA backbone, either in same or in opposite orientation. Western blot analysis revealed an enhanced expression of all three cloned antigens when the two expression cassettes were inserted in the same orientation (data not shown). Thus, the MVA vector containing both expression cassettes in the same orientation, referred to as MVA NS34-NS5B, was selected for further studies. In vitro NS3, NS4 and NS5B antigen expression was characterized by flow cytometry and immunofluorescence analyses following MVA NS34-NS5B infection of Huh-7 cells. Flow cytometry analyses showed clear expression of the three antigens (FIG. 8). While the percentage of expressing cells following infection appeared identical for the three encoded antigens, measure of mean fluorescence intensity (MFI) suggested a weaker expression of the NS5B likely due to a lesser strength of the p7.5 promoter compared with the ph5r promoter. Co-localisation of the expressed antigens in the cytoplasm of infected cells was expected based on known properties of the antigens (Penin et al., 2004, Hepatology 39, 5-19) and was indeed confirmed in immunofluorescence analyses.

Figure 9A:
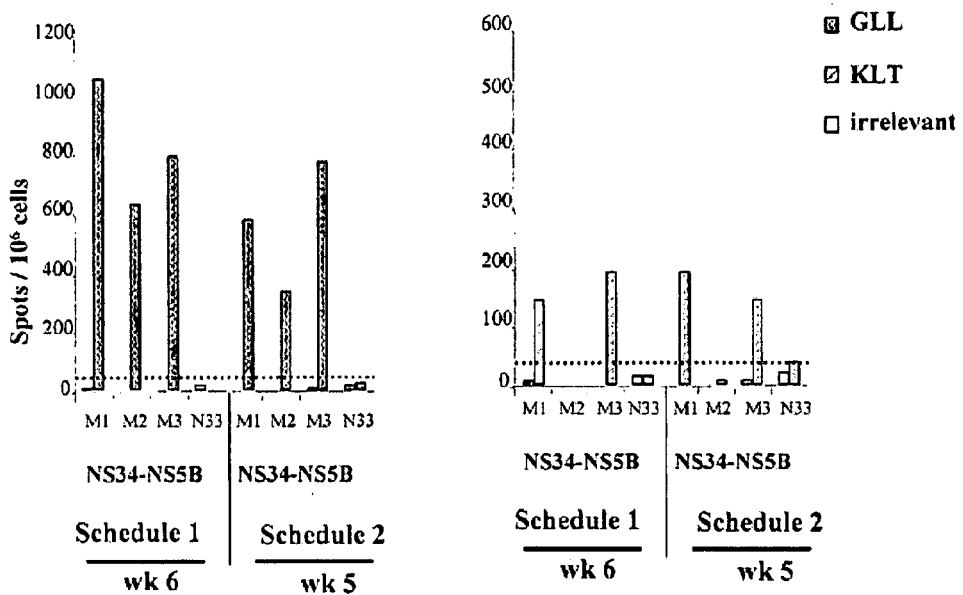
Figure 9B:
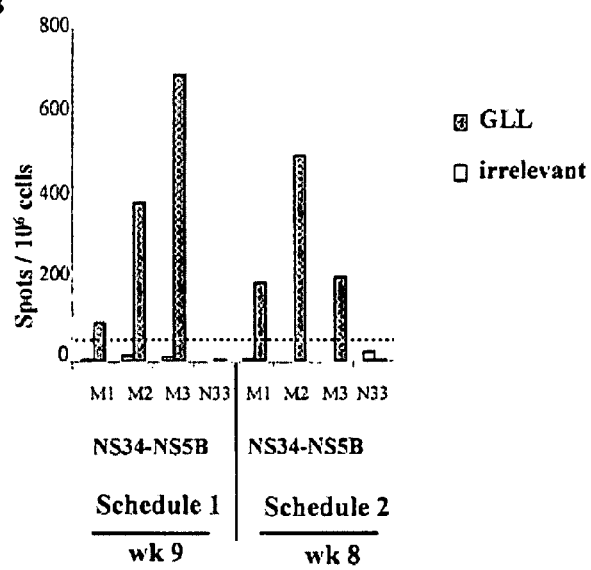
Figure 10B:
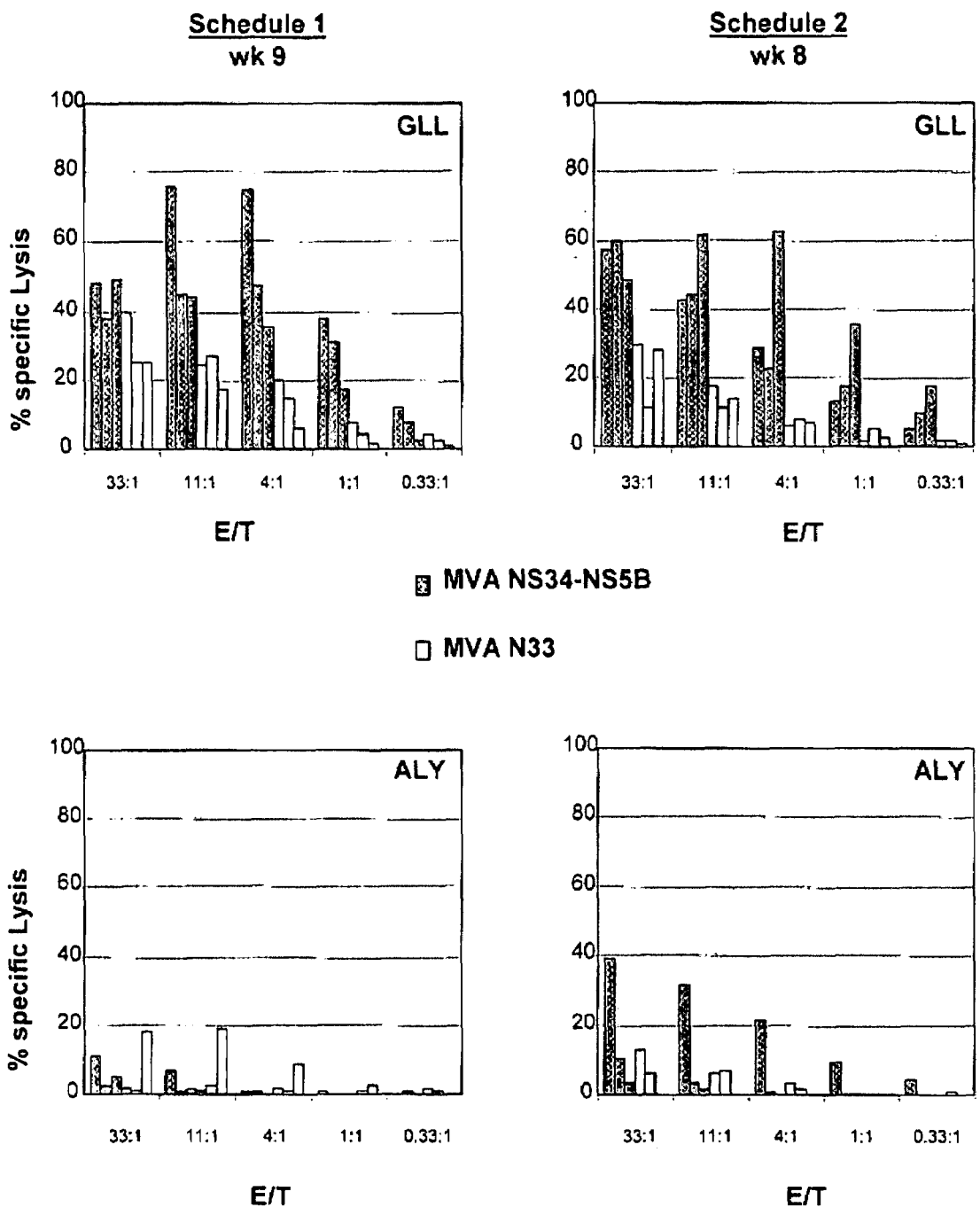
Figure 11A:
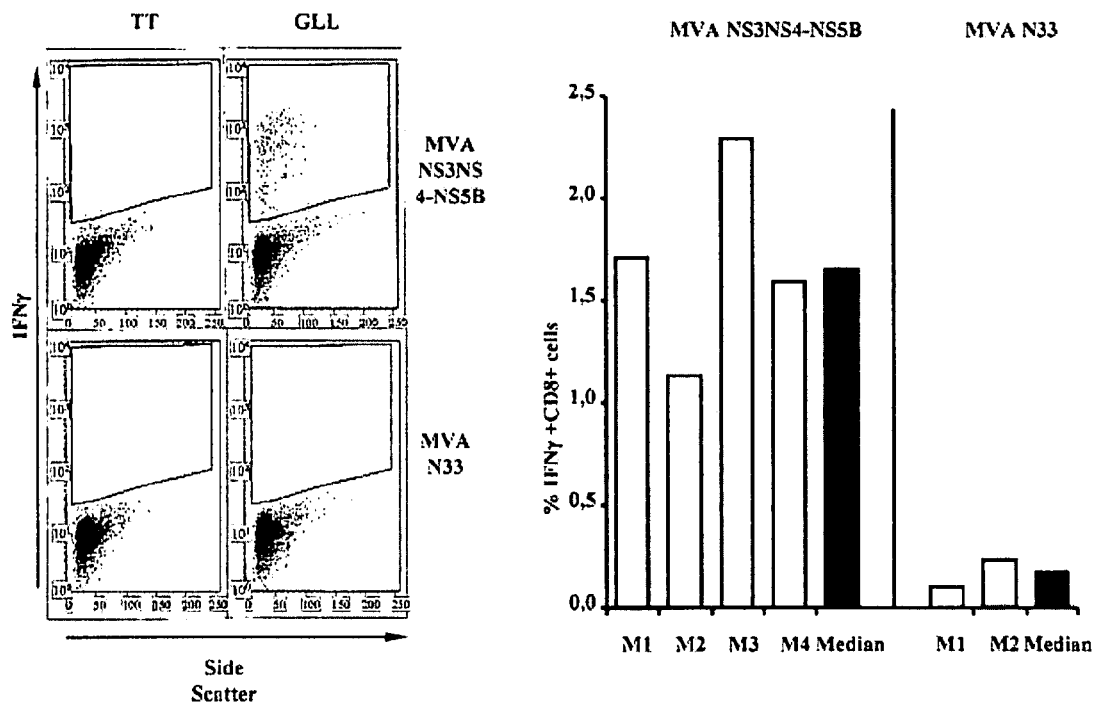
Figure 11B:
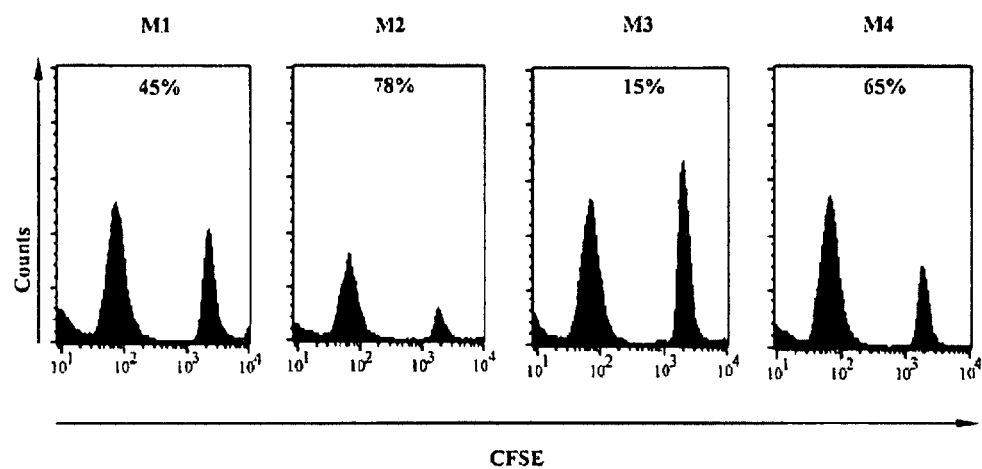

3.2. An Accelerated Vaccination Schedule with the MVA NS34-NS5B Induces Specific CD8+ T Cells Displaying Two Effector Functions Comparable with those Obtained Following a More Lengthy Classical Schedule The mounting of immune responses following MVA-based vaccination has typically been analyzed following 2-3 injections of candidate vaccines performed 2-4 weeks apart (Gilbert et al., 2002, Vaccine 20, 1039-45; Vazquez-Blomquist et al., 2004, Biotechnol. Applied Biochem. 39, 313-8). Yet, it may be worthwhile to indeed quickly mount specific immune responses to try to minimize impact of vector-developed anti-immunity as well as to have a faster impact on viral load and/or disease evolution in cases of therapeutic vaccination. Based on recent, highly encouraging data obtained in the clinics with a HPV (human papilloma virus)-based MVA vaccine administered according to an accelerated schedule (Transgene Abstract, EUROGIN 2006), we decided to first compare side by side two different schedules of vaccination. HLA-A2 transgenic mice received, subcutaneously, either 3 injections at 3 weeks-interval (schedule 1) or 3 injections at 1 week-interval followed by a $4^{th}$ injection, 3 weeks later (schedule 2) of $10^7$ pfu MVA NS34-NS5B or MVA N33 (wild type virus used as negative control). Induced CD8+ T cell responses were investigated by in vitro CTL and IFNγ ELISPOT assays at two time points for each schedule, either 2 weeks after the $2^{nd}$ and the $3^{rd}$ injection for schedule 1 (week 6 and 9) or 2 weeks after the $3^{rd}$ and $4^{th}$ injection for schedule 2 (week 5 and 8) (FIG. 9). As shown in FIG. 9A, both injection schedules resulted in the induction of IFNγ-producing cells specific for two HLA-A2 restricted epitopes (GLL and KLT) located in the NS3 protein and known to be recognized during natural infection (Martin et al., 2004, J. Med. Virol. 74, 397-405; Ward et al., 2002, Clin. Exp. Immunol. 128, 195-203). A similar number of spots was observed with both schedules: an elevated number was observed for the GLL epitope (up to 1000 spots), in agreement with observations describing GLL as a dominant epitope in HLA-A2 mice (Martin et al., 2004, J. Med. Virol. 74, 397-405), while responses were weaker against the KLT epitope (up to 200 spots). Although the frequency of GLL specific positive cells waned with time and was found lower two weeks after the final injection for both schedules (week 9 for schedule 1 and 8 for schedule 2, FIG. 9B), the overall observed number of spots remained comparable for both schedules. The KLT specific response was at that time lost (data not shown). High cytotoxic activity was detected against the GLL peptide using both schedules at the first time point studied (week 6 for schedule 1 and week 5 for schedule 2) (FIG. 10A), while lower percentages of specific lysis were observed after last boosting (week 9 and 8) (FIG. 10B). A weak but specific cytotoxic activity targeted at the subdominant NS5B ALY epitope was detected for 2 mice after 3 injections (FIG. 10A) and 1 mouse after 4 injections following schedule 2 (FIG. 10B). Overall, these results suggest that 2 injections at 3-weeks intervals induced similar NS3 specific cytotoxic activities and frequencies of IFNγ-producing T cells than those obtained by 3 injections at 1 week-interval. An additional booster injection, independent of the schedule (the $3^{rd}$ injection for schedule 1 or the $4^{th}$ for schedule 2), did not enhance these responses. Further experiments were then performed based on vaccination schedule 2, referred to as "accelerated" immunization schedule.

3.3. Accelerated Vaccination with the MVA NS34-NS5B Induces Significant Percentage of CD8+ T Cells Producing IFNγ and Displaying Potent In Vivo Lytic Activity To further characterize the immunogenicity of the accelerated vaccination schedule, we investigated, in HLA-A2 transgenic mice, the capacity of induced CD8+ T cells to produce IFNγ by intracellular IFNγ cytokine staining (ICS) as well as their cytotoxic potential in vivo. ICS analysis, performed 2 weeks after the $3^{rd}$ injection (FIG. 11A), indicated that all 4 immunized animals displayed a high percentage of GLL specific-CD8+ T cells producing IFNγ (ranging from 1.13 to 2.3%, median percentage of 1.7%). We examined the in vivo killing capacity of specific effector CD8+ T cells by transferring CFSE-labeled target splenocytes pulsed with GLL peptide into MVA NS34-NS5B or MVA N33 immunized mice, 2 weeks after the $3^{rd}$ injection. After transfer, GLL-pulsed targets were eliminated efficiently in the MVA NS34-NS5B immunized mice (FIG. 11B: lysis of 15%, 45%, 65% and 78% for each mouse, respectively) in a 20 h-assay, whereas CTL activity was undetectable in control mice (not shown). Overall, these results confirm that CD8+ T cells induced in mice immunized with the MVA NS34-NS5B on a weekly basis have acquired significant capacity to produce IFNγ and to display a cytolytic activity in vivo.

3.4. Accelerated Vaccination with MVA NS34-NS5B is Capable to Induce Responses Targeting HLA-B7 Restricted Epitopes It was recently reported that HLA-B restricted immune responses may play a major role in the outcome of HCV infection (Neumann-Haefelin et al., 2006, Hepatology 43, 563-72), similar to what has been described for HIV and EBV (Frahm et al., 2005, J. Virol. 79, 10218-25; Kiepiela et al., 2004, Nature 432, 769-75; Bihl et al., 2006, J. Immunol. 176, 4094-101). To address the capacity of the MVA NS34-NS5B to prime, in vivo, cellular immune responses restricted by an HLA-B molecule, HLA-B7 trangenic mice were immunized following the accelerated schedule and CD8+ T cell response investigated using IFNγ ELISPOT assay. As shown in FIG. 12, the vaccine was able to prime significant IFNγ-producing T cells specific of two HLA-B7 restricted epitopes that are the only NS3 HLA-B7 epitopes so far described in HCV infection, namely WPA10 and LSP10 (Martin et al., 2004, J. Med. Virol. 74, 397-405). In 4 (WPA10) to 5 (LSP10) out of 5 immunized animals, IFNγ-producing T cells were detected with a high frequency for WPA10 (median value: 305 spots/ $10^6$ splenocytes), and with a weaker frequency for LSP10 (median value: 160 spots/$10^6$ splenocytes). These results demonstrate the capacity of the MVA NS34-NS5B to induce, in addition to HLA-A2 restricted responses, HLA-B7 restricted responses specific of epitopes recognized in a HCV natural infection.

3.5. CD4+ T Cell Responses Specific of all Three Immunogens Expressed by the MVA NS34-NS5B are Induced Following Accelerated Immunization Due to the critical role of CD4+ T cell mediated responses in determining the outcome of HCV infection, it is of obvious importance that HCV vaccine candidates harbour the capacity to generate such responses. We assessed the ability of the MVA NS34-NS5B to induce, following the "accelerated" schedule of administration, specific CD4+ T cell responses in Balb/c mice as such responses were difficult to detect in HLA-A2 or -B7 mice, both displaying a C57Bl6 genetic background (data not shown). The CD4+ T cell responses were evaluated 2 weeks after the $3^{rd}$ immunization by IFNγ-ELISPOT and ICS analysis performed on total splenocytes, the CD4+ T cell positive fraction as well as the effluent fraction obtained after positive selection. As shown in FIG. 13, IFNγ-producing cells specific of each NS3, NS4 and NS5B protein were detected using the purified CD4+ T cell fractions obtained from immunized mice, while no signals could be seen in control animals. A weak IFNγ ELISPOT response specific of NS4 was also detected using the total splenocyte fraction. ICS analysis led to similar results (data not shown). Overall, these data reveal that a weekly administration of the MVA NS34-NS5B is able to induce CD4+ T cells specific of all three expressed antigens.

3.6. CD8+ T Cell Specific Responses Induced Following Accelerated Vaccination with MVA NS34-NS5B are Long Lasting and can be Boosted A key feature common to potent vaccines is their potential to induce long lasting, memory responses. To evaluate the longevity of MVA NS34-NS5B CD8+ T cell responses induced following accelerated vaccination, a two steps-experiment was performed. The first step evaluated the longevity of responses by performing CTL and IFNγ ELISPOT assays at 1 month (week 5), 2 months (week 10) and 6 months (week 27) post primary injection. In a $2^{nd}$ step, the capacity of a $4^{th}$ MVA NS34-NS5B injection to recall memory responses was explored, using the same assays, 2 weeks after a recall injection performed 6 month post primary vaccination (week 29). CTL responses induced at week 5, 10, 27 and 29 are represented in FIG. 14. Strong CTL responses specific of the GLL peptide were detected in all mice, at each time point studied, even at low effector/target cell ratios (median values at an E/T ratio of 11/1:68% of lysis at week 5, 73% at week 10, 47% at week 27). Responses detected 2 weeks after the $4^{th}$ MVA NS34-NS5B injection remained similar to those measured before this injection (median value at an E:T ratio of 11/1:51% of lysis). No obvious anamnestic response could be seen. IFNγ ELISPOT responses induced at week 5, 10, 27 and 29 are represented in FIG. 15. The vaccine was able to induce high frequencies of IFNγ-producing T cells specific of the GLL peptide in all injected mice, at each time point studied (FIG. 15A). The number of specific cells remained statistically similar (p>0.05) between week 5 and 10 and a decrease was observed at week 27 (p<0.05), although responses remained clearly detectable at that time (median values: 655 spots/$10^6$ splenocytes at week 5, 529 at week 10 and 230 at week 27). A $4^{th}$ injection, performed 6 months post primary injection, led to a strong enhancement of the frequency of IFNγ-producing cells (median value: 1049 spots/$10^6$ splenocytes at week 29). In addition, IFNγ-producing T cells specific of 2 other HLA-A2-restricted peptides of NS3 (CVN and KLT) were detected at week 27 in 2 out of 4 mice (FIGS. 15B and 15C). Although weak, these responses were maintained at a quite comparable level after the $4^{th}$ injection (median values for CVN: 112 spots/$10^6$ splenocytes at week 27 and 145 at week 29; median values for KLT: 63 spots/$10^6$ splenocytes at week 27 and 156 at week 29). These results reveal that a weekly vaccination with the MVA NS34-NS5B induced long lasting CTL and IFNγ-producing T cells detectable up to 6 months. In addition, a $4^{th}$ immunization performed at 6 month lead to a significant recall of IFNγ-producing T cells.

3.7. Accelerated Vaccination with the MVA NS34-NS5B Induces In Vivo Protective Responses in a Surrogate Challenge Assay Because hepatocytes represent the main replication site for HCV, one of the goals of a HCV vaccine is to induce T cells able to migrate to the liver and destroy antigen expressing cells. We used a surrogate challenge model mimicking to some extent HCV infection to investigate the capacity of the MVA NS34-NS5B vaccine at generating such desirable response. The challenge agent, a recombinant Listeria monocytogenes expressing the NS3 protein from an HCV genotype 1a strain (referred to as TC-LNS3), (Simon et al., 2003, Infection and Immunity 71, 6372-80), was used as these bacteria are able to infect and replicate within hepatocytes (Jiang et al., 1997, 158, 287-93). Numerous studies have shown that a strong antigen-specific CD8+ T cell response is required for protection against L. monocytogenes infection (Simon et al., 2003, Infection and Immunity 71, 6372-80; Baldridge et al., 1990, Infection and Immunity 58, 654-58). HLA-A2 transgenic mice were immunized according to the accelerated immunization schedule with MVA NS34-NS5B or MVA N33. A group of mice, immunized intravenously 1 or 2 times at 2 weeks-interval with a low immunization dose (0.05 to 0.1 $LD_{50}$) of TC-LNS3 (able to protect mice against a further infection with a high challenge dose of TC-LNS3 (Simon et al., 2003, Infection and Immunity 71, 6372-80)) was included as positive control-immunized mice. MVA vaccinated mice were challenged intravenously with a high challenge dose of TC-LNS3 (1 $LD_{50}$) 2 weeks after the $3^{rd}$ MVA injection. For the positive control group, the challenge was performed 1 week after the $2^{nd}$ injection of the low TC-LNS3 dose as reported (Simon et al., 2003, Infection and Immunity 71, 6372-80). Two days after challenge, the number of viable bacteria in the spleen and liver of each mouse was determined. Experiments were performed in two strains of mice, HLA-A2 and Balb/c mice. The results presented in FIG. 16A show that MVA NS34-NS5B immunized mice exhibited significantly lower bacterial loads in the spleen (median value: 3.83 Log CFU/mg, p=0.02) following challenge than did MVA N33 immunized mice (5.17 Log CFU/mg). These data are representative of 4 independent experiments. In the experiment shown, bacterial counts were also significantly reduced in the liver of MVA NS34-NS5B injected mice (4.53 Log CFU/ml, p=0.02) compared with those of MVA N33 immunized animals (5.62 Log CFU/mg), although reduction in this organ was lower and not always statistically significant i.e. experiment dependent (data not shown). MVA NS34-NS5B Balb/c-immunized mice demonstrated a significant reduction of bacterial loads in the spleen as compared with MVA N33-immunized mice (median value: 2.28 versus 2.89 Log CFU/mg, p=0.006). In this representative experiment, as typically observed in this strain of mice, reduced bacterial counts were also seen in the liver, however differences were not statistically significant (p>0.05). These original data demonstrate that a weekly administration of the MVA NS34-NS5B can prime immune responses capable of confering immune protection against subsequent challenge with recombinant L. monocytogenes expressing HCV NS3 protein in two different mouse species. As the mechanism of protection in this model has been shown to involve effector CD8+ T cells (Baldridge et al., 1990, Infection and Immunity 58, 654-58), these data lead us to conclude that the MVA vaccine is capable of inducing such cells, in particular cells displaying the capacity to migrate and exert their function in the livers of animals. The challenge bacteria used contains a genotype 1a NS3 while the MVA vaccine is expressing a genotype 1b protein thus demonstrating that cross-protective responses can be generated by the vaccine.

4. Discussion

In the present study, we designed a HCV vaccine candidate based on the vaccine strain MVA expressing three HCV antigens, NS3, NS4 and NS5B, from a genotype 1b viral strain (MVA NS34-NS5B). Injected according to an "accelerated" immunization schedule based on 3 injections performed 1 week apart in various HLA-transgenic or commercial mouse models, we show that this candidate vaccine induces simultaneously specific CD8+ T cells able to produce IFNγ and to lyse cells as well as specific CD4+ T cells. We show that the CD8+ T cell responses induced are long lasting responses, detectable up to 6 months post primary vaccination, and boostable with a $4^{th}$ immunization. Finally, cross-protective effects of the MVA NS34-NS5B induced responses were demonstrated in two mouse species using a surrogate challenge assay based on a recombinant HCV NS3 Listeria monocytogenes.

Our strategy for the design and development of a HCV vaccine was based on the fundamental observation that broad, effective and sustained T cell-based immunity is associated with a favorable outcome of infection either spontaneously or therapy-induced (Bowen and Walker, 2005, Nature 436, 946-52). Three key elements guided our approach: the choice of vaccine immunogens containing multiple CD4+ and CD8+ T cell-restricted epitopes, the selection of a safe and efficient vector platform and that of a vaccination schedule capable to rapidly mount an efficient T cell immunity.

The three immunogens encoded by our vaccine were selected on different criteria. NS3 emerged as a mandatory antigen as its contribution to the total magnitude of the HCV specific CD4+ and CD8+ T cell responses found in resolved infection appear to be an essential one (Diepolder et al., 1997, J. Virol. 71, 6011-9; Smyk-Pearson et al., 2006, J. Infect. Dis. 194, 454-63). At least one vaccine study has reported the critical role played by NS3 specific Th1 responses in vaccine-mediated control of HCV viremia in the chimpanzee model (Rollier et al., 2004, J. Virol. 78, 187-96). In contrast to the great majority of NS3-based vaccine studies, that have included NS3 as a stand-alone immunogen (Arribillaga, 2002, Vaccine 21, 202-10; Wedemeyer et al., 2001, Gastroenterology 121, 1158-66; Jiao et al., 2003, Hepatology 37, 452-60; Wuest et al., 2004, Vaccine 22, 2717-21), we have in this report successfully designed a single, stable recombinant MVA (stability observed up to 6 passages), expressing NS3 in association with two other non structural proteins, NS4 and NS5B. NS3 was co-expressed with NS4 as it has been documented that the central part of NS4A is mandatory for proper NS3 folding (Penin et al., 2004, Hepatology 39, 5-19) This was an important feature to maintain as we have previously shown that such co-expression influenced positively the immunogenicity of NS3 (Himoudi et al., 2002, J. Virol. 76, 12735-46). In our configuration, NS5B was expressed as a wild-type antigen and in absence of NS5A. This choice was based on our previous observations indicating that NS5B but not NS5A contained highly immunogenic HLA-A2-restricted T cell epitopes (Himoudi et al., 2002, J. Virol. 76, 12735-46).

MVA was selected over other clinically used vectors for different reasons. No integration of the viral genome in the host DNA is possible as the vaccinia virus lifecycle takes place entirely in the cytoplasm of cells (Moss, 2001, pp 2849-83 in Fields Virology 4$^{th}$ ed. Lippincott-Raven Press). MVA has been attenuated by more than 570 passages in chicken embryo fibroblasts resulting in the loss of about 15% of its genome (Meyer et al., 1991 J. Gen. virol. 72, 1031-38). Consequently, MVA is unable to produce mature virions in most mammalian cells due to a block at the stage of virion formation (Sutter and Moss, 1992, Proc. Natl. Acad. Sci. USA 89, 10847-51) that results in a reduced risk of dissemination (Carroll and Moss, 1997, Virol. 244, 365-96) and an increased immunogenicity due to the loss of several anti-immune defense genes (Sutter and Moss, 1992, Proc. Natl. Acad. Sci. USA 89, 10847-51). Controversial data have been reported concerning the influence of preexisting anti-vaccinia virus immunity on MVA-based vaccine efficacy (Wedemeyer et al., 2001, Gastroenterology 121, 1158-66; Ramirez et al., 2000, J. Virol. 74, 923-33; Belyakov et al., 1999, Proc. Natl. Acad. Sci. USA 96, 4512-7). However, if preexisting immunity has indeed a detrimental effect on MVA vaccine efficacy, this appears minimal compared with that observed in the case of adenoviral vectors. Pre-existing anti-adenovirus immunity to the widely clinically used Ad5 vector is indeed well known to considerably affect efficacy of Ad5-based vaccines (Casimoro et al., 2003, J. Virol. 77, 6305-13).

We have evaluated here an original "accelerated" schedule of vaccination based on different arguments. First, recent very encouraging clinical data have been obtained with a therapeutic HPV-based MVA vaccine administered on a weekly basis (3 times). This phase II trial reports the clearance of HPV viral RNA in women with grade 2/3 dysplasies up to 12 months following vaccination with a MVA expressing the viral E6 and E7 proteins (Transgene Abstract, EUROGIN 2006). These novel data suggest that it may be important, in the optic of development of a therapeutic vaccine, to quickly mount an effective response rather than mounting it over time. Following weekly injection of the HCV MVA NS34-NS5B, we show in mouse models the unambiguous mounting of potent CD8+ T cell responses, displaying two effector functions that are believed to play a role in control of HCV replication (capacity to produce IFNγ and to lyse target cells). In addition, it was particularly interesting to observe that these responses, at least the capacity to produce IFNγ, could be boosted 6 months after the last weekly injection confirming that a long lasting immunological memory state can be developed by a schedule including 3 close MVA immunizations. This feature is a key element both for the development of a preventive and a therapeutic vaccine. It suggests that anti-MVA immunity mounted after the "accelerated" vaccination either waned with time or was not mounted yet to an extent sufficient for affecting vaccine immunity. The capacity of our vaccine to induce long lasting CD8+ responses together with specific CD4+ T cell responses and the fact that overall induced responses were capable to control splenic or hepatic expression of a HCV antigen, are extremely encouraging. Indeed, a recent study performed in a chimpanzee model, has shown that an Ad5 T cell-based vaccine expressing NS3-NS4-NS5A-NS5B antigens was capable to elicit non-sterile yet protective immunity in 4 out of 5 challenged animals (Folgori et al., 2006 Nature Medicine 12, 190-7). Protection in this study was correlated with the mounting of T cell responses, in particular with the intrahepatic presence of CD8+ T cells specific of NS3 and NS5 antigens. Interestingly, the immunization scheme in that study was atypical in the sense that 3 adenovirus vaccinations were first performed followed by 3 injections of a DNA vaccine, this later vaccine was apparently added to improve mounting of specific CD4+ T cell responses that are notoriously weak following Ad5 vaccination. Similar to our observations, this Ad5 vaccine was also shown to induce genotype 1-cross protective responses. Both Folgori et al. (Folgori et al., 2006 Nature Medicine 12, 190-7), and our candidate vaccine contain subtype 1b sequences and are obviously capable for inducing responses cross-reacting with subtype 1a determinants as the challenge strains used in our study and in Folgoris' involve subtype 1a sequences. This feature is also very encouraging although clearly additional evaluations must be performed to more precisely measure the extent of the cross-reactivity induced.

In conclusion, we have designed and produced a HCV candidate vaccine based on a clinically approved MVA vaccine vector displaying a high and widely recognized safety profile. This vaccine, which is capable to mount potent, long lasting and cross-protective T cell mediated immune responses is currently entering phase I clinical trial.

The invention claimed is:

1. A method of treatment of one or more pathologies associated with an hepatitis C virus, which comprises at least three sequential administrations to a host organism of an effective dose of an expression vector wherein said expression vector comprises only two nucleotide sequences originating from hepatitis C virus which consist of (a) a nucleotide sequence coding for a polyprotein NS3/NS4 of an hepatitis C virus and (b) a nucleotide sequence coding for a polypeptide NS5b of an hepatitis C virus, wherein said at least three sequential administrations are independently separated by a period of time varying from 3 days to 10 days.

2. A method of stimulating a T cell-mediated immune response against an hepatitis C virus target protein which comprises the step of administering in a host organism an expression vector wherein said expression vector comprises only two nucleotide sequences originating from hepatitis C virus which consist of (a) a nucleotide sequence coding for a polyprotein NS3/NS4 of an hepatitis C virus and (b) a nucleotide sequence coding for a polypeptide NS5b of an hepatitis C virus, so as to stimulate a host's T cell-mediated immune response, wherein said method comprises at least three sequential administrations of said expression vector, and wherein said at least three sequential administrations are independently separated by a period of time varying from 3 days to 10 days.

3. The method according to claim 1 or 2, wherein said nucleotide sequences code for a polyprotein and a polypeptide originating from viruses of different genotypes.

4. The method according to claim 1 or 2, wherein said nucleotide sequences code for a polyprotein and a polypeptide originating from a virus of the same genotype, preferably the genotype 1b 5. The method according to claim 1 or 2, wherein the NS3/NS4 polyprotein encoded by the expression vector originates from a genotype 1b and the hepatitis C virus associated to the pathologies to be treated or to the target protein is of genotype 1a.

6. The method according to claim 1 or 2, wherein said expression vector is in association with a pharmaceutically appropriate vehicle.

7. The method according to claim 1 or 2, wherein the expression vector is a poxvirus.

8. The method according to claim 7, wherein the genome of the poxvirus is modified so as to insert the expression cassette ph5r-NS3-NS4 and to insert the expression cassette p7.5-NS5b.

9. The method according to claim 7, wherein the expression vector is a MVA whose genome is modified so as to insert the expression cassette ph5r-NS3-NS4 and the expression cassette p7.5- NS5b in deletion III and in the same direction.

10. The method according to claim 1 or 2, wherein said method comprises three sequential administrations at approximately one week interval of the expression vector.

11. The method according to claim 10, wherein said method further includes at least one "recall" administration at the end of the at least three sequential administrations.

12. The method according to claim 11, wherein said method comprises one recall administration which takes place at least approximately 4 weeks after the latest of the at least three sequential administrations.

13. The method according to claim 11, wherein said method comprises one recall administration which takes place approximately 6 months after the latest of the at least three sequential administrations.

14. The method according to claim 1 or 2, wherein the method is carried out in conjunction with treatment of the host organism with pegylated IFN-$\alpha$2 and/or ribavirin.

15. The method according to claim 2, wherein said stimulated immune response is a CD8+T cell response, a CD4+T cell response or both CD8+T and CD4+T cell responses.

16. The method according to claim 2, wherein said hepatitis C virus target protein is an epitope located in a NS3, and/or a NS4 and/or a NS5B protein.

17. The method according to claim 16, wherein said epitope is HLA-B7-restricted epitope and is located in the NS3 polypeptide of the infecting hepatitis virus.

18. The method according to claim 16, wherein said epitope is HLA-A2-restricted epitope and is located in the NS3 and/or NS5b protein of the infecting hepatitis virus.

19. The method according to claim 1 or 2, wherein said expression vector is administered to the host organism by an intramuscular or subcutaneous route.

20. A method for the inhibition or control of an infection caused by hepatitis C virus (HCV) in an animal, wherein said method comprises administering to an animal in need thereof an effective amount of at least one of the following:

(a) (i) an expression vector comprising HCV coding sequences, wherein said HCV coding sequences consist of a nucleotide sequence coding for an NS3/NS4 polyprotein of a HCV, and (ii) an expression vector comprising HCV coding sequences, wherein said HCV coding sequences consist of a nucleotide sequence coding for an NS5b polypeptide of a HCV; and (b) an expression vector comprising HCV coding sequences, wherein said HCV coding sequences consist of (i) a nucleotide sequence coding for an NS3/NS4 polyprotein of a HCV and (ii) a nucleotide sequence coding for an NS5b polypeptide of a HCV; wherein:

said method does not comprise administering a nucleotide sequence coding for an NS5a polypeptide of a HCV.

21. A method of inducing an immune response in an animal, wherein said method comprises administering to said animal an effective amount of at least one of the following:

(a) (i) an expression vector comprising HCV coding sequences, wherein said HCV coding sequences consist of a nucleotide sequence coding for an NS3/NS4 polyprotein of a HCV, and (ii) an expression vector comprising HCV coding sequences, wherein said HCV coding sequences consist of a nucleotide sequence coding for an NS5b polypeptide of a HCV; and (b) an expression vector comprising HCV coding sequences, wherein said HCV coding sequences consist of (i) a nucleotide sequence coding for an NS3/NS4 polyprotein of a HCV and (ii) a nucleotide sequence coding for an NS5b polypeptide of a HCV; wherein:

said method does not comprise administering a nucleotide sequence coding for an NS5a polypeptide of a HCV.

22. The method of claim 20 or 21, wherein said nucleotide sequence coding for a NS3/NS4 polyprotein of a HCV and said nucleotide sequence coding for a NS5b polypeptide of a HCV originate from viruses of different genotypes.

23. The method of claim 20 or 21, wherein said nucleotide sequence coding for a NS3/NS4 polyprotein of a HCV and said nucleotide sequence coding for a NS5b polypeptide of a HCV originate from a virus of the same genotype.

24. The method of claim 20 or 21, wherein said expression vectors(s) are adenoviruses.

25. The method of claim 24, wherein the genome of the adenovirus is modified so as to replace the E1 region by the expression cassette CMV-NS3-NS4 and to replace the E3 region by the expression cassette SV40-NS5b.

26. The method of claim 20 or 21, wherein said expression vectors are poxviruses.

27. The method of claim 26, wherein the genome of the poxvirus is modified so as to insert the expression cassette ph5r-NS3-NS4 and to insert the expression cassette p7.5-NS5b.

28. The method of claim 20 or 21, wherein said nucleotide sequence coding for a NS3/NS4 polyprotein of a HCV and said nucleotide sequence coding for a NS5b polypeptide of a HCV originate from a HCV of genotype 1b.

29. The method of claim 20, wherein said animal is a human.

30. The method of claim 21, wherein said immune response is a cell immune response.

31. The method of claim 21, wherein said animal is a human.

32. The method of claim 20 or 21 wherein said HCV coding sequences are operatively linked to one or more regulatory elements sufficient for the expression of said NS3/NS4 polyprotein and said NS5b polypeptide.

* * * * *

SEQUENCE LISTING

<160> NUMBER OF SEQ ID NOS: 31

<210> SEQ ID NO 1
<211> LENGTH: 2844
<212> TYPE: DNA
<213> ORGANISM: Artificial sequence
<220> FEATURE:
<223> OTHER INFORMATION: sequence coding for NS3NS4
<220> FEATURE:
<221> NAME/KEY: CDS
<222> LOCATION: (1)..(2844)

<400> SEQUENCE: 1

| | | |
|---|---|---|
| atg gcg cct atc acg gcc tat tcc caa caa acg cgg ggc ctg ctt ggc<br>Met Ala Pro Ile Thr Ala Tyr Ser Gln Gln Thr Arg Gly Leu Leu Gly<br>1               5                   10                  15 | 48 |
| tgt atc atc act agc ctc aca ggt cgg gac aag aac cag gtc gat ggg<br>Cys Ile Ile Thr Ser Leu Thr Gly Arg Asp Lys Asn Gln Val Asp Gly<br>            20                  25                  30 | 96 |
| gag gtt cag gtg ctc tcc acc gca acg caa tct ttc ctg gcg acc tgc<br>Glu Val Gln Val Leu Ser Thr Ala Thr Gln Ser Phe Leu Ala Thr Cys<br>        35                  40                  45 | 144 |
| gtc aat ggc gtg tgt tgg acc gtc tac cat ggt gcc ggc tcg aag acc<br>Val Asn Gly Val Cys Trp Thr Val Tyr His Gly Ala Gly Ser Lys Thr<br>    50                  55                  60 | 192 |
| ctg gcc ggc ccg aag ggt cca atc acc caa atg tac acc aat gta gac<br>Leu Ala Gly Pro Lys Gly Pro Ile Thr Gln Met Tyr Thr Asn Val Asp<br>65                  70                  75                  80 | 240 |
| cag gac ctc gtc ggc tgg cca gcg ccc ccc ggg gcg cgc tcc atg aca<br>Gln Asp Leu Val Gly Trp Pro Ala Pro Pro Gly Ala Arg Ser Met Thr<br>                85                  90                  95 | 288 |
| ccg tgc acc tgc ggc agc tcg gac ctt tac ttg gtc acg agg cat gcc<br>Pro Cys Thr Cys Gly Ser Ser Asp Leu Tyr Leu Val Thr Arg His Ala<br>            100                 105                 110 | 336 |
| gat gtc att ccg gtg cgc cgg cga ggc gac agc agg ggg agt cta ctc<br>Asp Val Ile Pro Val Arg Arg Arg Gly Asp Ser Arg Gly Ser Leu Leu<br>        115                 120                 125 | 384 |
| tcc cct agg ccc gtc tcc tac ctg aag ggc tcc tcg ggt gga cca ctg<br>Ser Pro Arg Pro Val Ser Tyr Leu Lys Gly Ser Ser Gly Gly Pro Leu<br>    130                 135                 140 | 432 |
| ctt tgc cct tcg ggg cac gtt gta ggc atc ttc cgg gct gct gtg tgc<br>Leu Cys Pro Ser Gly His Val Val Gly Ile Phe Arg Ala Ala Val Cys<br>145                 150                 155                 160 | 480 |
| acc cgg ggg gtt gcg aag gcg gtg gac ttc ata ccc gtt gag tct atg<br>Thr Arg Gly Val Ala Lys Ala Val Asp Phe Ile Pro Val Glu Ser Met<br>                165                 170                 175 | 528 |
| gaa act acc atg cgg tct ccg gtc ttc aca gac aac tca tcc cct ccg<br>Glu Thr Thr Met Arg Ser Pro Val Phe Thr Asp Asn Ser Ser Pro Pro<br>            180                 185                 190 | 576 |
| gcc gta ccg caa aca ttc caa gtg gca cat tta cac gct ccc act ggc<br>Ala Val Pro Gln Thr Phe Gln Val Ala His Leu His Ala Pro Thr Gly<br>        195                 200                 205 | 624 |
| agc ggc aag agc acc aaa gtg ccg gct gca tat gca gcc caa ggg tac<br>Ser Gly Lys Ser Thr Lys Val Pro Ala Ala Tyr Ala Ala Gln Gly Tyr<br>    210                 215                 220 | 672 |
| aag gtg ctc gtc cta aac ccg tcc gtt gct gcc aca ttg ggc ttt gga<br>Lys Val Leu Val Leu Asn Pro Ser Val Ala Ala Thr Leu Gly Phe Gly<br>225                 230                 235                 240 | 720 |
| gcg tat atg tcc aag gca cat ggc atc gag cct aac atc aga act ggg<br>Ala Tyr Met Ser Lys Ala His Gly Ile Glu Pro Asn Ile Arg Thr Gly | 768 |

-continued

```
                 245                 250                 255
gta agg acc atc acc acg ggc ggc ccc atc acg tac tcc acc tat ggc      816
Val Arg Thr Ile Thr Thr Gly Gly Pro Ile Thr Tyr Ser Thr Tyr Gly
        260                 265                 270 aag ttc ctt gcc gac ggt gga tgc tcc ggg ggc gcc tat gac atc ata      864
Lys Phe Leu Ala Asp Gly Gly Cys Ser Gly Gly Ala Tyr Asp Ile Ile
            275                 280                 285 ata tgt gac gaa tgc cac tca act gac tgg aca acc atc ttg ggc atc      912
Ile Cys Asp Glu Cys His Ser Thr Asp Trp Thr Thr Ile Leu Gly Ile
        290                 295                 300 ggc aca gtc ctg gat cag gca gag acg gct gga gcg cgg ctc gtc gtg      960
Gly Thr Val Leu Asp Gln Ala Glu Thr Ala Gly Ala Arg Leu Val Val
305                 310                 315                 320 ctc gcc acc gcc acg cct ccg gga tcg atc acc gtg cca cac ccc aac     1008
Leu Ala Thr Ala Thr Pro Pro Gly Ser Ile Thr Val Pro His Pro Asn
                325                 330                 335 atc gag gaa gtg gcc ctg tcc aac act ggg gag att ccc ttc tat ggc     1056
Ile Glu Glu Val Ala Leu Ser Asn Thr Gly Glu Ile Pro Phe Tyr Gly
            340                 345                 350 aaa gcc atc ccc att gag gcc atc aag ggg gga agg cat ctc atc ttc     1104
Lys Ala Ile Pro Ile Glu Ala Ile Lys Gly Gly Arg His Leu Ile Phe
        355                 360                 365 tgc cat tcc aag aag aag tgt gac gag ctc gcc gca aag ctg aca ggc     1152
Cys His Ser Lys Lys Lys Cys Asp Glu Leu Ala Ala Lys Leu Thr Gly
370                 375                 380 ctc gga ctc aat gct gta gcg tat tac cgg ggt ctc gat gtg tcc gtc     1200
Leu Gly Leu Asn Ala Val Ala Tyr Tyr Arg Gly Leu Asp Val Ser Val
385                 390                 395                 400 ata ccg act agc gga gac gtc gtt gtc gtg gca aca gac gct cta atg     1248
Ile Pro Thr Ser Gly Asp Val Val Val Val Ala Thr Asp Ala Leu Met
                405                 410                 415 acg ggc ttt acc ggc gac ttt gac tca gtg atc gac tgc aac aca tgt     1296
Thr Gly Phe Thr Gly Asp Phe Asp Ser Val Ile Asp Cys Asn Thr Cys
            420                 425                 430 gtc acc cag aca gtc gat ttc agc ttg gat ccc acc ttc acc att gag     1344
Val Thr Gln Thr Val Asp Phe Ser Leu Asp Pro Thr Phe Thr Ile Glu
        435                 440                 445 acg aca acc gtg ccc caa gac gcg gtg tcg cgc tcg cag cgg cga ggt     1392
Thr Thr Thr Val Pro Gln Asp Ala Val Ser Arg Ser Gln Arg Arg Gly
450                 455                 460 agg act ggc agg ggc agg agt ggc atc tac agg ttt gtg act cca gga     1440
Arg Thr Gly Arg Gly Arg Ser Gly Ile Tyr Arg Phe Val Thr Pro Gly
465                 470                 475                 480 gaa cgg ccc tca ggc atg ttc gac tcc tcg gtc ctg tgt gag tgc tat     1488
Glu Arg Pro Ser Gly Met Phe Asp Ser Ser Val Leu Cys Glu Cys Tyr
                485                 490                 495 gac gca ggc tgc gct tgg tat gag ctc acg ccc gct gag act aca gtc     1536
Asp Ala Gly Cys Ala Trp Tyr Glu Leu Thr Pro Ala Glu Thr Thr Val
            500                 505                 510 agg ttg cgg gct tac ctg aat aca cca ggg ttg ccc gtc tgc cag gac     1584
Arg Leu Arg Ala Tyr Leu Asn Thr Pro Gly Leu Pro Val Cys Gln Asp
        515                 520                 525 cat ctg gag ttc tgg gaa agc gtc ttc aca ggc ctc acc cac ata gat     1632
His Leu Glu Phe Trp Glu Ser Val Phe Thr Gly Leu Thr His Ile Asp
530                 535                 540 gcc cac ttc ctg tcc caa acc aag cag gca gga gac aac ttc ccc tac     1680
Ala His Phe Leu Ser Gln Thr Lys Gln Ala Gly Asp Asn Phe Pro Tyr
545                 550                 555                 560 ctg gtg gca tac caa gcc acg gtg tgc gcc agg gct cag gct cca cct     1728
```

```
                Leu Val Ala Tyr Gln Ala Thr Val Cys Ala Arg Ala Gln Ala Pro Pro
                                565                 570                 575 cca tcg tgg gat caa atg tgg aag tgt ctc ata cgg ctt aaa cct acg          1776
Pro Ser Trp Asp Gln Met Trp Lys Cys Leu Ile Arg Leu Lys Pro Thr
            580                 585                 590 ctg cac ggg cca aca ccc ctg ctg tat agg cta gga gcc gtt caa aat          1824
Leu His Gly Pro Thr Pro Leu Leu Tyr Arg Leu Gly Ala Val Gln Asn
                595                 600                 605 gag atc acc ctc aca cat ccc ata acc aaa ttc gtc atg gca tgc atg          1872
Glu Ile Thr Leu Thr His Pro Ile Thr Lys Phe Val Met Ala Cys Met
            610                 615                 620 tcg gcc gac ctg gag gtc gtc act agc acc tgg gtg ctg gta ggc gga          1920
Ser Ala Asp Leu Glu Val Val Thr Ser Thr Trp Val Leu Val Gly Gly
625                 630                 635                 640 gtc ctt gca gct ctg gcc gca tat tgc ctg aca acc ggt agt gtg gtc          1968
Val Leu Ala Ala Leu Ala Ala Tyr Cys Leu Thr Thr Gly Ser Val Val
                645                 650                 655 att gtg ggt agg atc att ttg tcc ggg agg ccg gct gtt gtt ccc gac          2016
Ile Val Gly Arg Ile Ile Leu Ser Gly Arg Pro Ala Val Val Pro Asp
            660                 665                 670 agg gaa gtc ctc tac cgg gag ttc gat gaa atg gaa gag tgc gcc tca          2064
Arg Glu Val Leu Tyr Arg Glu Phe Asp Glu Met Glu Glu Cys Ala Ser
                675                 680                 685 cac ctc cct tac atc gag caa gga atg cag ctc gcc gag cag ttc aag          2112
His Leu Pro Tyr Ile Glu Gln Gly Met Gln Leu Ala Glu Gln Phe Lys
            690                 695                 700 cag cag gca ctc ggg ttg ctg caa aca gcc acc aag caa gcg gag gcc          2160
Gln Gln Ala Leu Gly Leu Leu Gln Thr Ala Thr Lys Gln Ala Glu Ala
705                 710                 715                 720 gct gct ccc gtg gtg gag tcc agg tgg cgg gcc ctt gag gcc ttc tgg          2208
Ala Ala Pro Val Val Glu Ser Arg Trp Arg Ala Leu Glu Ala Phe Trp
                725                 730                 735 gca aag cac atg tgg aac ttc atc agc ggg ata cag tac tta gca ggc          2256
Ala Lys His Met Trp Asn Phe Ile Ser Gly Ile Gln Tyr Leu Ala Gly
            740                 745                 750 tta tcc act ctg cct ggg aac ccc gcg ata gca tca ctg atg gca ttc          2304
Leu Ser Thr Leu Pro Gly Asn Pro Ala Ile Ala Ser Leu Met Ala Phe
                755                 760                 765 aca gcc tct atc acc agt ccg ctc acc acc cag aat acc ctc cta ttc          2352
Thr Ala Ser Ile Thr Ser Pro Leu Thr Thr Gln Asn Thr Leu Leu Phe
            770                 775                 780 aac atc tta ggg gga tgg gtg gct gct caa ctc gct cct ccc agt gct          2400
Asn Ile Leu Gly Gly Trp Val Ala Ala Gln Leu Ala Pro Pro Ser Ala
785                 790                 795                 800 gct tcg gcc ttc gtg ggt gcc ggc att gcc ggt gcg gcc att ggc agc          2448
Ala Ser Ala Phe Val Gly Ala Gly Ile Ala Gly Ala Ala Ile Gly Ser
                805                 810                 815 ata ggc ctt ggg aag gtg ctt gtg gac att ctg gcg ggc tat gga gcg          2496
Ile Gly Leu Gly Lys Val Leu Val Asp Ile Leu Ala Gly Tyr Gly Ala
            820                 825                 830 ggg gtg gcc ggt gca ctc gtg gct ttt aag gtc atg agc ggc gag gcg          2544
Gly Val Ala Gly Ala Leu Val Ala Phe Lys Val Met Ser Gly Glu Ala
                835                 840                 845 ccc tcc gcc gag gac ctg gtt aac ttg ctc cct gcc atc ctc tcc ccc          2592
Pro Ser Ala Glu Asp Leu Val Asn Leu Leu Pro Ala Ile Leu Ser Pro
            850                 855                 860 ggc gcc ttg gtc gtc ggg atc gtg tgt gca gca atc ctg cgt cgg cac          2640
Gly Ala Leu Val Val Gly Ile Val Cys Ala Ala Ile Leu Arg Arg His
865                 870                 875                 880
```

-continued

| | | |
|---|---|---|
| gtg ggc ccg gga gag ggg gct gtg cag tgg atg aac cgg ctg ata gcg<br>Val Gly Pro Gly Glu Gly Ala Val Gln Trp Met Asn Arg Leu Ile Ala<br>885                      890                    895 | | 2688 |
| ttc gct tcg cgg ggt aac cac gtt tcc ccc acg cac tac gtg cct gag<br>Phe Ala Ser Arg Gly Asn His Val Ser Pro Thr His Tyr Val Pro Glu<br>900                      905                    910 | | 2736 |
| agc gac gcc gca gca cgt gta act cag atc ctc tcc agc ctc acc atc<br>Ser Asp Ala Ala Ala Arg Val Thr Gln Ile Leu Ser Ser Leu Thr Ile<br>915                      920                    925 | | 2784 |
| act cag ctg ctg aag agg ctt cac cag tgg att aat gag gac tgc tcc<br>Thr Gln Leu Leu Lys Arg Leu His Gln Trp Ile Asn Glu Asp Cys Ser<br>930                      935                    940 | | 2832 |
| acg cca tgc taa<br>Thr Pro Cys<br>945 | | 2844 |

<210> SEQ ID NO 2
<211> LENGTH: 947
<212> TYPE: PRT
<213> ORGANISM: Artificial sequence
<220> FEATURE:
<223> OTHER INFORMATION: sequence coding for NS3NS4

<400> SEQUENCE: 2

Met Ala Pro Ile Thr Ala Tyr Ser Gln Gln Thr Arg Gly Leu Leu Gly
1               5                   10                   15

Cys Ile Ile Thr Ser Leu Thr Gly Arg Asp Lys Asn Gln Val Asp Gly
                 20                   25                   30

Glu Val Gln Val Leu Ser Thr Ala Thr Gln Ser Phe Leu Ala Thr Cys
              35                   40                 45

Val Asn Gly Val Cys Trp Thr Val Tyr His Gly Ala Gly Ser Lys Thr
50                      55                   60

Leu Ala Gly Pro Lys Gly Pro Ile Thr Gln Met Tyr Thr Asn Val Asp
65                     70                   75                   80

Gln Asp Leu Val Gly Trp Pro Ala Pro Pro Gly Ala Arg Ser Met Thr
                 85                   90                   95

Pro Cys Thr Cys Gly Ser Ser Asp Leu Tyr Leu Val Thr Arg His Ala
               100                   105                  110

Asp Val Ile Pro Val Arg Arg Arg Gly Asp Ser Arg Gly Ser Leu Leu
             115                   120                  125

Ser Pro Arg Pro Val Ser Tyr Leu Lys Gly Ser Ser Gly Gly Pro Leu
130                   135                  140

Leu Cys Pro Ser Gly His Val Val Gly Ile Phe Arg Ala Ala Val Cys
145                   150                  155                  160

Thr Arg Gly Val Ala Lys Ala Val Asp Phe Ile Pro Val Glu Ser Met
                 165                   170                  175

Glu Thr Thr Met Arg Ser Pro Val Phe Thr Asp Asn Ser Ser Pro Pro
             180                   185                  190

Ala Val Pro Gln Thr Phe Gln Val Ala His Leu His Ala Pro Thr Gly
             195                   200                  205

Ser Gly Lys Ser Thr Lys Val Pro Ala Ala Tyr Ala Ala Gln Gly Tyr
210                   215                  220

Lys Val Leu Val Leu Asn Pro Ser Val Ala Ala Thr Leu Gly Phe Gly
225                   230                  235                  240

Ala Tyr Met Ser Lys Ala His Gly Ile Glu Pro Asn Ile Arg Thr Gly
                 245                   250                  255

Val Arg Thr Ile Thr Thr Gly Gly Pro Ile Thr Tyr Ser Thr Tyr Gly

```
                260             265             270
Lys Phe Leu Ala Asp Gly Gly Cys Ser Gly Gly Ala Tyr Asp Ile Ile
            275             280             285
Ile Cys Asp Glu Cys His Ser Thr Asp Trp Thr Thr Ile Leu Gly Ile
        290             295             300
Gly Thr Val Leu Asp Gln Ala Glu Thr Ala Gly Ala Arg Leu Val Val
305             310             315             320
Leu Ala Thr Ala Thr Pro Pro Gly Ser Ile Thr Val Pro His Pro Asn
                325             330             335
Ile Glu Glu Val Ala Leu Ser Asn Thr Gly Glu Ile Pro Phe Tyr Gly
            340             345             350
Lys Ala Ile Pro Ile Glu Ala Ile Lys Gly Gly Arg His Leu Ile Phe
        355             360             365
Cys His Ser Lys Lys Lys Cys Asp Glu Leu Ala Ala Lys Leu Thr Gly
    370             375             380
Leu Gly Leu Asn Ala Val Ala Tyr Tyr Arg Gly Leu Asp Val Ser Val
385             390             395             400
Ile Pro Thr Ser Gly Asp Val Val Val Ala Thr Asp Ala Leu Met
                405             410             415
Thr Gly Phe Thr Gly Asp Phe Asp Ser Val Ile Asp Cys Asn Thr Cys
            420             425             430
Val Thr Gln Thr Val Asp Phe Ser Leu Asp Pro Thr Phe Thr Ile Glu
        435             440             445
Thr Thr Thr Val Pro Gln Asp Ala Val Ser Arg Ser Gln Arg Gly
    450             455             460
Arg Thr Gly Arg Gly Arg Ser Gly Ile Tyr Arg Phe Val Thr Pro Gly
465             470             475             480
Glu Arg Pro Ser Gly Met Phe Asp Ser Ser Val Leu Cys Glu Cys Tyr
                485             490             495
Asp Ala Gly Cys Ala Trp Tyr Glu Leu Thr Pro Ala Glu Thr Thr Val
            500             505             510
Arg Leu Arg Ala Tyr Leu Asn Thr Pro Gly Leu Pro Val Cys Gln Asp
        515             520             525
His Leu Glu Phe Trp Glu Ser Val Phe Thr Gly Leu Thr His Ile Asp
    530             535             540
Ala His Phe Leu Ser Gln Thr Lys Gln Ala Gly Asp Asn Phe Pro Tyr
545             550             555             560
Leu Val Ala Tyr Gln Ala Thr Val Cys Ala Arg Ala Gln Ala Pro Pro
                565             570             575
Pro Ser Trp Asp Gln Met Trp Lys Cys Leu Ile Arg Leu Lys Pro Thr
            580             585             590
Leu His Gly Pro Thr Pro Leu Leu Tyr Arg Leu Gly Ala Val Gln Asn
        595             600             605
Glu Ile Thr Leu Thr His Pro Ile Thr Lys Phe Val Met Ala Cys Met
    610             615             620
Ser Ala Asp Leu Glu Val Val Thr Ser Thr Trp Val Leu Val Gly Gly
625             630             635             640
Val Leu Ala Ala Leu Ala Ala Tyr Cys Leu Thr Thr Gly Ser Val Val
                645             650             655
Ile Val Gly Arg Ile Ile Leu Ser Gly Arg Pro Ala Val Val Pro Asp
            660             665             670
Arg Glu Val Leu Tyr Arg Glu Phe Asp Glu Met Glu Glu Cys Ala Ser
        675             680             685
```

```
His Leu Pro Tyr Ile Glu Gln Gly Met Gln Leu Ala Glu Gln Phe Lys
    690             695                 700
Gln Gln Ala Leu Gly Leu Leu Gln Thr Ala Thr Lys Gln Ala Glu Ala
705             710                 715                 720
Ala Ala Pro Val Val Glu Ser Arg Trp Arg Ala Leu Glu Ala Phe Trp
                725                 730                 735
Ala Lys His Met Trp Asn Phe Ile Ser Gly Ile Gln Tyr Leu Ala Gly
            740                 745                 750
Leu Ser Thr Leu Pro Gly Asn Pro Ala Ile Ala Ser Leu Met Ala Phe
        755                 760                 765
Thr Ala Ser Ile Thr Ser Pro Leu Thr Thr Gln Asn Thr Leu Leu Phe
    770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Ile Gly Ser
                805                 810                 815
Ile Gly Leu Gly Lys Val Leu Val Asp Ile Leu Ala Gly Tyr Gly Ala
            820                 825                 830
Gly Val Ala Gly Ala Leu Val Ala Phe Lys Val Met Ser Gly Glu Ala
        835                 840                 845
Pro Ser Ala Glu Asp Leu Val Asn Leu Leu Pro Ala Ile Leu Ser Pro
    850                 855                 860
Gly Ala Leu Val Val Gly Ile Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
            900                 905                 910
Ser Asp Ala Ala Ala Arg Val Thr Gln Ile Leu Ser Ser Leu Thr Ile
        915                 920                 925
Thr Gln Leu Leu Lys Arg Leu His Gln Trp Ile Asn Glu Asp Cys Ser
    930                 935                 940
Thr Pro Cys
945
```

<210> SEQ ID NO 3
<211> LENGTH: 1779
<212> TYPE: DNA
<213> ORGANISM: Artificial sequence
<220> FEATURE:
<223> OTHER INFORMATION: sequence coding for NS5b
<220> FEATURE:
<221> NAME/KEY: CDS
<222> LOCATION: (1)..(1779)

<400> SEQUENCE: 3

```
atg tca atg tcc tac aca tgg aca ggt gcc ttg atc acg cca tgc gct    48
Met Ser Met Ser Tyr Thr Trp Thr Gly Ala Leu Ile Thr Pro Cys Ala
1               5                   10                  15 gcg gag gag agc aag ttg ccc atc aat ccg ttg agc aac tct ttg ctg    96
Ala Glu Glu Ser Lys Leu Pro Ile Asn Pro Leu Ser Asn Ser Leu Leu
                20                  25                  30 cgt cac cac agt atg gtc tac tcc aca aca tct cgc agc gca agt ctg   144
Arg His His Ser Met Val Tyr Ser Thr Thr Ser Arg Ser Ala Ser Leu
            35                  40                  45 cgg cag aag aag gtc acc ttt gac aga ctg caa gtc ctg gac gac cac   192
Arg Gln Lys Lys Val Thr Phe Asp Arg Leu Gln Val Leu Asp Asp His
```

```
           50                  55                  60
tac cgg gac gtg ctc aag gag atg aag gcg aag gcg tcc aca gtt aag      240
Tyr Arg Asp Val Leu Lys Glu Met Lys Ala Lys Ala Ser Thr Val Lys
 65                  70                  75                  80 gct agg ctt cta tct ata gag gag gcc tgc aaa ctg acg ccc cca cat      288
Ala Arg Leu Leu Ser Ile Glu Glu Ala Cys Lys Leu Thr Pro Pro His
                 85                  90                  95 tcg gcc aaa tcc aaa ttt ggc tac ggg gcg aag gac gtc cgg agc cta      336
Ser Ala Lys Ser Lys Phe Gly Tyr Gly Ala Lys Asp Val Arg Ser Leu
             100                 105                 110 tcc agc agg gcc gtc aac cac atc cgc tcc gtg tgg gag gac ttg ctg      384
Ser Ser Arg Ala Val Asn His Ile Arg Ser Val Trp Glu Asp Leu Leu
         115                 120                 125 gaa gac act gaa aca cca att gat acc acc atc atg gca aaa aat gag      432
Glu Asp Thr Glu Thr Pro Ile Asp Thr Thr Ile Met Ala Lys Asn Glu
     130                 135                 140 gtt ttc tgc gtc caa cca gag aaa gga ggc cgc aag cca gct cgc ctt      480
Val Phe Cys Val Gln Pro Glu Lys Gly Gly Arg Lys Pro Ala Arg Leu
145                 150                 155                 160 atc gta ttc cca gac ctg ggg gta cgt gta tgc gag aag atg gcc ctt      528
Ile Val Phe Pro Asp Leu Gly Val Arg Val Cys Glu Lys Met Ala Leu
                 165                 170                 175 tac gac gtg gtc tcc acc ctt cct cag gcc gtg atg ggc ccc tca tac      576
Tyr Asp Val Val Ser Thr Leu Pro Gln Ala Val Met Gly Pro Ser Tyr
             180                 185                 190 gga ttc cag tac tct cct ggg cag cgg gtc gag ttc ctg gtg aat acc      624
Gly Phe Gln Tyr Ser Pro Gly Gln Arg Val Glu Phe Leu Val Asn Thr
         195                 200                 205 tgg aaa tca aag aaa tgc cct atg ggc ttc tca tat gac acc cgc tgc      672
Trp Lys Ser Lys Lys Cys Pro Met Gly Phe Ser Tyr Asp Thr Arg Cys
     210                 215                 220 ttt gac tca acg gtc act gag aat gac atc cgt act gag gag tca atc      720
Phe Asp Ser Thr Val Thr Glu Asn Asp Ile Arg Thr Glu Glu Ser Ile
225                 230                 235                 240 tac caa tgt tgt gac ttg gcc ccc gaa gcc aga cag gcc ata aag tcg      768
Tyr Gln Cys Cys Asp Leu Ala Pro Glu Ala Arg Gln Ala Ile Lys Ser
                 245                 250                 255 ctc aca gag cgg ctc tac atc ggg ggt ccc ctg act aat tca aaa ggg      816
Leu Thr Glu Arg Leu Tyr Ile Gly Gly Pro Leu Thr Asn Ser Lys Gly
             260                 265                 270 cag aac tgc ggt tat cgc cgg tgc cgc gcg agc ggc gtg ctg acg act      864
Gln Asn Cys Gly Tyr Arg Arg Cys Arg Ala Ser Gly Val Leu Thr Thr
         275                 280                 285 agc tgc ggc aat acc ctc aca tgc tac ttg aaa gcc act gcg gcc tgt      912
Ser Cys Gly Asn Thr Leu Thr Cys Tyr Leu Lys Ala Thr Ala Ala Cys
     290                 295                 300 cga gct gca aag ctc cag gac tgc acg atg ctc gtg aac gga gac gac      960
Arg Ala Ala Lys Leu Gln Asp Cys Thr Met Leu Val Asn Gly Asp Asp
305                 310                 315                 320 ctt gtc gtt atc tgc gaa agc gcg gga acc cag gag gat gcg gcg agc     1008
Leu Val Val Ile Cys Glu Ser Ala Gly Thr Gln Glu Asp Ala Ala Ser
                 325                 330                 335 cta cga gtc ttc acg gag gct atg act agg tac tct gcc ccc ccc ggg     1056
Leu Arg Val Phe Thr Glu Ala Met Thr Arg Tyr Ser Ala Pro Pro Gly
             340                 345                 350 gac ccg ccc caa cca gaa tac gac ttg gag ctg ata acg tca tgc tcc     1104
Asp Pro Pro Gln Pro Glu Tyr Asp Leu Glu Leu Ile Thr Ser Cys Ser
         355                 360                 365 tcc aat gtg tcg gtc gcg cac gat gca tcc ggc aaa agg gtg tac tac     1152
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Ser | Asn | Val | Ser | Val | Ala | His | Asp | Ala | Ser | Gly | Lys | Arg | Val | Tyr | Tyr |      |
|     | 370 |     |     |     | 375 |     |     |     |     | 380 |     |     |     |     |     |      |
| ctc | acc | cgt | gac | ccc | acc | acc | ccc | ctc | gca | cgg | gct | gcg | tgg | gag | aca | 1200 |
| Leu | Thr | Arg | Asp | Pro | Thr | Thr | Pro | Leu | Ala | Arg | Ala | Ala | Trp | Glu | Thr |      |
| 385 |     |     |     |     | 390 |     |     |     |     | 395 |     |     |     |     | 400 |      |
| gtt | aga | cac | act | cca | gtc | aac | tcc | tgg | cta | ggc | aat | atc | atc | atg | tat | 1248 |
| Val | Arg | His | Thr | Pro | Val | Asn | Ser | Trp | Leu | Gly | Asn | Ile | Ile | Met | Tyr |      |
|     |     |     |     | 405 |     |     |     |     | 410 |     |     |     |     | 415 |     |      |
| gcg | ccc | acc | cta | tgg | gcg | agg | atg | att | ctg | atg | act | cat | ttc | ttc | tct | 1296 |
| Ala | Pro | Thr | Leu | Trp | Ala | Arg | Met | Ile | Leu | Met | Thr | His | Phe | Phe | Ser |      |
|     |     |     | 420 |     |     |     |     | 425 |     |     |     |     | 430 |     |     |      |
| atc | ctt | cta | gct | cag | gag | caa | ctt | gaa | aaa | gcc | ctg | gat | tgt | cag | atc | 1344 |
| Ile | Leu | Leu | Ala | Gln | Glu | Gln | Leu | Glu | Lys | Ala | Leu | Asp | Cys | Gln | Ile |      |
|     |     | 435 |     |     |     |     | 440 |     |     |     |     | 445 |     |     |     |      |
| tac | ggg | gcc | tgc | tac | tcc | att | gag | cca | ctt | gac | cta | cct | cag | atc | atc | 1392 |
| Tyr | Gly | Ala | Cys | Tyr | Ser | Ile | Glu | Pro | Leu | Asp | Leu | Pro | Gln | Ile | Ile |      |
|     | 450 |     |     |     |     | 455 |     |     |     |     | 460 |     |     |     |     |      |
| gaa | cga | ctc | cat | ggt | ctt | agc | gca | ttt | tca | ctc | cat | agt | tac | tct | cca | 1440 |
| Glu | Arg | Leu | His | Gly | Leu | Ser | Ala | Phe | Ser | Leu | His | Ser | Tyr | Ser | Pro |      |
| 465 |     |     |     |     | 470 |     |     |     |     | 475 |     |     |     |     | 480 |      |
| ggt | gag | atc | aat | agg | gtg | gct | tca | tgc | ctc | agg | aaa | ctt | ggg | gta | cca | 1488 |
| Gly | Glu | Ile | Asn | Arg | Val | Ala | Ser | Cys | Leu | Arg | Lys | Leu | Gly | Val | Pro |      |
|     |     |     |     | 485 |     |     |     |     | 490 |     |     |     |     | 495 |     |      |
| ccc | ttg | cga | gtc | tgg | aga | cat | cgg | gcc | aga | agt | gtc | cgc | gct | aag | ttg | 1536 |
| Pro | Leu | Arg | Val | Trp | Arg | His | Arg | Ala | Arg | Ser | Val | Arg | Ala | Lys | Leu |      |
|     |     |     | 500 |     |     |     |     | 505 |     |     |     |     | 510 |     |     |      |
| ctg | tcc | cag | ggg | ggg | agg | gcc | gcc | act | tgc | ggc | aaa | tac | ctc | ttc | aac | 1584 |
| Leu | Ser | Gln | Gly | Gly | Arg | Ala | Ala | Thr | Cys | Gly | Lys | Tyr | Leu | Phe | Asn |      |
|     |     | 515 |     |     |     |     | 520 |     |     |     |     | 525 |     |     |     |      |
| tgg | gca | gta | agg | acc | aag | ctt | aaa | ctc | act | cca | atc | ccg | gct | gcg | tcc | 1632 |
| Trp | Ala | Val | Arg | Thr | Lys | Leu | Lys | Leu | Thr | Pro | Ile | Pro | Ala | Ala | Ser |      |
|     | 530 |     |     |     |     | 535 |     |     |     |     | 540 |     |     |     |     |      |
| cag | cta | gac | ttg | tcc | ggc | tgg | ttc | gtt | gct | ggt | tac | aac | ggg | gga | gac | 1680 |
| Gln | Leu | Asp | Leu | Ser | Gly | Trp | Phe | Val | Ala | Gly | Tyr | Asn | Gly | Gly | Asp |      |
| 545 |     |     |     |     | 550 |     |     |     |     | 555 |     |     |     |     | 560 |      |
| ata | tat | cac | agc | ctg | tct | cgt | gcc | cga | ccc | cgt | tgg | ttc | atg | ttg | tgc | 1728 |
| Ile | Tyr | His | Ser | Leu | Ser | Arg | Ala | Arg | Pro | Arg | Trp | Phe | Met | Leu | Cys |      |
|     |     |     |     | 565 |     |     |     |     | 570 |     |     |     |     | 575 |     |      |
| cta | ctc | cta | ctt | tct | gta | ggg | gta | ggc | atc | tac | ctg | ctc | ccc | aac | cgg | 1776 |
| Leu | Leu | Leu | Leu | Ser | Val | Gly | Val | Gly | Ile | Tyr | Leu | Leu | Pro | Asn | Arg |      |
|     |     |     | 580 |     |     |     |     | 585 |     |     |     |     | 590 |     |     |      |
| taa |     |     |     |     |     |     |     |     |     |     |     |     |     |     |     | 1779 |

<210> SEQ ID NO 4
<211> LENGTH: 592
<212> TYPE: PRT
<213> ORGANISM: Artificial sequence
<220> FEATURE:
<223> OTHER INFORMATION: sequence coding for NS5b

<400> SEQUENCE: 4

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ser | Met | Ser | Tyr | Thr | Trp | Thr | Gly | Ala | Leu | Ile | Thr | Pro | Cys | Ala |
| 1   |     |     |     | 5   |     |     |     |     | 10  |     |     |     |     | 15  |     |
| Ala | Glu | Glu | Ser | Lys | Leu | Pro | Ile | Asn | Pro | Leu | Ser | Asn | Ser | Leu | Leu |
|     |     |     | 20  |     |     |     |     | 25  |     |     |     |     | 30  |     |     |
| Arg | His | His | Ser | Met | Val | Tyr | Ser | Thr | Thr | Ser | Arg | Ser | Ala | Ser | Leu |
|     |     | 35  |     |     |     |     | 40  |     |     |     |     | 45  |     |     |     |
| Arg | Gln | Lys | Lys | Val | Thr | Phe | Asp | Arg | Leu | Gln | Val | Leu | Asp | Asp | His |
|     | 50  |     |     |     |     | 55  |     |     |     |     | 60  |     |     |     |     |

-continued

```
Tyr Arg Asp Val Leu Lys Glu Met Lys Ala Lys Ala Ser Thr Val Lys
 65                  70                  75                  80

Ala Arg Leu Leu Ser Ile Glu Glu Ala Cys Lys Leu Thr Pro Pro His
                 85                  90                  95

Ser Ala Lys Ser Lys Phe Gly Tyr Gly Ala Lys Asp Val Arg Ser Leu
            100                 105                 110

Ser Ser Arg Ala Val Asn His Ile Arg Ser Val Trp Glu Asp Leu Leu
        115                 120                 125

Glu Asp Thr Glu Thr Pro Ile Asp Thr Thr Ile Met Ala Lys Asn Glu
    130                 135                 140

Val Phe Cys Val Gln Pro Glu Lys Gly Gly Arg Lys Pro Ala Arg Leu
145                 150                 155                 160

Ile Val Phe Pro Asp Leu Gly Val Arg Val Cys Glu Lys Met Ala Leu
                165                 170                 175

Tyr Asp Val Val Ser Thr Leu Pro Gln Ala Val Met Gly Pro Ser Tyr
            180                 185                 190

Gly Phe Gln Tyr Ser Pro Gly Gln Arg Val Glu Phe Leu Val Asn Thr
        195                 200                 205

Trp Lys Ser Lys Lys Cys Pro Met Gly Phe Ser Tyr Asp Thr Arg Cys
    210                 215                 220

Phe Asp Ser Thr Val Thr Glu Asn Asp Ile Arg Thr Glu Glu Ser Ile
225                 230                 235                 240

Tyr Gln Cys Cys Asp Leu Ala Pro Glu Ala Arg Gln Ala Ile Lys Ser
                245                 250                 255

Leu Thr Glu Arg Leu Tyr Ile Gly Gly Pro Leu Thr Asn Ser Lys Gly
            260                 265                 270

Gln Asn Cys Gly Tyr Arg Arg Cys Arg Ala Ser Gly Val Leu Thr Thr
        275                 280                 285

Ser Cys Gly Asn Thr Leu Thr Cys Tyr Leu Lys Ala Thr Ala Ala Cys
    290                 295                 300

Arg Ala Ala Lys Leu Gln Asp Cys Thr Met Leu Val Asn Gly Asp Asp
305                 310                 315                 320

Leu Val Val Ile Cys Glu Ser Ala Gly Thr Gln Glu Asp Ala Ala Ser
                325                 330                 335

Leu Arg Val Phe Thr Glu Ala Met Thr Arg Tyr Ser Ala Pro Pro Gly
            340                 345                 350

Asp Pro Pro Gln Pro Glu Tyr Asp Leu Glu Leu Ile Thr Ser Cys Ser
        355                 360                 365

Ser Asn Val Ser Val Ala His Asp Ala Ser Gly Lys Arg Val Tyr Tyr
    370                 375                 380

Leu Thr Arg Asp Pro Thr Thr Pro Leu Ala Arg Ala Ala Trp Glu Thr
385                 390                 395                 400

Val Arg His Thr Pro Val Asn Ser Trp Leu Gly Asn Ile Ile Met Tyr
                405                 410                 415

Ala Pro Thr Leu Trp Ala Arg Met Ile Leu Met Thr His Phe Phe Ser
            420                 425                 430

Ile Leu Leu Ala Gln Glu Gln Leu Glu Lys Ala Leu Asp Cys Gln Ile
        435                 440                 445

Tyr Gly Ala Cys Tyr Ser Ile Glu Pro Leu Asp Leu Pro Gln Ile Ile
    450                 455                 460

Glu Arg Leu His Gly Leu Ser Ala Phe Ser Leu His Ser Tyr Ser Pro
465                 470                 475                 480

Gly Glu Ile Asn Arg Val Ala Ser Cys Leu Arg Lys Leu Gly Val Pro
```

-continued

```
                485                 490                 495
Pro Leu Arg Val Trp Arg His Arg Ala Arg Ser Val Arg Ala Lys Leu
            500                 505                 510

Leu Ser Gln Gly Gly Arg Ala Ala Thr Cys Gly Lys Tyr Leu Phe Asn
            515                 520                 525

Trp Ala Val Arg Thr Lys Leu Lys Leu Thr Pro Ile Pro Ala Ala Ser
            530                 535                 540

Gln Leu Asp Leu Ser Gly Trp Phe Val Ala Gly Tyr Asn Gly Gly Asp
545                 550                 555                 560

Ile Tyr His Ser Leu Ser Arg Ala Arg Pro Arg Trp Phe Met Leu Cys
            565                 570                 575

Leu Leu Leu Leu Ser Val Gly Val Gly Ile Tyr Leu Leu Pro Asn Arg
            580                 585                 590
```

<210> SEQ ID NO 5
<211> LENGTH: 1344
<212> TYPE: DNA
<213> ORGANISM: Artificial sequence
<220> FEATURE:
<223> OTHER INFORMATION: sequence coding for NS5a
<220> FEATURE:
<221> NAME/KEY: CDS
<222> LOCATION: (1)..(1344)

<400> SEQUENCE: 5

| | | |
|---|---|---|
| atg tcc ggc tcg tgg cta agg gat gtt tgg gac tgg ata tgc acg gtg<br>Met Ser Gly Ser Trp Leu Arg Asp Val Trp Asp Trp Ile Cys Thr Val<br>1                   5                  10               15 | | 48 |
| ttg act gac ttc aag acc tgg ctc cag tcc aag ctc ctg ccg aaa ttg<br>Leu Thr Asp Phe Lys Thr Trp Leu Gln Ser Lys Leu Leu Pro Lys Leu<br>               20                  25               30 | | 96 |
| ccg gga gtc cct ttc ttc tca tgc caa cgc ggg tac aag gga gtc tgg<br>Pro Gly Val Pro Phe Phe Ser Cys Gln Arg Gly Tyr Lys Gly Val Trp<br>               35                  40               45 | | 144 |
| cgg ggg gac ggc atc atg caa acc acc tgc cca tgt gga gca caa att<br>Arg Gly Asp Gly Ile Met Gln Thr Thr Cys Pro Cys Gly Ala Gln Ile<br> 50                  55                  60 | | 192 |
| acc gga cat gtc aaa aac ggt tcc atg agg atc gtt ggg cct aaa acc<br>Thr Gly His Val Lys Asn Gly Ser Met Arg Ile Val Gly Pro Lys Thr<br>65                   70                  75               80 | | 240 |
| tgc agc aac acg tgg cac gga acg ttc ccc atc aac gcg tac acc aca<br>Cys Ser Asn Thr Trp His Gly Thr Phe Pro Ile Asn Ala Tyr Thr Thr<br>               85                  90               95 | | 288 |
| ggc ccc tgc aca ccc tcc ccg gcg ccg aac tat tcc agg gcg ctg tgg<br>Gly Pro Cys Thr Pro Ser Pro Ala Pro Asn Tyr Ser Arg Ala Leu Trp<br>              100              105             110 | | 336 |
| cgg gtg gct gct gaa gag tac gtg gag att acg cgg gtg ggg gac ttc<br>Arg Val Ala Ala Glu Glu Tyr Val Glu Ile Thr Arg Val Gly Asp Phe<br>              115              120             125 | | 384 |
| cac tac gtg acg ggt atg acc acc gac aac gta aaa tgc ccg tgc cag<br>His Tyr Val Thr Gly Met Thr Thr Asp Asn Val Lys Cys Pro Cys Gln<br>       130               135              140 | | 432 |
| gtc ccg gcc ccc gaa ttc ttc act gaa ttg gac ggg gtg cgg ttg cac<br>Val Pro Ala Pro Glu Phe Phe Thr Glu Leu Asp Gly Val Arg Leu His<br>145                  150              155             160 | | 480 |
| agg tac gct ccg gcg tgc aga cct ctc cta cgg gtg gat gtc aca ttc<br>Arg Tyr Ala Pro Ala Cys Arg Pro Leu Leu Arg Val Asp Val Thr Phe<br>              165              170             175 | | 528 |
| cag gtc ggg ctc aac caa tac ctg gtt ggg tca cag ctc cca tgc gag<br>Gln Val Gly Leu Asn Gln Tyr Leu Val Gly Ser Gln Leu Pro Cys Glu | | 576 |

-continued

```
                    180                 185                 190
cct gag ccg gat gtg gca gtg ctc act tcc atg ctc acc gac ccc tcc      624
Pro Glu Pro Asp Val Ala Val Leu Thr Ser Met Leu Thr Asp Pro Ser
        195                 200                 205 cac att aca gca gag acg gct aaa cgt agg ccg gcc agg ggg tct ccc      672
His Ile Thr Ala Glu Thr Ala Lys Arg Arg Pro Ala Arg Gly Ser Pro
    210                 215                 220 ccc tcc ttg gcc agc tct tca gct agc caa ttg tct gcg cct tcc ttg      720
Pro Ser Leu Ala Ser Ser Ser Ala Ser Gln Leu Ser Ala Pro Ser Leu
225                 230                 235                 240 aag gca aca tgc act acc cac cat gac tcc ccg gac gct gac ctc atc      768
Lys Ala Thr Cys Thr Thr His His Asp Ser Pro Asp Ala Asp Leu Ile
                245                 250                 255 gag gcc aac ctc ctg tgg cgg cag gag atg ggc gga aac atc acc cgt      816
Glu Ala Asn Leu Leu Trp Arg Gln Glu Met Gly Gly Asn Ile Thr Arg
            260                 265                 270 gtg gag tca gag aat aag gtg gta att ttg gac tct ttc gac ccg ctt      864
Val Glu Ser Glu Asn Lys Val Val Ile Leu Asp Ser Phe Asp Pro Leu
        275                 280                 285 cga gcg gaa gag gat gag agg gaa gta tcc gtt gca gca gag atc ctg      912
Arg Ala Glu Glu Asp Glu Arg Glu Val Ser Val Ala Ala Glu Ile Leu
    290                 295                 300 cga aaa tcc aag aag ttc ccc ccc gcg ttg ccc ata tgg gca cgc ccg      960
Arg Lys Ser Lys Lys Phe Pro Pro Ala Leu Pro Ile Trp Ala Arg Pro
305                 310                 315                 320 gat tac aac cct cca ctg tta gag tcc tgg aaa agt ccg gac tac gtc     1008
Asp Tyr Asn Pro Pro Leu Leu Glu Ser Trp Lys Ser Pro Asp Tyr Val
                325                 330                 335 cct ccg gcg gtg cat ggg tgc cca ttg ccg cct acc acg ggc cct cca     1056
Pro Pro Ala Val His Gly Cys Pro Leu Pro Pro Thr Thr Gly Pro Pro
            340                 345                 350 ata ccg cct cca cgg aaa aag agg acg gtt gtt ctg aca gag tcc acc     1104
Ile Pro Pro Pro Arg Lys Lys Arg Thr Val Val Leu Thr Glu Ser Thr
        355                 360                 365 gtg tct tct gcc ttg gcg gag ctg gct act aag act ttc ggc agc tcc     1152
Val Ser Ser Ala Leu Ala Glu Leu Ala Thr Lys Thr Phe Gly Ser Ser
370                 375                 380 gga tcg tcg gcc gtt gac agc ggc acg gcg acc gcc cct ccc gat cag     1200
Gly Ser Ser Ala Val Asp Ser Gly Thr Ala Thr Ala Pro Pro Asp Gln
385                 390                 395                 400 acc tct gac gac ggt gac aaa gaa tct gac att gag tcg tac tcc tcc     1248
Thr Ser Asp Asp Gly Asp Lys Glu Ser Asp Ile Glu Ser Tyr Ser Ser
                405                 410                 415 atg ccc ccc ctt gag ggg gag ccg ggg gac cct gat ctc agc gac ggg     1296
Met Pro Pro Leu Glu Gly Glu Pro Gly Asp Pro Asp Leu Ser Asp Gly
            420                 425                 430 tct tgg tct acc gtg agc ggg gag gcc ggc gac gac atc gtc tgc tgc     1344
Ser Trp Ser Thr Val Ser Gly Glu Ala Gly Asp Asp Ile Val Cys Cys
        435                 440                 445

<210> SEQ ID NO 6
<211> LENGTH: 448
<212> TYPE: PRT
<213> ORGANISM: Artificial sequence
<220> FEATURE:
<223> OTHER INFORMATION: sequence coding for NS5a

<400> SEQUENCE: 6

Met Ser Gly Ser Trp Leu Arg Asp Val Trp Asp Trp Ile Cys Thr Val
1               5                   10                  15
```

-continued

```
Leu Thr Asp Phe Lys Thr Trp Leu Gln Ser Lys Leu Leu Pro Lys Leu
         20                  25                  30

Pro Gly Val Pro Phe Phe Ser Cys Gln Arg Gly Tyr Lys Gly Val Trp
             35                  40                  45

Arg Gly Asp Gly Ile Met Gln Thr Thr Cys Pro Cys Gly Ala Gln Ile
 50                  55                  60

Thr Gly His Val Lys Asn Gly Ser Met Arg Ile Val Gly Pro Lys Thr
 65                  70                  75                  80

Cys Ser Asn Thr Trp His Gly Thr Phe Pro Ile Asn Ala Tyr Thr Thr
                 85                  90                  95

Gly Pro Cys Thr Pro Ser Pro Ala Pro Asn Tyr Ser Arg Ala Leu Trp
            100                 105                 110

Arg Val Ala Ala Glu Glu Tyr Val Glu Ile Thr Arg Val Gly Asp Phe
            115                 120                 125

His Tyr Val Thr Gly Met Thr Thr Asp Asn Val Lys Cys Pro Cys Gln
        130                 135                 140

Val Pro Ala Pro Glu Phe Phe Thr Glu Leu Asp Gly Val Arg Leu His
145                 150                 155                 160

Arg Tyr Ala Pro Ala Cys Arg Pro Leu Leu Arg Val Asp Val Thr Phe
                165                 170                 175

Gln Val Gly Leu Asn Gln Tyr Leu Val Gly Ser Gln Leu Pro Cys Glu
            180                 185                 190

Pro Glu Pro Asp Val Ala Val Leu Thr Ser Met Leu Thr Asp Pro Ser
        195                 200                 205

His Ile Thr Ala Glu Thr Ala Lys Arg Arg Pro Ala Arg Gly Ser Pro
    210                 215                 220

Pro Ser Leu Ala Ser Ser Ser Ala Ser Gln Leu Ser Ala Pro Ser Leu
225                 230                 235                 240

Lys Ala Thr Cys Thr Thr His His Asp Ser Pro Asp Ala Asp Leu Ile
                245                 250                 255

Glu Ala Asn Leu Leu Trp Arg Gln Glu Met Gly Gly Asn Ile Thr Arg
            260                 265                 270

Val Glu Ser Glu Asn Lys Val Val Ile Leu Asp Ser Phe Asp Pro Leu
        275                 280                 285

Arg Ala Glu Glu Asp Glu Arg Glu Val Ser Val Ala Ala Glu Ile Leu
    290                 295                 300

Arg Lys Ser Lys Lys Phe Pro Pro Ala Leu Pro Ile Trp Ala Arg Pro
305                 310                 315                 320

Asp Tyr Asn Pro Pro Leu Leu Glu Ser Trp Lys Ser Pro Asp Tyr Val
                325                 330                 335

Pro Pro Ala Val His Gly Cys Pro Leu Pro Pro Thr Thr Gly Pro Pro
            340                 345                 350

Ile Pro Pro Arg Lys Lys Arg Thr Val Val Leu Thr Glu Ser Thr
        355                 360                 365

Val Ser Ser Ala Leu Ala Glu Leu Ala Thr Lys Thr Phe Gly Ser Ser
    370                 375                 380

Gly Ser Ser Ala Val Asp Ser Gly Thr Ala Thr Ala Pro Pro Asp Gln
385                 390                 395                 400

Thr Ser Asp Asp Gly Asp Lys Glu Ser Asp Ile Glu Ser Tyr Ser Ser
                405                 410                 415

Met Pro Pro Leu Glu Gly Glu Pro Gly Asp Pro Asp Leu Ser Asp Gly
            420                 425                 430

Ser Trp Ser Thr Val Ser Gly Glu Ala Gly Asp Asp Ile Val Cys Cys
```

<210> SEQ ID NO 7
<211> LENGTH: 2241
<212> TYPE: DNA
<213> ORGANISM: Artificial sequence
<220> FEATURE:
<223> OTHER INFORMATION: sequence coding for CE1E2
<220> FEATURE:
<221> NAME/KEY: CDS
<222> LOCATION: (1)..(2241)

<400> SEQUENCE: 7

```
atg agc aca aat cct aaa cct caa aga aaa acc aaa cgt aac acc aac        48
Met Ser Thr Asn Pro Lys Pro Gln Arg Lys Thr Lys Arg Asn Thr Asn
1               5                   10                  15 cgc cgc cca cag gac gtt aag ttc ccg ggt ggt ggt cag atc gtt ggt        96
Arg Arg Pro Gln Asp Val Lys Phe Pro Gly Gly Gly Gln Ile Val Gly
                20                  25                  30 gga gtt tac ctg ttg ccg cgc agg ggc ccc agg ttg ggt gtg cgc gcg       144
Gly Val Tyr Leu Leu Pro Arg Arg Gly Pro Arg Leu Gly Val Arg Ala
            35                  40                  45 act agg aag act tcc gag cgg tcg caa cct cgt gga agg cga caa cct       192
Thr Arg Lys Thr Ser Glu Arg Ser Gln Pro Arg Gly Arg Arg Gln Pro
        50                  55                  60 atc ccc aag gct cgc cgg ccc gag ggt agg acc tgg gct cag ccc ggg       240
Ile Pro Lys Ala Arg Arg Pro Glu Gly Arg Thr Trp Ala Gln Pro Gly
65                  70                  75                  80 tac cct tgg ccc ctc tat ggc aac gag ggt atg ggg tgg gca gga tgg       288
Tyr Pro Trp Pro Leu Tyr Gly Asn Glu Gly Met Gly Trp Ala Gly Trp
                85                  90                  95 ctc ctg tca ccc cgt ggc tct cgg cct agt tgg ggc ccc aca gac ccc       336
Leu Leu Ser Pro Arg Gly Ser Arg Pro Ser Trp Gly Pro Thr Asp Pro
                100                 105                 110 cgg cgt agg tcg cgt aat ttg ggt aag gtc atc gat acc ctt aca tgc       384
Arg Arg Arg Ser Arg Asn Leu Gly Lys Val Ile Asp Thr Leu Thr Cys
            115                 120                 125 ggc ttc gcc gac ctc atg ggg tac att ccg ctt gtc ggc gcc ccc cta       432
Gly Phe Ala Asp Leu Met Gly Tyr Ile Pro Leu Val Gly Ala Pro Leu
        130                 135                 140 gga ggc gct gcc agg gcc ctg gcg cat ggc gtc cgg gtt ctg gag gac       480
Gly Gly Ala Ala Arg Ala Leu Ala His Gly Val Arg Val Leu Glu Asp
145                 150                 155                 160 ggc gtg aac tat gca aca ggg aat ctg ccc ggt tgc tct ttc tct atc       528
Gly Val Asn Tyr Ala Thr Gly Asn Leu Pro Gly Cys Ser Phe Ser Ile
                165                 170                 175 ttc ctc tta gct ttg ctg tct tgt ttg acc atc cca gct tcc gct tac       576
Phe Leu Leu Ala Leu Leu Ser Cys Leu Thr Ile Pro Ala Ser Ala Tyr
                180                 185                 190 gag gtg cgc aac gtg tcc gga ata tac cat gtc acg aac gac tgc tcc       624
Glu Val Arg Asn Val Ser Gly Ile Tyr His Val Thr Asn Asp Cys Ser
            195                 200                 205 aac tca agt att gtg tat gag gca gcg gac atg atc atg cac acc ccc       672
Asn Ser Ser Ile Val Tyr Glu Ala Ala Asp Met Ile Met His Thr Pro
        210                 215                 220 ggg tgc gtg ccc tgc gtc cgg gag agt aat ttc tcc cgt tgc tgg gta       720
Gly Cys Val Pro Cys Val Arg Glu Ser Asn Phe Ser Arg Cys Trp Val
225                 230                 235                 240 gcg ctc act ccc acg ctc gcg gcc agg aac agc agc atc ccc acc acg       768
Ala Leu Thr Pro Thr Leu Ala Ala Arg Asn Ser Ser Ile Pro Thr Thr
                245                 250                 255
```

```
aca ata cga cgc cac gtc gat ttg ctc gtt ggg gcg gct gct ctc tgt     816
Thr Ile Arg Arg His Val Asp Leu Leu Val Gly Ala Ala Ala Leu Cys
        260                 265                 270 tcc gct atg tac gtt ggg gat ctc tgc gga tcc gtt ttt ctc gtc tcc     864
Ser Ala Met Tyr Val Gly Asp Leu Cys Gly Ser Val Phe Leu Val Ser
            275                 280                 285 cag ctg ttc acc ttc tca cct cgc cgg tat gag acg gta caa gat tgc     912
Gln Leu Phe Thr Phe Ser Pro Arg Arg Tyr Glu Thr Val Gln Asp Cys
    290                 295                 300 aat tgc tca atc tat ccc ggc cac gta tca ggt cac cgc atg gct tgg     960
Asn Cys Ser Ile Tyr Pro Gly His Val Ser Gly His Arg Met Ala Trp
305                 310                 315                 320 gat atg atg atg aac tgg tca cct aca acg gcc cta gtg gta tcg cag    1008
Asp Met Met Met Asn Trp Ser Pro Thr Thr Ala Leu Val Val Ser Gln
                325                 330                 335 cta ctc cgg atc cca caa gcc gtc gtg gac atg gtg gcg ggg gcc cac    1056
Leu Leu Arg Ile Pro Gln Ala Val Val Asp Met Val Ala Gly Ala His
            340                 345                 350 tgg ggt gtc cta gcg ggc ctt gcc tac tat tcc atg gtg ggg aac tgg    1104
Trp Gly Val Leu Ala Gly Leu Ala Tyr Tyr Ser Met Val Gly Asn Trp
        355                 360                 365 gct aag gtc ttg att gtg atg cta ctc ttt gct ggc gtt gac ggg cac    1152
Ala Lys Val Leu Ile Val Met Leu Leu Phe Ala Gly Val Asp Gly His
370                 375                 380 acc cac gtg aca ggg gga agg gta gcc tcc agc acc cag agc ctc gtg    1200
Thr His Val Thr Gly Gly Arg Val Ala Ser Ser Thr Gln Ser Leu Val
385                 390                 395                 400 tcc tgg ctc tca caa ggg cca tct cag aaa atc caa ctc gtg aac acc    1248
Ser Trp Leu Ser Gln Gly Pro Ser Gln Lys Ile Gln Leu Val Asn Thr
                405                 410                 415 aac ggc agc tgg cac atc aac agg acc gct ctg aat tgc aat gac tcc    1296
Asn Gly Ser Trp His Ile Asn Arg Thr Ala Leu Asn Cys Asn Asp Ser
            420                 425                 430 ctc caa act ggg ttc att gct gcg ctg ttc tac gca cac agg ttc aac    1344
Leu Gln Thr Gly Phe Ile Ala Ala Leu Phe Tyr Ala His Arg Phe Asn
        435                 440                 445 gcg tcc gga tgt cca gag cgc atg gcc agc tgc cgc ccc atc gac aag    1392
Ala Ser Gly Cys Pro Glu Arg Met Ala Ser Cys Arg Pro Ile Asp Lys
    450                 455                 460 ttc gct cag ggg tgg ggt ccc atc act cac gtt gtg cct aac atc tcg    1440
Phe Ala Gln Gly Trp Gly Pro Ile Thr His Val Val Pro Asn Ile Ser
465                 470                 475                 480 gac cag agg cct tat tgc tgg cac tat gca ccc caa ccg tgc ggt att    1488
Asp Gln Arg Pro Tyr Cys Trp His Tyr Ala Pro Gln Pro Cys Gly Ile
                485                 490                 495 gta ccc gcg tcg cag gtg tgt ggc cca gtg tat tgc ttc acc ccg agt    1536
Val Pro Ala Ser Gln Val Cys Gly Pro Val Tyr Cys Phe Thr Pro Ser
            500                 505                 510 cct gtt gtg gtg ggg acg acc gac cgt tcc gga gtc ccc acg tat agc    1584
Pro Val Val Val Gly Thr Thr Asp Arg Ser Gly Val Pro Thr Tyr Ser
        515                 520                 525 tgg ggg gag aat gag aca gac gtg ctg cta ctc aac aac acg cgg ccg    1632
Trp Gly Glu Asn Glu Thr Asp Val Leu Leu Leu Asn Asn Thr Arg Pro
    530                 535                 540 ccg caa ggc aac tgg ttc ggc tgt aca tgg atg aat agc acc ggg ttc    1680
Pro Gln Gly Asn Trp Phe Gly Cys Thr Trp Met Asn Ser Thr Gly Phe
545                 550                 555                 560 acc aag acg tgc ggg ggc ccc ccg tgt aac atc ggg ggg gtt ggc aac    1728
Thr Lys Thr Cys Gly Gly Pro Pro Cys Asn Ile Gly Gly Val Gly Asn
                565                 570                 575
```

```
aac acc ttg att tgc ccc acg gat tgc ttc cga aag cac ccc gag gcc    1776
Asn Thr Leu Ile Cys Pro Thr Asp Cys Phe Arg Lys His Pro Glu Ala
            580                 585                 590 act tac acc aaa tgc ggc tcg ggt cct tgg ttg aca cct agg tgt cta    1824
Thr Tyr Thr Lys Cys Gly Ser Gly Pro Trp Leu Thr Pro Arg Cys Leu
        595                 600                 605 gtt gac tac cca tac aga ctt tgg cac tac ccc tgc act atc aat ttt    1872
Val Asp Tyr Pro Tyr Arg Leu Trp His Tyr Pro Cys Thr Ile Asn Phe
    610                 615                 620 acc atc ttc aag gtc agg atg tac gtg ggg ggc gtg gag cac agg ctc    1920
Thr Ile Phe Lys Val Arg Met Tyr Val Gly Gly Val Glu His Arg Leu
625                 630                 635                 640 aac gcc gcg tgc aat tgg acc cga gga gag cgc tgt gac ctg gag gac    1968
Asn Ala Ala Cys Asn Trp Thr Arg Gly Glu Arg Cys Asp Leu Glu Asp
                645                 650                 655 agg gat aga tca gag ctt agc ccg cta tta tct aca acg gag tgg        2016
Arg Asp Arg Ser Glu Leu Ser Pro Leu Leu Ser Thr Thr Glu Trp
            660                 665                 670 cag gta ctg ccc tgt tcc ttt acc acc cta ccg gct ctg tcc act gga    2064
Gln Val Leu Pro Cys Ser Phe Thr Thr Leu Pro Ala Leu Ser Thr Gly
        675                 680                 685 ttg atc cac ctc cat cag aat atc gtg gac gtg caa tac ctg tac ggt    2112
Leu Ile His Leu His Gln Asn Ile Val Asp Val Gln Tyr Leu Tyr Gly
    690                 695                 700 gta ggg tca gtg gtt gtc tcc gtc gta atc aaa tgg gag tat gtt ctg    2160
Val Gly Ser Val Val Val Ser Val Val Ile Lys Trp Glu Tyr Val Leu
705                 710                 715                 720 ctg ctc ttc ctt ctc ctg gcg gac gcg cgc gtc tgt gcc tgc ttg tgg    2208
Leu Leu Phe Leu Leu Leu Ala Asp Ala Arg Val Cys Ala Cys Leu Trp
                725                 730                 735 atg atg ctg ctg ata gcc cag gct gag gcc tga                        2241
Met Met Leu Leu Ile Ala Gln Ala Glu Ala
                740                 745

<210> SEQ ID NO 8
<211> LENGTH: 746
<212> TYPE: PRT
<213> ORGANISM: Artificial sequence
<220> FEATURE:
<223> OTHER INFORMATION: sequence coding for CE1E2

<400> SEQUENCE: 8

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ile Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Ser Asn Phe Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
                260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg Tyr Glu Thr Val Gln Asp Cys
290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly His
                370                 375                 380

Thr His Val Thr Gly Gly Arg Val Ala Ser Ser Thr Gln Ser Leu Val
385                 390                 395                 400

Ser Trp Leu Ser Gln Gly Pro Ser Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu Gln Thr Gly Phe Ile Ala Ala Leu Phe Tyr Ala His Arg Phe Asn
                435                 440                 445

Ala Ser Gly Cys Pro Glu Arg Met Ala Ser Cys Arg Pro Ile Asp Lys
450                 455                 460

Phe Ala Gln Gly Trp Gly Pro Ile Thr His Val Val Pro Asn Ile Ser
465                 470                 475                 480

Asp Gln Arg Pro Tyr Cys Trp His Tyr Ala Pro Gln Pro Cys Gly Ile
                485                 490                 495

Val Pro Ala Ser Gln Val Cys Gly Pro Val Tyr Cys Phe Thr Pro Ser
                500                 505                 510

Pro Val Val Val Gly Thr Thr Asp Arg Ser Gly Val Pro Thr Tyr Ser
                515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Ser Thr Gly Phe
```

|     |     |     |     |     |     |     |     |     |     |
|-----|-----|-----|-----|-----|-----|-----|-----|-----|-----|
| 545 |     |     |     |     | 550 |     |     |     |     | 555 |     |     |     |     | 560 |

Thr Lys Thr Cys Gly Gly Pro Pro Cys Asn Ile Gly Val Gly Asn
            565                  570             575

Asn Thr Leu Ile Cys Pro Thr Asp Cys Phe Arg Lys His Pro Glu Ala
            580              585              590

Thr Tyr Thr Lys Cys Gly Ser Gly Pro Trp Leu Thr Pro Arg Cys Leu
        595              600              605

Val Asp Tyr Pro Tyr Arg Leu Trp His Tyr Pro Cys Thr Ile Asn Phe
   610               615              620

Thr Ile Phe Lys Val Arg Met Tyr Val Gly Gly Val Glu His Arg Leu
625            630              635             640

Asn Ala Ala Cys Asn Trp Thr Arg Gly Glu Arg Cys Asp Leu Glu Asp
            645              650              655

Arg Asp Arg Ser Glu Leu Ser Pro Leu Leu Leu Ser Thr Thr Glu Trp
        660              665              670

Gln Val Leu Pro Cys Ser Phe Thr Thr Leu Pro Ala Leu Ser Thr Gly
        675              680              685

Leu Ile His Leu His Gln Asn Ile Val Asp Val Gln Tyr Leu Tyr Gly
   690               695              700

Val Gly Ser Val Val Val Ser Val Val Ile Lys Trp Glu Tyr Val Leu
705            710              715             720

Leu Leu Phe Leu Leu Leu Ala Asp Ala Arg Val Cys Ala Cys Leu Trp
            725              730              735

Met Met Leu Leu Ile Ala Gln Ala Glu Ala
        740              745

<210> SEQ ID NO 9
<211> LENGTH: 29
<212> TYPE: DNA
<213> ORGANISM: Artificial sequence
<220> FEATURE:
<223> OTHER INFORMATION: primer oIV166

<400> SEQUENCE: 9
gggggggcta tggcgcctat cacggccta         29

<210> SEQ ID NO 10
<211> LENGTH: 32
<212> TYPE: DNA
<213> ORGANISM: Artificial sequence
<220> FEATURE:
<223> OTHER INFORMATION: primer oIV171

<400> SEQUENCE: 10 gggggggacgc gtttagcatg gcgtggagca gt         32

<210> SEQ ID NO 11
<211> LENGTH: 30
<212> TYPE: DNA
<213> ORGANISM: Artificial sequence
<220> FEATURE:
<223> OTHER INFORMATION: primer oIV232

<400> SEQUENCE: 11 gggggggagat ctccagcagg cagaagtatg         30

<210> SEQ ID NO 12
<211> LENGTH: 33
<212> TYPE: DNA
<213> ORGANISM: Artificial sequence

```
<220> FEATURE:
<223> OTHER INFORMATION: primer oIV233

<400> SEQUENCE: 12
gggggggtcg accgaaaatg gatatacaag ctc                                33

<210> SEQ ID NO 13
<211> LENGTH: 35
<212> TYPE: DNA
<213> ORGANISM: Artificial sequence
<220> FEATURE:
<223> OTHER INFORMATION: primer oIV212

<400> SEQUENCE: 13 gggggggtcta gaatgtcaat gtcctacaca tggac                             35

<210> SEQ ID NO 14
<211> LENGTH: 32
<212> TYPE: DNA
<213> ORGANISM: Artificial sequence
<220> FEATURE:
<223> OTHER INFORMATION: primer oIV218

<400> SEQUENCE: 14 gggggggtcta gattaccggt tggggagcag gt                                32

<210> SEQ ID NO 15
<211> LENGTH: 32
<212> TYPE: DNA
<213> ORGANISM: Artificial sequence
<220> FEATURE:
<223> OTHER INFORMATION: primer oIV225

<400> SEQUENCE: 15 gggggggctgc agatggcgcc tatcacggcc ta                                32

<210> SEQ ID NO 16
<211> LENGTH: 32
<212> TYPE: DNA
<213> ORGANISM: Artificial sequence
<220> FEATURE:
<223> OTHER INFORMATION: primer oIV226

<400> SEQUENCE: 16 gggggggtcta gattagcatg gcgtggagca gt                                32

<210> SEQ ID NO 17
<211> LENGTH: 35
<212> TYPE: DNA
<213> ORGANISM: Artificial sequence
<220> FEATURE:
<223> OTHER INFORMATION: primer oIV227

<400> SEQUENCE: 17 ggggggggtcg acatgtcaat gtcctacaca tggac                             35

<210> SEQ ID NO 18
<211> LENGTH: 32
<212> TYPE: DNA
<213> ORGANISM: Artificial sequence
<220> FEATURE:
<223> OTHER INFORMATION: primer oIV228

<400> SEQUENCE: 18
gggggggcat gcttaccggt tggggagcag gt                                 32
```

```
<210> SEQ ID NO 19
<211> LENGTH: 33
<212> TYPE: DNA
<213> ORGANISM: Artificial sequence
<220> FEATURE:
<223> OTHER INFORMATION: primer oIV229

<400> SEQUENCE: 19 gggggggtcta gaccggtagt tcgcatatac ata                         33

<210> SEQ ID NO 20
<211> LENGTH: 33
<212> TYPE: DNA
<213> ORGANISM: Artificial sequence
<220> FEATURE:
<223> OTHER INFORMATION: primer oIV172

<400> SEQUENCE: 20
ggggggggta ccatgtccgg ctcgtggcta agg                          33

<210> SEQ ID NO 21
<211> LENGTH: 33
<212> TYPE: DNA
<213> ORGANISM: Artificial sequence
<220> FEATURE:
<223> OTHER INFORMATION: primer oIV173

<400> SEQUENCE: 21 gggggggtcta gattagcagc agacgatgtc gtc                         33

<210> SEQ ID NO 22
<211> LENGTH: 33
<212> TYPE: DNA
<213> ORGANISM: Artificial sequence
<220> FEATURE:
<223> OTHER INFORMATION: primer oIV62

<400> SEQUENCE: 22
gggggggcta gcatgagcac aaatcctaaa cct                          33

<210> SEQ ID NO 23
<211> LENGTH: 33
<212> TYPE: DNA
<213> ORGANISM: Artificial sequence
<220> FEATURE:
<223> OTHER INFORMATION: primer oIV68

<400> SEQUENCE: 23 gggggggtcta gatcaggcct cagcctgggc tat                         33

<210> SEQ ID NO 24
<211> LENGTH: 10
<212> TYPE: PRT
<213> ORGANISM: Artificial sequence
<220> FEATURE:
<223> OTHER INFORMATION: epitope GLL

<400> SEQUENCE: 24

Gly Leu Leu Gly Cys Ile Ile Thr Ser Leu
1               5                   10

<210> SEQ ID NO 25
<211> LENGTH: 9
<212> TYPE: PRT
<213> ORGANISM: Artificial sequence
<220> FEATURE:
```

```
<223> OTHER INFORMATION: epitope ALY

<400> SEQUENCE: 25

Ala Leu Tyr Asp Val Val Ser Thr Leu
1               5

<210> SEQ ID NO 26
<211> LENGTH: 9
<212> TYPE: PRT
<213> ORGANISM: Artificial sequence
<220> FEATURE:
<223> OTHER INFORMATION: epitope KLQ

<400> SEQUENCE: 26

Lys Leu Gln Asp Cys Thr Met Leu Val
1               5

<210> SEQ ID NO 27
<211> LENGTH: 9
<212> TYPE: PRT
<213> ORGANISM: Artificial sequence
<220> FEATURE:
<223> OTHER INFORMATION: epitope DLM

<400> SEQUENCE: 27

Asp Leu Met Gly Tyr Ile Pro Leu Val
1               5

<210> SEQ ID NO 28
<211> LENGTH: 9
<212> TYPE: PRT
<213> ORGANISM: Artificial sequence
<220> FEATURE:
<223> OTHER INFORMATION: epitope CVN

<400> SEQUENCE: 28

Cys Val Asn Gly Val Cys Trp Thr Val
1               5

<210> SEQ ID NO 29
<211> LENGTH: 10
<212> TYPE: PRT
<213> ORGANISM: Artificial sequence
<220> FEATURE:
<223> OTHER INFORMATION: epitope KLT

<400> SEQUENCE: 29

Lys Leu Thr Gly Leu Gly Leu Asn Ala Val
1               5                   10

<210> SEQ ID NO 30
<211> LENGTH: 10
<212> TYPE: PRT
<213> ORGANISM: Artificial sequence
<220> FEATURE:
<223> OTHER INFORMATION: epitope WPA10

<400> SEQUENCE: 30

Trp Pro Ala Pro Pro Gly Ala Arg Ser Met
1               5                   10

<210> SEQ ID NO 31
<211> LENGTH: 10
<212> TYPE: PRT
<213> ORGANISM: Artificial sequence
<220> FEATURE:
<223> OTHER INFORMATION: epitope LSP10
```

```
<400> SEQUENCE: 31

Leu Ser Pro Arg Pro Val Ser Tyr Leu Lys
1               5                   10
```